United States Patent
Cox et al.

(10) Patent No.: US 6,528,494 B2
(45) Date of Patent: Mar. 4, 2003

(54) 2-(PURIN-9-YL)-TETRAHYDROFURAN-3,4-DIOL DERIVATIVES

(76) Inventors: Brian Cox, Glaxo Wellcome plc. Gunnels Wood Road, Stevenage, Hertfordshire (GB), SG1 2NY; Suzanne Elaine Keeling, Glaxo Wellcome plc. Gunnels Wood Road, Stevenage, Herfordshire (GB), SG1 2NY; David George Allen, Glaxo Wellcome plc. Gunnels Wood Road, Stevenage, Hertfordshire (GB), SG1 2NY; Alison Judith Redgrave, Glaxo Wellcome plc. Gunnels Wood Road, Stevenage, Hertfordshire (GB), SG1 2NY; Michael David Barker, Glaxo Wellcome plc. Gunnels Wood Road, Stevenage, Hertfordshire (GB), SG1 2NY; Heather Hobbs, Glaxo Wellcome plc. Gunnels Wood Road, Stevenage, Hertfordshire (GB), SG1 2NY; Thomas Davis Roper, IV, Glaxo Wellcome Inc. Five Moore Dr., Research Triangle Park, NC (US) 27709; Joanna Victoria Geden, OSI Pharmaceuticals (Aston Molecules) 10 Holt Ct. South, Aston Science Park, Birmingham (GB), B7 4EJ ( * ) Notice: Subject to any disclaimer, the term of this patent is extended or adjusted under 35 U.S.C. 154(b) by 0 days.

(21) Appl. No.: 10/025,678
(22) Filed: Dec. 19, 2001

(65) Prior Publication Data

US 2002/0086850 A1 Jul. 4, 2002

Related U.S. Application Data

(63) Continuation of application No. 09/331,526, filed as application No. PCT/EP97/07197 on Dec. 22, 1997, now Pat. No. 6,426,337.

(30) Foreign Application Priority Data

| Dec. 24, 1996 | (GB) | 9626845 |
|---|---|---|
| Dec. 24, 1996 | (GB) | 9626846 |
| Dec. 24, 1996 | (GB) | 9626852 |
| Sep. 27, 1997 | (GB) | 9720536 |
| Oct. 29, 1997 | (GB) | 9722730 |

(51) Int. Cl.$^7$ .......................... A01N 43/04; A61K 31/70
(52) U.S. Cl. ..................... 514/45; 514/46; 514/47; 514/826; 514/851; 514/885; 514/921; 514/925
(58) Field of Search .................. 514/45, 46, 47, 514/826, 851, 885, 921, 925

(56) References Cited

U.S. PATENT DOCUMENTS

| 3,864,483 A | 2/1975 | Stein et al. |
|---|---|---|
| 3,966,917 A | 6/1976 | Prasad et al. |
| 3,983,104 A | 9/1976 | Vorbruggen |
| 4,167,565 A | 9/1979 | Stein et al. |
| 4,663,313 A | 5/1987 | Bristol et al. |
| 4,704,381 A | 11/1987 | Schaumann et al. |
| 4,767,747 A | 8/1988 | Hamilton et al. |
| 4,962,194 A | 10/1990 | Bridges |
| 4,968,697 A | 11/1990 | Hutchinson |
| 4,985,409 A | 1/1991 | Yamada et al. |
| 5,043,325 A | 8/1991 | Olsson et al. |
| 5,106,837 A | 4/1992 | Carson et al. |
| 5,219,839 A | 6/1993 | Bru-Magniez et al. |
| 5,219,840 A | 6/1993 | Gadient et al. |
| 5,280,015 A | 1/1994 | Jacobson et al. |
| 5,364,862 A | 11/1994 | Spada et al. |
| 5,424,297 A | 6/1995 | Rubio et al. |

FOREIGN PATENT DOCUMENTS

| AU | 610822 | 4/1987 |
|---|---|---|
| BE | 768925 | 6/1971 |

(List continued on next page.)

OTHER PUBLICATIONS

W. Jahn, et al., "Synthese 5'–substitutierter Adenosinderivate," Chemische Berichte, vol. 98, No. 6, 1965, p. 1705–1708.

J. Kobe, et al., "Preparation and Utility of 5–B–D–fibofuranosyl–1H–tetrazole as a Key Synthon for C–nucleoside Synthesis," Nucleosides and Nucleotides, vol. 13, No. 10, 1994, pp. 2209–2244.

Chiara Dianzani, et al., "Adenosine modulation of primed human neutrophils," *European Journal of Pharmacology* 263 (1994) pp. 223–226.

Keith R.F. Elliott, et al., "Interactions of formylemethionyl–leucyl–phenylalanine, adenoise, and phosphodiesterase inhibitors in human monocytes," *Feb 07518—FEBS Letters*, vol. 254, No. 1,2, pp. 94–98, Aug. 1989.

(List continued on next page.)

Primary Examiner—James O. Wilson
Assistant Examiner—Patrick Lewis

(57) ABSTRACT

There are provided according to the invention novel compounds of formula I

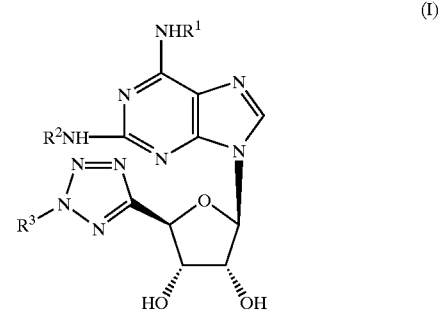

wherein $R^1$, $R^2$ and $R^3$ are as described in the specification, processes for preparing them, formulations containing them and their use in therapy for the treatment of inflammatory diseases.

2 Claims, No Drawings

FOREIGN PATENT DOCUMENTS

| | | |
|---|---|---|
| CN | 58-167599 | 10/1983 |
| CN | 58-174322 | 10/1983 |
| DE | 2034785 | 1/1972 |
| DE | 2213180 | 9/1972 |
| DE | 2317770 | 10/1973 |
| DE | 26 21 470 A | 12/1977 |
| EP | 0066918 A1 | 12/1982 |
| EP | 0139358 A2 | 5/1985 |
| EP | 0161128 A1 | 11/1985 |
| EP | 0181129 A2 | 5/1986 |
| EP | 0222330 A2 | 5/1987 |
| EP | 0232813 A2 | 8/1987 |
| EP | 0277917 A2 | 8/1988 |
| EP | 0423776 A2 | 4/1991 |
| EP | 0423777 A2 | 4/1991 |
| GB | 2199036 A | 6/1988 |
| GB | 2203149 A | 10/1988 |
| WO | WO86/00310 | 1/1986 |
| WO | WO88/03147 | 5/1988 |
| WO | WO88/03148 | 5/1988 |
| WO | WO91/13082 | 9/1991 |
| WO | WO92/05177 | 4/1992 |
| WO | WO93/14102 | 7/1993 |
| WO | WO94/02497 | 2/1994 |
| WO | WO94/17090 A | 8/1994 |
| WO | WO94/18215 | 8/1994 |
| WO | WO95/02604 | 1/1995 |
| WO | WO95/11904 | 5/1995 |
| WO | WO95/18817 | 7/1995 |
| WO | WO96/02553 A | 1/1996 |
| WO | WO9602543 A1 | 2/1996 |

OTHER PUBLICATIONS

Thomas H. Burkey, et al., "Adenosine inhibits fMLP–stimulated adherence and superoxide anion generation by human neutrophils at an early step in signal transduction," *Biochimica et Biophysica Acta*, 1175 (1993) pp. 312–318.

Peter T. Peachell, et al., "Inhibition by Adenosine of Histamine and Leukotriene Release from Human Basophils," *Biochemical Pharmacology*, vol. 38, No. 11, pp. 1717–1725, 1989.

Yutaka Kohno, et al., "Activation of $A_3$ Adenosine Receptors on Human Eosinophils Elevates Intracellular Calcium," *Blood*, vol. 88, No. 9 (Nov. 1), 1996: pp. 3569–3574.

Erno A. Van Schaick, et al., "Hemodynamic effects and histamine release elicited by the selective adenosine $A_3$ receptor agonist 2–Cl–IB–MECA in conscious rates," *European Journal of Pharmacology 308*, (1996) pp. 311–314.

Hiroshi Asako, et al., "Leukocyte Adherence in Rat Mesenteric Venules: Effects of Adenosine and Methotrexate," *Gastroenterology* 1993; 104: pp. 31–37.

Rochelle Hirschhorn, "Overview of Biochemical Abnormalities and Molecular Genetics of Adenosine Deaminase Deficiency," *Pediatric Research, Copyright ©1992 International Pediatric Research Foundation, Inc.*, vol. 33 (Suppl.), No. 1, 1993, pp. S35–S41.

Sanna Rosengren, et al., "Anti–Inflammatory Effects of an Adenosine Kinase Inhibitor," *The Journal of Immunology*, 1995, 154: pp. 5444–5451.

Paul G. Green, et al., "Purinergic regulation of bradykinin–induced plasma extravasation and adjuvant–induced arthritis in the rat," *Proc. Natl. Aca. Sci. USA*, vol. 88, pp. 4162–4165, May 1991.

Bruce N. Cronstein, et al., "The antiinflammatory Mechanism of Methotrexate," *J. Clin. Invest. ©The American Society for Clinical Investigation, Inc.*, vol. 92, Dec. 1993, pp. 2675–2682.

Keith M. Skubitz, et al., "Endogenous and Exogenous Adenosine Inhibity Granulocyte Aggregation Without Altering the Associated Rise in Intracellular Calcium Concentration," *Blood*, vol. 72, No. 1 (Jul.), 1988: pp. 29–33.

Johan Richter, "Effect of adenosine analogues and cAMP–raising agents on TNF–, GM–CSF–, and chemotactic peptide–induced degranulation in single adherent neutrophils," *Journal of Leukocyte Biology*, vol 51, Mar. 1992, pp. 270–275.

J. J. Baker, et al., "5'–Substituted–5'–Deoxy Nucleosides," *Tetrahedron*, vol. 30, pp. 2939–2942, Apr. 8, 1974.

Bruce N. Cronstein, et al., "The Antiinflammatory Effects of Methotrexate are Mediated by Adenosine," *Purine and Pyrimidine Metabolism in Man VIII*, Edited by A. Sahota and M. Taylor, Plenum Press, New York, 1995, pp. 411–416.

Bruce N. Cronstein, et al., "Adenosine Modulates the Generation of Superoxide Anion by Stimulated Human Neutrophils via Interaction with a Specific Cell Surface Receptor," *Annals of the New York Academy of Sciences*,—Adenosine Deaminase in Disorders of Purine Metabolism and in Immune Deficiency, vol. 451, 1985, pp. 290–301.

Bruce N. Cronstein, et al., "A New Physiological Function for Adenosine: Regulation of Superoxide Anion Production," *Transactions of the Association of American Physicians*, Ninety–Sixth Session Held at Washington, DC, Apr. 20, 30 and May 1, 2, 1093, vol. XCVI, pp. 384–391.

Bruce N. Cronstein, "Adenosine, an endogenous anti–inflammatory agent," *Journal of Applied Physiology*, Jan. 1994, vol. 76, No. 1, pp. 5–13.

Richard R. Schmidt, "Riburonsäurederivate zur gezielten Veränderung der Riobose," Liebigs Ann. Chem., 1974, pp. 1856–1863.

M. Mester and L. Mester, "Mode of Action of Some Oxidized Sugar Derivatives of Adenine on Pletelet Aggregation," *Path.–Biol.*, Dec. 1972, 20, suppl., pp. 11–14.

2-(PURIN-9-YL)-TETRAHYDROFURAN-3,4-DIOL DERIVATIVES

This application is a continuation of U.S. application Ser. No. 09/331,526 filed Aug. 20, 1999, now U.S. Pat. No. 6,426,337, which is a 371 filing of international application no. PCT/EP97/07197 filed on Dec. 22, 1997 which claims priority from GB 9626845.3 filed Dec. 24, 1996 in Great Britain, GB 9626852.9 filed Dec. 24, 1996 in Great Britain, GB 9626846.1 filed Dec. 24, 1996 in Great Britain, 9720536.3 filed Sep. 27, 1997 in Great Britain, and 9722730.0 filed Oct. 29, 1997.

This invention relates to new chemical compounds, processes for their preparation, pharmaceutical formulations containing them and their use in therapy.

Inflammation is a primary response to tissue injury or microbial invasion and is characterised by leukocyte adhesion to the endothelium, diapedesis and activation within the tissue. Leukocyte activation can result in the generation of toxic oxygen species (such as superoxide anion), and the release of granule products (such as peroxidases and proteases). Circulating leukocytes include neutrophils, eosinophils, basophils, monocytes and lymphocytes. Different forms of inflammation involve different types of infiltrating leukocytes, the particular profile being regulated by the profile of adhesion molecule, cytokine and chemotactic factor expression within the tissue.

The primary function of leukocytes is to defend the host from invading organisms such as bacteria and parasites. Once a tissue is injured or infected a series of events occurs which causes the local recruitment of leukocytes from the circulation into the affected tissue. Leukocyte recruitment is controlled to allow for the orderly destruction and phagocytosis of foreign or dead cells, followed by tissue repair and resolution of the inflammatory infiltrate. However in chronic inflammatory states, recruitment is often inappropriate, resolution is not adequately controlled and the inflammatory reaction causes tissue destruction.

There is evidence from both in vitro and in vivo studies to suggest that compounds active at the adenosine A2a receptor will have anti-inflammatory actions. The area has been reviewed by Cronstein (1994). Studies on isolated neutrophils show an A2 receptor-mediated inhibition of superoxide generation, degranulation, aggregation and adherence (Cronstein et al, 1983 and 1985; Burkey and Webster, 1993; Richter, 1992; Skubitz et al, 1988. When agents selective for the A2a receptor over the A2b receptor (eg CGS21680) have been used, the profile of inhibition appears consistent with an action on the A2a receptor subtype (Dianzani et al, 1994). Adenosine agonists may also down-regulate other classes of leucocytes (Elliot and Leonard, 1989; Peachell et al, 1989). Studies on whole animals have shown the anti-inflammatory effects of methotrexate to be mediated through adenosine and A2 receptor activation (Asako et al, 1993; Cronstein et al, 1993 and 1994). Adenosine itself, and compounds that raise circulating levels of adenosine also show anti-inflammatory effects in vivo (Green et al, 1991; Rosengren et al, 1995). In addition raised levels of circulating adenosine in man (as a result of adenosine deaminase deficiency) results in immunosuppression (Hirschorn, 1993).

Certain substituted 4'-carboxamido and 4'-thioamido adenosine derivatives which are useful for the treatment of inflammatory diseases are described in International Patent Application Nos. WO94/17090, WO96/02553, WO96/02543 (Glaxo Group). Substituted 4'-carboxamidoadenosine derivatives useful in the treatment of dementia are described in AU 8771946 (Hoechst Japan). Substituted 4'-hydroxymethyl adenosine derivatives which are useful for the treatment of gastrointestinal motility disorders are described in EP-A423776 and EP-A423777 (Searle). Substituted 4'-hydroxymethyl adenosine derivatives which are useful as platelet aggregation inhibitors are described in BE-768925 (Takeda). 4'-Hydroxymethyl adenosine derivatives and 4'-esters thereof which are useful as antihypertensive agents or have other cardiovascular activity are described in U.S. Pat. No. 4,663,313, EP 139358 and U.S. Pat. No. 4,767,747 (Warner Lambert), U.S. Pat. No. 4,985,409 (Nippon Zoki) and U.S. Pat. No. 5,043,325 (Whitby Research). 4-Hydroxymethyladenosine derivatives useful in the treatment of autoimmune disorders are described in U.S. Pat. No. 5,106,837 (Scripps Research Institute). 4'-Hydroxymethyladenosine derivatives useful as antiallergic agents are described in U.S. Pat. No. 4,704,381 (Boehringer Mannheim). Certain 4'-tetrazolylalkyl adenosine derivatives which are useful in the treatment of heart and circulatory disorders are generically described in DT-A-2621470 (Pharma-Waldhof). Other 4'-carboxamidoadenosine derivatives useful in the treatment of cardiovascular conditions are described in U.S. Pat. No. 5,219,840, GB 2203149 and GB 2199036 (Sandoz), WO94/02497 (US Dept. Health), U.S. Pat. No. 4,968,697 and EP 277917 (Ciba Geigy), U.S. Pat. No. 5,424,297 (Univ. Virginia) and EP 232813 (Warner Lambert).

Other 4'-carboxamidoadenosine derivatives lacking substitution on the purine ring in the 2-position are described in DT 2317770, DT 2213180, U.S. Pat. No. 4,167,565, U.S. Pat. No. 3,864,483 and U.S. Pat. No. 3,966,917 (Abbott Labs), DT 2034785 (Boehringer Mannheim), JP 58174322 and JP 58167599 (Tanabe Seiyaku), WO92/05177 and U.S. Pat. No. 5,364,862 (Rhone Poulenc Rorer), EP 66918 (Procter and Gamble), WO86/00310 (Nelson), EP 222330, U.S. Pat. No. 4,962,194, WO88/03147 and WO88/03148 (Warner Lambert) and U.S. Pat. No. 5,219,839, WO95/18817 and WO93/14102 (Lab UPSA). 4'-Hydroxymethyladenosine derivatives lacking substitution on the purine ring in the 2-position are described in WO95/11904 (Univ Florida).

4'-Substituted adenosine derivatives useful as adenosine kinase inhibitors are described in WO94/18215 (Gensia).

Other 4'-halomethyl, methyl, thioalkylmethyl or alkoxymethyl adenosine derivatives are described in EP 161128 and EP 181129 (Warner Lambert) and U.S. Pat. No. 3,983,104 (Schering). Other 4'-carboxamidoadenosine derivatives are described in U.S. Pat. No. 7,577,528 (NIH), WO91/13082 (Whitby Research) and WO95/02604 (US Dept Health).

Certain tetrazole containing deoxynucleotides which were found to lack anti-infective activity are described in Baker et al (1974) Tetrahedron 30, 2939–2942. Other tetrazole containing adenosine derivatives which show activity as platelet aggregation inhibitors are described in Mester and Mester (1972) Pathologie-Biologie, 20 (Suppl) 11–14.

Certain nitrile containing ribose derivatives are described in Schmidt et al (1974) Liebigs. Ann. Chem. 1856–1863.

We have now found a novel group of compounds with broad anti-inflammatory properties which inhibit leukocyte recruitment and activation and which are agonists of the adenosine 2a receptor. The compounds are therefore of potential therapeutic benefit in providing protection from leukocyte-induced tissue damage in diseases where leukocytes are implicated at the site of inflammation. The compounds of the invention may also represent a safer alternative to corticosteroids in the treatment of inflammatory diseases, whose uses may be limited by their side-effect profiles.

More particularly, the compounds of this invention may show an improved profile over known A2a-selective agonists in that they generally lack significant agonist activity at the human A3 receptor. Furthermore they may even possess A3 antagonist activity. This profile can be considered of benefit as A3 receptors are also found on leucocytes (eg eosinophil) and other inflammatory cells (eg mast cell) and activation of these receptors may have pro-inflammatory effects (Kohno et al, 1996; Van Schaick et al 1996). It is even considered that the bronchoconstrictor effects of adenosine in asthmatics may be mediated via the adenosine A3 receptor (Kohno et al, 1996).

Thus, according to the invention we provide compounds of formula I:

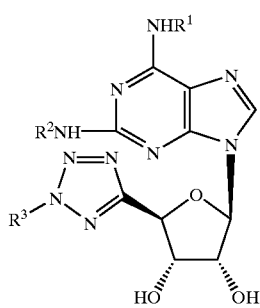 (I)

wherein $R^1$ and $R^2$ independently represent a group selected from:

(i) $C_{3-8}$cycloalkyl-;
(ii) hydrogen;
(iii) aryl$_2$CHCH$_2$—;
(iv) $C_{3-8}$cycloalkylC$_{1-6}$alkyl-;
(v) $C_{1-8}$alkyl-
(vi) arylC$_{1-6}$alkyl-;
(vii) $R^4R^5N$—C$_{1-6}$alkyl-;
(viii) $C_{1-6}$alkyl-CH(CH$_2$OH)—;
(ix) arylC$_{1-5}$alkyl-CH(CH$_2$OH)—;
(x) arylC$_{1-5}$alkyl-C(CH$_2$OH)$_2$—;
(xi) $C_{3-8}$cycloalkyl independently substituted by one or more —(CH$_2$)$_p$R$^6$ groups;
(xii) H$_2$NC(=NH)NHC$_{1-6}$alkyl-;
(xiii) a group of formula

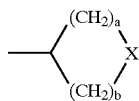

or such a group in which one methylene carbon atom adjacent to X, or both if such exist, is substituted by methyl;
(xiv) —C$_{1-6}$alkyl-OH;
(xv) —C$_{1-8}$haloalkyl;
(xvi) a group of formula

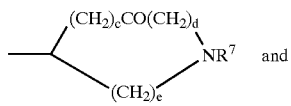 and (xvii) aryl;

$R^3$ represents methyl, ethyl or isopropyl;
$R^4$ and $R^5$ independently represent hydrogen, $C_{1-6}$alkyl, aryl, arylC$_{1-6}$alkyl- or NR$^4$R$^5$ together may represent pyrrolidinyl, piperidinyl, morpholinyl, azetidinyl, azepinyl, piperazinyl or N—C$_{1-6}$alkylpiperazinyl;
$R^6$ represents OH, NH$_2$ or halogen;
$R^7$ represents hydrogen, $C_{1-6}$alkyl or $C_{1-6}$alkylaryl;
X represents NR$^7$, O, S, SO or SO$_2$;
p represents 0 or 1;
a and b independently represent an integer 0 to 4 provided that a+b is in the range 3 to 5;
c, d and e independently represent an integer 0 to 3 provided that c+d+e is in the range 2 to 3;
and salts and solvates thereof.

References to $C_{1-6}$alkyl include references to an aliphatic hydrocarbon grouping containing 1 to 6 carbon atoms which may be straight chain or branched and may be saturated or unsaturated. References to $C_{1-4}$alkyl, $C_{1-5}$alkyl and $C_{1-8}$alkyl may be interpreted similarly.

References to aryl include references to mono- and bicyclic carbocyclic aromatic rings (e.g. phenyl, naphthyl) and heterocyclic aromatic rings containing 1–3 hetero atoms selected from N, O and S (e.g. pyridinyl, pyrimidinyl, thiophenyl, imidazolyl, quinolinyl, furanyl, pyrrolyl, oxazolyl) all of which may be optionally substituted, e.g. by $C_{1-6}$alkyl, halogen, hydroxy, nitro, $C_{1-6}$alkoxy, cyano, amino, SO$_2$NH$_2$ or —CH$_2$OH.

Examples of $C_{3-8}$cycloalkyl for $R^1$ and $R^2$ include monocyclic alkyl groups (e.g. cyclopentyl, cyclohexyl) and bicyclic alkyl groups (e.g. norbornyl such as exo-norborn-2-yl).

Examples of (aryl)$_2$CHCH$_2$— for $R^1$ and $R^2$ include Ph$_2$CHCH$_2$— or such a group in which one or both phenyl moieties is substituted, e.g. by halogen or $C_{1-4}$alkyl.

Examples of $C_{3-8}$cycloalkylC$_{1-6}$alkyl- for $R^1$ and $R^2$ include ethylcyclohexyl.

Examples of $C_{1-8}$alkyl for $R^1$ and $R^2$ include —(CH$_2$)$_2$C(Me)$_3$, —CH(Et)$_2$ and CH$_2$=C(Me)CH$_2$CH$_2$—.

Examples of arylC$_{1-6}$alkyl- for $R^1$ and $R^2$ include —(CH$_2$)$_2$Ph, —CH$_2$Ph or either in which Ph is substituted (one or more times) by halogen (e.g. iodine), amino, methoxy, hydroxy, —CH$_2$OH or SO$_2$NH$_2$; —(CH$_2$)$_2$ pyridinyl (e.g. —(CH$_2$)$_2$pyridin-2-yl) optionally substituted by amino; (CH$_2$)$_2$imidazolyl or this group in which imidazolyl is N-substituted by $C_{1-6}$alkyl (especially methyl).

Examples of $R^4R^5N$—C$_{1-6}$alkyl- for $R^1$ and $R^2$ include ethyl-piperidin-1-yl, ethyl-pyrrolidin-1-yl, ethyl-morpholin-1-yl, —(CH$_2$)$_2$N H(pyridin-2-yl) and —(CH$_2$)$_2$NH$_2$.

Examples of $C_{1-6}$alkyl-CH(CH$_2$OH)— for $R^1$ and $R^2$ include Me$_2$CHCH(CH$_2$OH)—.

Examples of arylC$_{1-5}$alkyl-CH(CH$_2$OH)— for $R^1$ and $R^2$ include PhCH$_2$CH(CH$_2$OH)— especially

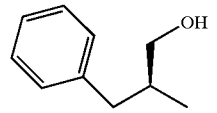

Examples of aryl $C_{1-5}$alkyl-C(CH$_2$OH)$_2$— for $R^1$ and $R^2$ include PhCH$_2$C(CH$_2$OH)$_2$—.

Examples of $C_{3-8}$ cycloalkyl independently substituted by one or more —(CH$_2$)$_p$R$^6$ groups (eg 1, 2 or 3 such groups) for $R^1$ and $R^2$ include 2-hydroxy-cyclopentyl and 4-aminocyclohexyl (especially trans-4-amino-cyclohexyl).

Examples of H$_2$NC(=NH)NHC$_{1-6}$alkyl for $R^1$ and $R^2$ include H$_2$NC(=NH)NH(CH$_2$)$_2$—

Examples of groups of formula

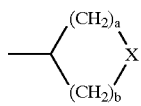

for $R^1$ and $R^2$ include pyrrolidin-3-yl, piperidin-3-yl, piperidin-4-yl or a derivative in which the ring nitrogen is substituted by $C_{1-6}$alkyl (e.g. methyl) or benzyl, tetrahydro-1,1-dioxide thiophen-3-yl, tetrahydropyran-4-yl, tetrahydrothiopyran-4-yl and 1,1-dioxo-hexahydro-1.lamda.6-thiopyran-4-yl.

Examples of $—C_{1-6}$alkyl-OH groups for $R^1$ and $R^2$ include $—CH_2CH_2OH$.

Examples of $C_{1-8}$haloalkyl for $R^1$ and $R^2$ include $—CH_2CH_2Cl$ and $(CH_3)_2ClC(CH_2)_3—$.

Examples of groups of formula

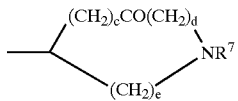

for $R^1$ and $R^2$ include 2-oxopyrrolidin-4-yl, 2-oxopyrrolidin-5-yl or a derivative in which the ring nitrogen is substituted by $C_{1-6}$alkyl (e.g. methyl) or benzyl.

Examples of aryl for $R^1$ and $R^2$ include phenyl optionally substituted by halogen (e.g. fluorine, especially 4-fluorine).

Examples of $C_{1-6}$alkyl for $R^7$ include methyl and $C_{1-6}$alkylaryl for $R^7$ include benzyl.

We prefer that $R^1$ and $R^2$ do not both represent hydrogen.

A preferred group of compounds are those compounds of formula I in which:

$R^1$ and $R^2$ independently represent a group selected from:
(i) $C_{3-8}$cycloalkyl-;
(ii) hydrogen;
(iii) $aryl_2CHCH_2—$;
(iv) $C_{3-8}$cycloalkyl$C_{1-6}$alkyl-;
(v) $C_{1-8}$alkyl-;
(vi) aryl$C_{1-6}$alkyl-;
(vii) $R^4R^5N—C_{1-6}$alkyl-;
(viii) $C_{1-6}$alkyl-$CH(CH_2OH)—$;
(ix) aryl$C_{1-5}$alkyl-$CH(CH_2OH)—$;
(x) aryl$C_{1-5}$alkyl-$C(CH_2OH)_2—$;
(xi) $C_{3-8}$cycloalkyl independently substituted by one or more (e.g. 1, 2 or 3) $—(CH_2)_pR^6$ groups;
(xii) $H_2NC(=NH)NHC_{1-6}$alkyl-;
(xiii) a group of formula

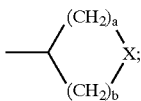

(xiv) a group of formula

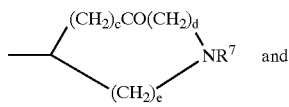

and (xv) aryl;

$R^4$ and $R^5$ independently represent hydrogen, $C_{1-6}$alkyl, aryl or $NR^4R^5$ together may represent pyrrolidinyl, piperidinyl, morpholinyl, azetidinyl, azepinyl, piperazinyl or N-methylpiperazinyl;

$R^6$ represents OH or $NH_2$;
X represents $NR^7$ or $SO_2$; and
a and b independently represent an integer 0 to 4 provided that a+b is in the range 3 to 4.

We prefer $R^1$ to represent $Ph_2CHCH_2—$, aryl$C_{1-6}$alkyl-, $C_{1-8}$alkyl-, aryl$C_{1-5}$alkyl $CH(CH_2OH)—$, $C_{3-8}$cycloalkyl, $C_{3-8}$cycloalkyl$C_{1-6}$alkyl-, $R^4R^5N—C_{1-6}$alkyl- or hydrogen.

We may also prefer $R^1$ to represent tetrahydropyran-4-yl, tetrahydrothiopyran-4-yl and 1,1-dioxo-hexahydro-1.lamda.6-thiopyran-4-yl.

We particularly prefer $R^1$ to represent $Ph_2CHCH_2—$, $PhCH_2—$, $(CH_3)_3C(CH_2)_2—$, $PhCH_2CH_2—$, aryl$CH_2—$ (especially wherein aryl represents optionally substituted phenyl, particularly phenyl or phenyl substituted by halogen most especially iodine in the meta position), $PhCH_2CH(CH_2OH)—$, cyclopentyl, $Et_2CH—$, $(cyclohexyl)(CH_2)_2—$, (pyrrolidin-1-yl)$(CH_2)_2—$, (morpholin-1-yl)$(CH_2)_2—$ or hydrogen.

We more particularly prefer $R^1$ to represent $Ph_2CHCH_2—$, $PhCH_2CH_2—$, $PhCH_2CH(CH_2OH)—$, cyclopentyl, $Et_2CH—$, $(CH_3)_3C(CH_2)_2—$, (cyclohexyl)$(CH_2)_2—$, and hydrogen.

We prefer $R^2$ to represent $R^4R^5NC_{1-6}$alkyl-, aryl, $C_{3-8}$cycloalkyl$C_{1-6}$alkyl-, $—C_{1-6}$alkyl-OH, aryl$C_{1-5}$alkylCH$(CH_2OH)—$, tetrahydro-1,1-dioxide thiophen-3-yl, $C_{3-8}$cycloalkyl, $H_2NC(=NH)NHC_{1-6}$alkyl-, $C_{3-8}$cycloalkyl independently substituted by one or more (e.g. 1, 2 or 3) $—(CH_2)_pR^6$ groups, $C_{1-6}$alkyl-$CH(CH_2OH)—$, aryl$C_{1-6}$alkyl- or pyrrolidin-3-yl, 2-oxopyrrolidin-4-yl, 2-oxopyrrolidin-5yl, piperidin-3-yl or piperidin-4-yl in which the ring nitrogen is optionally substituted by $C_{1-6}$alkyl or aryl $C_{1-6}$alkyl (e.g. benzyl).

We also prefer $R^2$ to represent tetrahydropyran-4-yl, tetrahydrothiopyran-4-yl and 1,1-dioxo-hexahydro-1.lamda.6-thiopyran-4-yl.

We particularly prefer $R^2$ to represent aryl (especially when aryl represents substituted phenyl, especially phenyl substituted in the para position by fluorine), (morpholin-1-yl)$(CH_2)_2—$, (pyrrolidin-1-yl)$(CH_2)_2—$, norbornyl, (cyclohexyl)$(CH_2)_2—$, $NH_2(CH_2)_2—$, $PhCH_2CH(CH_2OH)—$, cyclopentyl, $—(CH_2)_2OH$, pyrrolidin-3-yl, 2-hydroxy-cyclopentyl, $Me_2CHCH(CH_2OH)—$, tetrahydro-1,1-dioxide-thiophen-3-yl,N-benzyl-pyrrolidin-3-yl, 4-amino-cyclohexyl, (pyridin-2-yl)$NH(CH_2)_2$, $H_2NC(=NH)NH(CH_2)_2—$, aryl$(CH_2)_2—$ (especially wherein aryl represents substituted phenyl especially phenyl substituted in the para position by amino, $SO_2NH_2$, hydroxy or methoxy or in the meta and para position by hydroxy or methoxy or wherein aryl represents N-methyl imidazolyl or pyridinyl (especially pyridin-2-yl or pyridin-2-yl substituted in the meta position by amino)) or (3-$CH_2OH$)phenyl$(CH_2)$.

We also particularly prefer $R^2$ to represent (2-$CH_2OH$)phenyl$(CH_2)—$ or (piperidin-1-yl)$(CH_2)_2—$.

We more particularly prefer $R^2$ to represent 4-amino-cyclohexyl, (1-methyl-1H-imidazol-4-yl)-$CH_2CH_2—$, $PhCH_2CH(CH_2OH)—$, cyclopentyl, pyrrolidin-3-yl or (3-amino-pyridin-2-yl)$CH_2CH_2—$.

We prefer $R^3$ to represent methyl or ethyl, especially ethyl.

We prefer $R^4$ and $R^5$ independently to represent hydrogen, $C_{1-6}$alkyl or aryl or $NR^4R^5$ together to represent pyrrolidinyl, piperidinyl, morpholinyl, azetidinyl, azepinyl, piperazinyl or N-methylpiperazinyl;

We prefer X to represent $NR^7$, O, S or $SO_2$, particularly $NR^7$ or $SO_2$, especially $NR^7$.

We prefer that a and b both represent 2 or that a represents 1 and b represents 2.

We prefer that $R^7$ represents hydrogen.

We prefer that p represents 0.

We prefer that $R^6$ represents OH or $NH_2$ especially $NH_2$.

We prefer that c represents 0 and either d represents 2 and e represents 0 or d represents 1 and e represents 1.

A most particularly preferred set of compounds are those of formula (I) in which:

$R^3$ represents ethyl and (a) $R^1$ represents $CH_2CHPh_2$ and $R^2$ represents

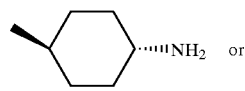 or

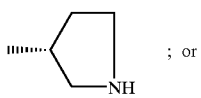 ; or (b) $R^1$ represents $CH_2CH_2Ph$ and $R^2$ represents

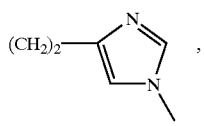,

A set of compounds that may also be mentioned are those of formula (I) in which $R^3$ represents ethyl, $R^1$ represents H and $R^2$ represents

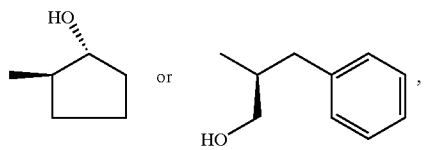,

A further most particularly preferred set of compounds are those of formula (I) in which $R^3$ represents ethyl, $R^1$ represents H and $R^2$ represents

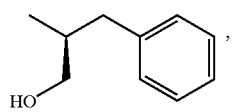,

The representation of formula (I) indicates the absolute stereochemistry at positions around the tetrahydrofuran ring. When sidechains contain chiral centres the invention extends to mixtures of enantiomers (including racemic mixtures) and diastereoisomers as well as to individual enantiomers. Generally it is preferred to use a compound of formula I in the form of a purified single enantiomer.

We also provide a process for preparation of compounds of formula I which comprises:

(a) reacting a corresponding compound of formula II

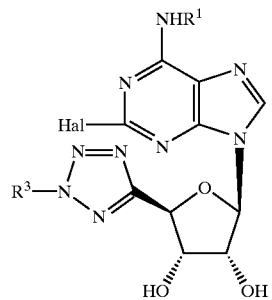

(II)

or a protected derivative thereof with a compound of formula $R^2NH_2$ or a protected derivative thereof;

(b) preparing a compound of formula (I) in which $R^1$ represents hydrogen by reducing a compound of formula III

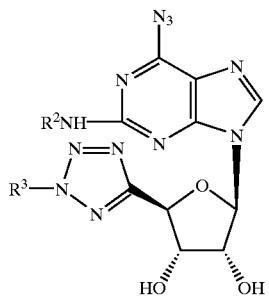

(III)

or a protected derivative thereof; or (c) deprotecting a compound of formula I which is protected; and where desired or necessary converting a compound of formula I or a salt thereof into another salt thereof.

In process (a) Hal represents a halogen eg chlorine or fluorine. The reaction of process (a) will generally be carried out on heating the reagents to a temperature of 50° C.–150° C. in the presence of a solvent such as DMSO. Preferably an organic base, e.g. a trisubstituted organic amine (such as diisopropylethylamine) is also present for the reaction. Under these conditions we particularly prefer that Hal represents fluorine (especially when $R^1$ represents hydrogen) since the reaction has a tendency to proceed rapidly with high efficiency.

In process (b) the reduction reaction may be performed by catalytic hydrogenation, e.g. over Pd/C under standard conditions.

In process (c) examples of protecting groups and the means for their removal can be found in T W Greene "Protective Groups in Organic Synthesis" (J Wiley and Sons, 1991). Suitable hydroxyl protecting groups include alkyl (e.g. methyl), acetal (e.g. acetonide) and acyl (e.g. acetyl or benzoyl) which may be removed by hydrolysis, and arylalkyl (e.g. benzyl) which may be removed by catalytic hydrogenolysis. Suitable amine protecting groups include sulphonyl (e.g. tosyl), acyl e.g. benzyloxycarbonyl or t-butoxycarbonyl) and arylalkyl (e.g. benzyl) which may be removed by hydrolysis or hydrogenolysis as appropriate.

Suitable salts of the compounds of formula (I) include physiologically acceptable salts such as acid addition salts derived from inorganic or organic acids, for example hydrochlorides, hydrobromides, 1-hydroxy-2-naphthoates, mesylates, sulphates, phosphates, acetates, benzoates, citrates, succinates, lactates, tartrates, fumarates and maleates, and if appropriate, inorganic base salts such as alkali metal salts, for example sodium salts. Other salts of the compounds of formula (I) include salts which may not be physiologically acceptable but may be useful in the preparation of compounds of formula (I) and physiologically acceptable salts thereof. Examples of such salts include trifluoroacetates and formates.

Examples of suitable solvates of the compounds of formula (I) include hydrates.

Acid-addition salts of compounds of formula I may be obtained by treating a free-base of formula I with an appropriate acid.

The compounds of formula II or a protected derivative thereof may be prepared by reacting a compound of IV

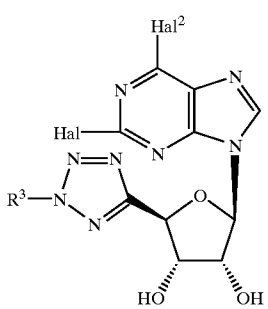

(IV)

or a protected derivative thereof with a compound of formula $R^1NH_2$. Hal and $Hal^2$ independently represent a halogen eg chlorine or fluorine. This reaction will preferably be performed in the presence of a base such as an organic amine base (e.g. diisopropyl ethylamine) in a solvate such as an alcohol (e.g. isopropanol) at elevated temperature (e.g. reflux).

Compounds of formula III or a protected derivative thereof may be prepared by reacting a compound of formula IIIA

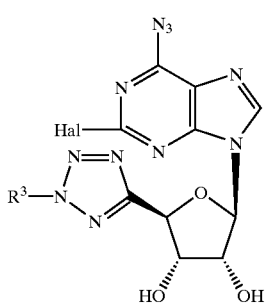

(IIIA)

wherein Hal represents a halogen eg chlorine or fluorine, or a protected derivative thereof, with a compound of formula $R^2NH_2$ under conventional conditions.

Compounds of formula IIIA, or a protected derivative thereof, may be prepared by reacting a compound of formula IV, or a protected derivative thereof, with an azide, e.g. sodium azide under conventional conditions.

The compound of formula IV or a protective derivative thereof may be prepared by reacting a compound of formula V

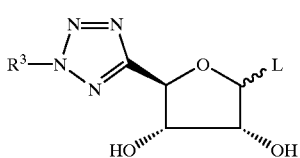

(V)

wherein L represents a leaving group or a protected derivative thereof with a 2,6,dihalopurine, e.g. 2,6-dichloropurine.

We prefer to use the compound of formula V wherein the ribose 2- and 3-hydroxyl groups are protected, e.g. by acetyl. Leaving group L may represent OH but will preferably represent $C_{1-6}$alkoxy (e.g. methoxy or ethoxy), an ester moiety (e.g. acetyloxy or benzoyloxy) or halogen. The preferred group L is acetyloxy. The reaction may be performed by combining the reactants in an inert solvent such as MeCN in the presence of a Lewis Acid (eg TMSOTf) and DBU and warming to, say, 70–80° C.

Compounds of formula V may be prepared from a compound of formula VI

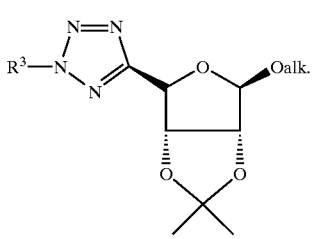

(VI)

Wherein alk represents $C_{1-6}$ alkyl eg methyl by treating the compound of formula VI with trifluoroacetic acid in water followed by reprotection, e.g. by reaction with acetic anhydride in pyridine.

Compounds of formula V in which L represents halogen, may be prepared from the corresponding 1'-alcohol or a 1'-ester such as the acetate. Reaction will generally occur on treatment with anhydrous HCl or HBr. 1'-iodides may be prepared directly on treatment with trimethylsilyliodide and 1'-fluorides may be prepared on treatment with DAST. An inert solvent eg diethylether, DCM, THF or $CCl_4$ will generally be suitable.

The compound of formula VI may be prepared following Scheme 1:

Scheme 1

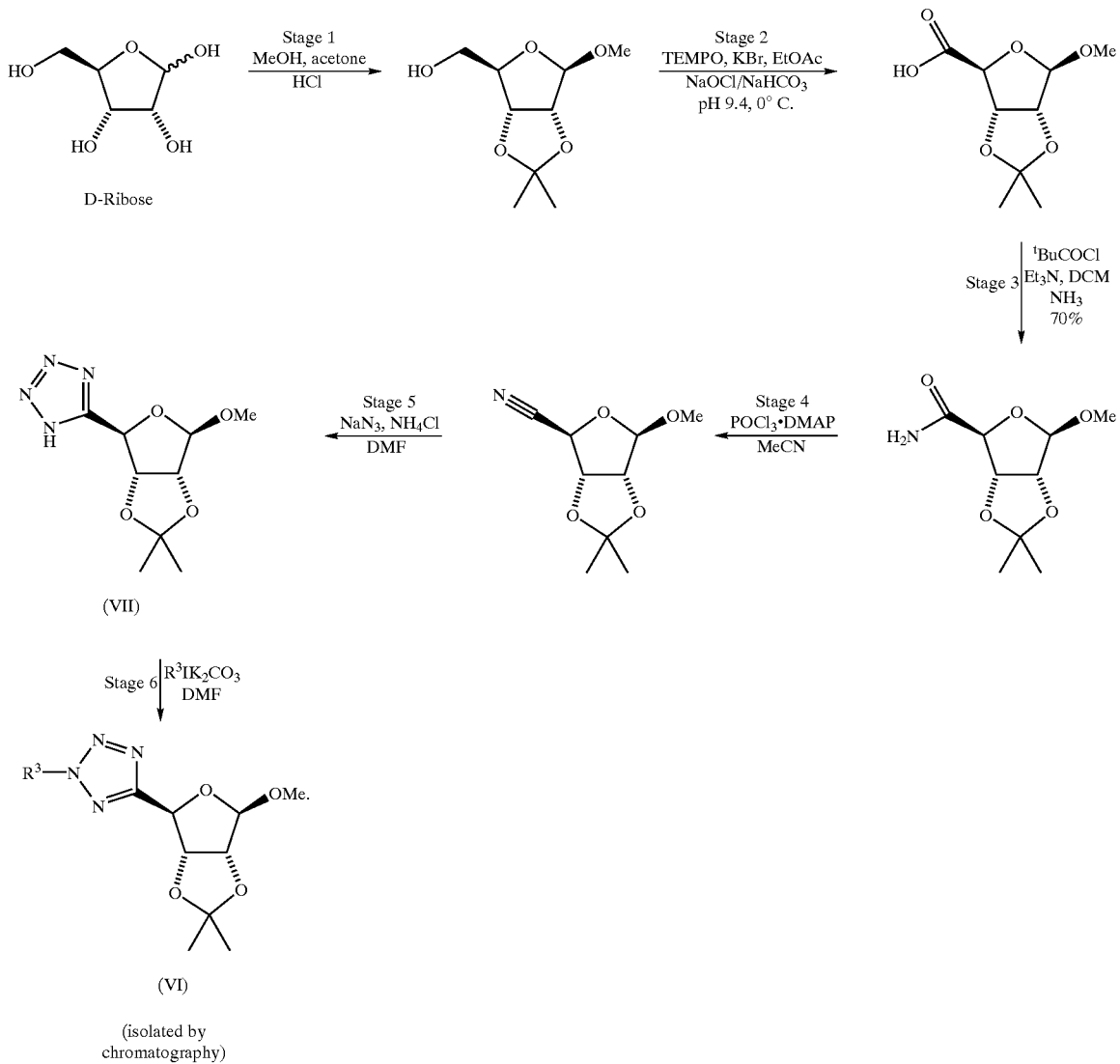

(VII)

(VI)

(isolated by chromatography)

General conditions for Stages 1–6 will be known to persons skilled in the art. It will also be appreciated that the reagents and conditions set out in Scheme 1 are example conditions and alternative reagents and conditions for achieving the same chemical transformation may be known to persons skilled in the art. For example an alternative alcohol, e.g. a $C_{1-6}$alkyl alcohol may be used in Stage 1 to give a different $C_{1-6}$ alkyloxy leaving group in compounds of formula VII and VI. Compounds of formula VII wherein a leaving group besides OMe is desired may be prepared by analogy with the method described above for preparation of compounds of formula V. Alternative groups may be used to protect the 2' and 3' hydroxy groups on the ribose in Stage 1. We have also found that Stage 5 may desirably be performed using azidotrimethylsilane and dibutyltin oxide in toluene.

Following stage 6, the impure product may be purified using conventional techniques, and especially using flash chromatography conditions under nitrogen pressure. We have found that satisfactory conditions include loading the impure product in a minimum volume of dichloromethane onto a Keiselgel 60 (Merck 9385) column and eluting using a gradient solvent system with ethyl acetate (10–40%) in cyclohexane.

Compounds of formula II, and protected derivatives thereof, may also be prepared by reacting a compound of formula V, or a protected derivative thereof with a compound of formula VIII

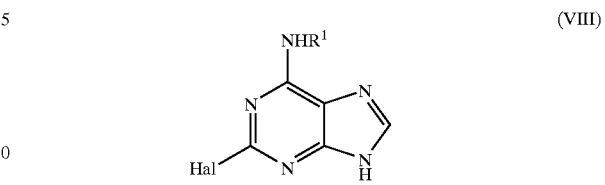

(VIII)

wherein Hal represents a halogen, e.g. chlorine or fluorine optionally followed by a deprotection or deprotection and reprotection reaction.

We prefer to use compounds of formula V in protected form. In particular we prefer that at least the hydroxy group in the 2-position on the ribose is protected as an ester group, e.g. by acetyl or benzoyl since this has a tendency to result in greater stereoselectivity in the coupling reaction. We prefer that the 2- and 3-position hydroxy groups are protected by acetyl. Suitable leaving groups L are a described previously. The preferred leaving group L is acetyloxy.

This process is particularly preferred when Hal represents fluorine (and most especially when $R^1$ represents hydrogen) since the reaction is generally fast and efficient and the reaction has a tendency to produce products of high crystallinity.

The product of this reaction may be deprotected if desired under conventional conditions eg on treatment with an alcohol (eg isopropanol) under mild basic conditions (eg in the presence of potassium carbonate)

The reaction of compounds of formula V (in protected form) and compounds of formula VIII may be performed in the presence of a Lewis Acid (eg TMSOTf) and optionally a silylating agent (eg BSA) in an inert solvent such as acetonitrile followed by work-up eg with water. When L represents halogen the Lewis Acid can generally be omitted when a silylating agent is present.

Certain compounds of formula VIII are known. Other compounds of formula VIII may be prepared by reaction of a compound of formula IX

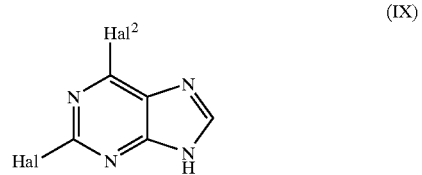

(IX)

wherein Hal and $Hal^2$ independently represent halogen, e.g. chlorine or fluorine, with $R^1 NH_2$ under conventional conditions.

Compounds of formula $R^1NH_2$, $R^2NH_2$ and IX are either known or may be prepared by conventional methods known per se.

The potential for compounds of formula (I) to inhibit leukocyte function may be demonstrated, for example, by their ability to inhibit superoxide ($O_2$—) generation from neutrophils stimulated with chemoattractants such as N-formylmethionyl-leucyl-phenylalanine (fMLP). Accordingly, compounds of formula (I) are of potential therapeutic benefit in providing protection from leukocyte-induced tissue damage in diseases where leukocytes are implicated at the site of inflammation.

Examples of disease states in which the compounds of the invention have potentially beneficial anti-inflammatory effects include diseases of the respiratory tract such as adult respiratory distress syndrome (ARDS), bronchitis (including chronic bronchitis), cystic fibrosis, asthma (including allergen-induced asthmatic reactions), chronic obstructive pulmonary disease (COPD), emphysema, rhinitis and septic shock. Other relevant disease states include diseases of the gastrointestinal tract such as intestinal inflammatory diseases including inflammatory bowel disease (e.g. Crohn's disease or ulcerative colitis), Helicobacter-pylori induced gastritis and intestinal inflammatory diseases secondary to radiation exposure or allergen exposure, and non-steroidal anti-inflammatory drug-induced gastropathy. Furthermore, compounds of the invention may be used to treat skin diseases such as psoriasis, allergic dermatitis and hypersensitivity reactions and diseases of the central nervous system which have an inflammatory component eg Alzheimer's disease and multiple sclerosis.

Further examples of disease states in which compounds of the invention have potentially beneficial effects include cardiac conditions such as peripheral vascular disease, post-ischaemic reperfusion injury and idiopathic hypereosinophilic syndrome.

Compounds of the invention which inhibit lymphocyte function may be useful as immunosuppressive agents and so have use in the treatment of auto-immune diseases such as rheumatoid arthritis and diabetes.

Compounds of the invention may also be useful in inhibiting metastasis.

Diseases of principal interest include asthma and COPD.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory agents.

There is thus provided as a further aspect of the invention a compound of formula (I) or a physiologically acceptable salt or solvate thereof for use in human or veterinary medicine, particularly in the treatment of patients with inflammatory conditions who are susceptible to leukocyte-induced tissue damage.

According to another aspect of the invention, there is provided the use of a compound of formula (I) or a physiologically acceptable salt or solvate thereof for the manufacture of a medicament for the treatment of patients with inflammatory conditions who are susceptible to leukocyte-induced tissue damage.

In a further or alternative aspect there is provided a method for the treatment of a human or animal subject with an inflammatory condition who is susceptible to leukocyte-induced tissue damage, which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in anti-inflammatory therapy, comprising a compound of formula (I) or a physiologically acceptable salt or solvate thereof together, if desirable, with one or more physiologically acceptable diluents or carriers.

There is also provided a process for preparing such a pharmaceutical formulation which comprises mixing the ingredients.

The compounds according to the invention may, for example, be formulated for oral, buccal, parenteral, topical or rectal administration, preferably for parenteral or topical (e.g. by aerosol) administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

By topical administration as used herein, we include administration by insufflation and inhalation. Examples of various types of preparation for topical administration include ointments, creams, lotions, powders, pessaries, sprays, aerosols, capsules or cartridges for use in an inhaler or insufflator, solutions for nebulisation or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetra-fluoroethane, 1,1,1,2,3,3,3-heptafluoropropane, 1,1,1,2-tetrafluoroethane, carbon dioxide or other suitable gas.

Intranasal sprays may be formulated with aqueous or non-aqueous vehicles with the addition of agents such as thickening agents, buffer salts or acid or alkali to adjust the pH, isotonicity adjusting agents or anti-oxidants.

Capsules and cartridges of for example gelatin, or blisters of for example laminated aluminium foil, for use in an inhaler or insufflator may be formulated containing a powder mix of a compound of the invention and a suitable powder base such as lactose or starch.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

The pharmaceutical compositions according to the invention may also be used in combination with other therapeutic agents, for example anti-inflammatory agents (such as corticosteroids (eg fluticasone propionate, beclomethasone dipropionate, mometasone furoate, triamcinolone acetonide or budesonide) or NSAIDs (eg sodium cromoglycate)) or beta adrenergic agents (such as salmeterol, salbutamol, formoterol, fenoterol or terbutaline and salts thereof) or antiinfective agents (eg antibiotics, antivirals).

The invention thus provides, in a further aspect, a combination comprising a compound of formula (I) or a physiologically acceptable salt or solvate thereof together with another therapeutically active agent, for example an anti-inflammatory agent such as a corticosteroid or NSAID.

The combination referred to above may conveniently be presented for use in the form of a pharmaceutical formulation and thus pharmaceutical formulations comprising a combination as defined above together with a physiologically acceptable diliuent or carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

Compounds of the invention may conveniently be administered in amounts of, for example, 0.01 to 500 mg/kg body weight, preferably 0.01 to 100 mg/kg body weight, 1 to 4 times daily. The precise dose will of course depend on the age and condition of the patient and the particular route of administration chosen.

The compounds of the invention have the advantage that they may be more efficacious, show greater selectivity, have fewer side effects, have a longer duration of action, be more bioavailable by the preferred route, show less systemic activity when administered by inhalation or have other more desirable properties than similar known compounds.

In particular the compounds of the invention have the advantage that they may show greater selectivity for the adenosine 2a receptor subtype over other adenosine receptor subtypes (especially the A1 and A3 receptor subtypes) than hitherto known compounds.

As a further aspect of the invention we provide certain compounds as new and useful intermediates.

Compounds of the invention were tested for in vitro and in vivo biological activity in accordance with the following screens:

(1) Agonist activity against adenosine 2a, adenosine 1 and adenosine 3 receptor subtypes.

Agonist selectivity of compounds against other human adenosine receptors was determined using Chinese hamster ovary (CHO) cells transfected with the gene for the relevant human adenosine receptor following a method based on that of Castanon and Spevak, 1994. The CHO cells were also transfected with cyclic AMP response elements promoting the gene for secreted placental alkaline phosphatase (SPAP) (Wood, 1995). The effect of test compounds was determined by their effects on basal levels of cAMP (A2a) or on forskolin-enhanced cAMP (A1 and A3) as reflected by changes in levels of SPAP. $EC_{50}$ values for compounds were then determined as a ratio to that of the non-selective agonist N-ethyl carboxamide adenosine (NECA).

(2) Antigen-induced lung eosinophil accumulation in sensitised guinea pigs.

Ovalbumin sensitised guinea pigs were dosed with mepyramine (1 mg/kg ip) to protect against anaphylactic bronchospasm. A compound of the invention was then given by the inhaled route (30 min breathing of an aerosol of the compound) immediately prior to ovalbumin challenge (30 min breathing of an aerosol generated from a 50 ug/ml solution of ovalbumin). Twenty four hours after challenge, the guinea pigs were killed and the lungs lavaged. Total and differential leucocyte counts were then obtained for the bronchoalveolar lavage fluid and the dose of test compound giving a 50% reduction in eosinophil accumulation ($ED_{50}$) was determined (Sanjar et al. 1992).

REFERENCES

Asako H, Wolf, R E, Granger, D N (1993), Gastroenterology 104, pp 31–37;
Burkey T H, Webster, R O, (1993), Biochem. Biophys Acta 1175, pp 312–318;
Castanon M J, Spevak W, (1994), Biochem. Biophys Res. Commun. 198, pp 626–631;
Cronstein B N, Kramer S B, Weissmann G, Hirschhorn R, (1983), Trans. Assoc. Am. Physicians 96, pp 384–91;
Cronstein B N, Kramer S B, Rosenstein E D, Weissmann G, Hirschhorn R, (1985), Ann N.Y. Acad. Sci. 451, pp 291–301;
Cronstein B N, Naime D, Ostad E, (1993), J. Clin. Invest. 92, pp 2675–82;
Cronstein B N, Naime D, Ostad E, (1994), Adv. Exp. Med. Biol., 370, pp 411–6;
Cronstein B N, (1994), J. Appl. Physiol. 76, pp 5–13;
Dianzani C, Brunelleschi S, Viano I, Fantozzi R, (1994), Eur. J. Pharmacol 263, pp 223–226;
Elliot K R F, Leonard E J, (1989), FEBS Letters 254, pp 94–98;
Green P G, Basbaum A I, Helms C, Levine J D, (1991), Proc. Natl. Acad Sci. 88, pp 4162–4165;
Hirschorn R, (1993), Pediatr. Res 33, pp S35–41;
Kohno Y; Xiao-duo J; Mawhorter S D; Koshiba M; Jacobson K A. (1996).Blood 88 p3569–3574.
Peachell P T, Lichtenstein L M, Schleimer R P, (1989), Biochem Pharmacol 38, pp 1717–1725;
Richter J, (1992), J. Leukocyte Biol. 51, pp 270–275;
Rosengren S, Bong G W, Firestein G S, (1995), J. Immunol. 154, pp 5444–5451;
Sanjar S, McCabe P J, Fattah D, Humbles M, Pole S M, (1992), Am. Rev. Respir. Dis. 145, A40;
Skubitz K M, Wickman N W, Hammerschmidt D E, (1988), Blood 72, pp 29–33
Van Schaick E A; Jacobson K A; Kim H O; Ijzerman A P; Danhof M. (1996) Eur J Pharmacol 308 p311–314.
Wood K V. (1995) Curr Opinion Biotechnology 6 p50–58.

The invention is illustrated by the following Examples:

EXAMPLES

General Experimental Details

Where products were purified by column chromatography, 'flash silica' refers to silica gel for chromatography, 0.040 to 0.063 mm mesh (e.g. Merck Art 9385), where column elution was accelerated by an applied pressure of nitrogen at up to 5 p.s.i. Where thin layer chromatography (TLC) has been used it refers to silica gel TLC using 5×10 cm silica gel 60 $F_{254}$ plates (e.g. Merck Art 5719).

Where products were purified by preparative HPLC, this was carried out on a C18-reverse-phase column (1" Dynamax), eluting with a gradient of acetonitrile (containing 0.1% trifluoroacetic acid) in water (containing 0.1% trifluoroacetic acid) and the compounds isolated as their trifluoroacetate salts unless otherwise specified.

Standard Automated Preparative HPLC Column,
Conditions & Eluent

Automated preparative high performance liquid chromatography (autoprep. HPLC) was carried out using a Supelco ABZ+5 μm 100 mm×22 mm i.d. column eluted with a mixture of solvents consisting of i) 0.1% formic acid in water and ii) 0.05% formic acid in acetonitrile, the eluent being expressed as the percentage of ii) in the solvent mixture, at a flow rate of 4 ml per minute. Unless otherwise stated the eluent was used as a gradient of 5–95 % over 20 minutes.

LC/MS System

The Liquid Chromatography Mass Spectroscopy (LC/MS) systems used:

LC/MS System A—A Supelco ABZ+, 3.3cm×4.6 mm i.d. column eluting with solvents: A—0.1% v/v formic acid+0.077% w/v ammonium acetate in water, and B—95:5 acetonitrile:water+0.05% v/v formic acid. The following gradient protocol was used: 100% A for 0.7 mins; A+B mixtures, gradient profile 0–100% B over 3.5 mins; hold at 100% B for 3.5 mins; return to 0% B over 0.3 mins. Positive and negative electrospray ionization was employed.

LC/MS System B—A Supelco ABZ+, 5 cm×2.1 mm i.d. column eluting with solvents: A—0.1% v/v formic acid+0.077% w/v ammonium acetate in water, and B—95:5 acetonitrile:water+0.05% v/v formic acid. The following gradient protocol was used: 0–100% B over 3.5 mins; hold at 100% B for 1.50 mins; return to 0% B over 0.50 mins. Positive and negative electrospray ionization was employed.

Intermediate 1

(3aS,4S,6R,6aR)-Methoxy-2,2-dimethyl-tetrahydro-furo[3,4-d][1,3]dioxole-4-carboxylic Acid A reaction vessel is charged with D-ribose (1 wt), and acetone (8 vol), 2,2-dimethoxypropane (2 vol), and perchloric acid ($HClO_4$, 0.4 vol). The reaction is stirred for 2–3 hours at ambient temperature. Methanol (1.4 vol) is added and the reaction is stirred for 2–3 hours. The reaction is cooled to 5–10° C. and neutralized with 30% sodium carbonate (2–3 vol). The resulting precipitant is filtered and the salt cake is washed with ethyl acetate (1 vol). The filtrate is concentrated in vacuo to ca. 4 residual volumes. Process water (4 vol) and ethyl acetate (8 vol) are added and the layers are separated following adequate mixing. The aqueous layer is then extracted with ethyl acetate (2×4 vol). The combined ethyl acetate layers are concentrated in vacuo to a residual ca. 4 volumes. The concentrate is reconstituted to 8 volumes with ethyl acetate. A reaction vessel is charged with the product of the previous step (6R-methoxy-2,2-dimethyl-tetrahydro-(3aR,6aR)-furo[3,4-d][1,3]dioxol-4R-yl)-methanol) (1 wt) in ethyl acetate (typical concentration 0.124 g/mL) and 6% sodium bicarbonate (3.5 vol). Potassium bromide (0.05wt) and 2,2,6,6-tetramethyl-1-piperidinyloxy (TEMPO, free radical, 0.0037 wt) are added and the solution is cooled to −5 to 0° C. Sodium bicarbonate (0.15 wt) is added to a solution of NaOCl (10–13%, 8.9 vol). The bleach solution is added at a rate that maintains the temperature ≦10° C. Upon completion of addition, cooling is removed and the reaction mixture is stirred for about 1–2 hours at ambient temperature. A 10% solution of sodium sulfite (2 vol) is then added to the reaction mixture and the layers are separated. The aqueous phase is adjusted to pH 2 with 4M HCl, followed by extraction with ethyl acetate (2×5 vol). The combined organic extracts are concentrated in vacuo to 2–3 vol, reconstituted with 8 volumes of cyclohexane and reconcentrated to 2–3 vol. The crystals are aged for at least one-half hour at 17–22° C., filtered and the cake is washed with cyclohexane (2 vol). The product is dried in vacuo for at least 18 hours at 45–50° C.

Melting point: 126–129° C.

Intermediate 1 (Alternative Process)

To a 1 L three neck round bottom flask equipped with an addition funnel, thermocouple probe and nitrogen inlet was added D-ribose (50 g) and acetone (400 mL). The mixture was cooled to −5° C. and then 2,2-dimethoxypropane (100 mL) followed by perchloric acid (20 mL) were added. The reaction mixture was allowed to warm to room temperature and then stirred for a brief period. Methanol (70 mL) was added and the reaction mixture was stirred overnight. The reaction solution was cooled to ca. 5° C. and ca. 95 mL of 30% sodium carbonate was added dropwise. The mixture was allowed to warm then filtered. The resulting cake was washed with ethyl acetate (50 mL). The filtrate was concentrated in vacuo at ca. 200 mbar until 250 mL of residual volume remained, diluted with ethyl acetate (200 mL) and reconcentrated to a residual volume of 170 mL. Ethyl acetate (200 mL) and water (200 mL) were added and the phases were mixed and separated. The aqueous phase was washed twice with ethyl acetate (200 mL) and the layers were separated. The combined organic extracts were concentrated to a residual volume of 200 mL and rediluted with ethyl acetate (200 mL) to provide an ethyl acetate solution of 6R-methoxy-2,2-dimethyl-tetrahydro-(3aR,6aR)-furo[3,4-d][1,3]dioxol-4R-yl)-methanol.

To a 2 L three neck round bottom flask was added the ethyl acetate solution of 6R-methoxy-2,2-dimethyl-tetrahydro-(3aR,6aR)-furo[3,4-d][1,3]dioxol-4R-yl)-methanol, 6% sodium bicarbonate (158 mL) potassium bromide (2.3 g), and TEMPO (0.167 g). The reaction mixture was cooled to −7° C. Meanwhile, sodium bicarbonate (6.8 g) was dissolved into 10–13% sodium hypochlorite (400.5 mL). The bleach solution was added dropwise over ca. 40 minutes, keeping the temperature below 15° C. The reaction mixture was stirred for ca. 2 hours and 10% aqueous sodium sulfite solution (47 mL) was added. The reaction mixture was stirred for 15 minutes, the phases separated and the aqueous phase adjusted to pH 2 with 4M HCl and extracted twice with ethyl acetate (225 mL). The ethyl acetate extracts were concentrated in vacuo to provide a white residue which was triturated with cyclohexane (90 mL). The solids were filtered and dried in vacuo at 45° C. to provide title product (33.6 g) (46% yield re D-ribose) as a white solid: m.p. 126–129° C.

Intermediate 2

(3aS,4S,6R,6aR)-6-Methoxy-2,2-dimethyl-tetrahydro-furo[3,4-d][1,3]dioxole-4-carboxylic Acid Amide A reaction vessel is charged with Intermediate 1 (1 wt), and ethyl acetate (8 vol). Thionyl chloride (0.47 vol, 1.4 eq) is added and the reaction mixture is warmed to 50–55° C. for 2–3 hours. The reaction mixture is cooled to 50° C. Anhydrous ammonia (0.8–1.2 wt, 10–15 eq) is slowly bubbled through the reaction mixture at such a rate that the temperature remains ≦60° C. The reaction is cooled to 15–20° C., process water (6 vol) is added and the layers are separated following adequate mixing. The aqueous layer is washed with ethyl acetate (2×4 vol). The combined organic extracts are concentrated in vacuo at 25–45° C. to a residual 3 volumes, reconstituted with 8 volumes of cyclohexane and reconcentrated to 3 vol. The product is stirred at 18–22° C. for one-half hour, filtered and the cake is washed with cyclohexane (2 vol). The product is dried in vacuo at 45–50° C. for at least 18 hours.

Melting point: 134–136° C. TLC (95/5 chloroform/methanol/~5 drops TFA per 50 mL/phosphomolybdic acid spray) rf=0.49.

Intermediate 2 (Alternative Process)

To a 500 mL three neck round bottom flask was added Intermediate 1 (20 g) and ethyl acetate (160 mL) followed by thionyl chloride (9.4 mL). The reaction solution was warmed at 50° C. for 2 hours. Gaseous ammonia (16 g) was added at such a rate that the temperature remains between 40–60° C. Water (120 mL) was added. The layers were separated and the aqueous layer was washed twice with ethyl acetate (80 mL). The combined organic washes were concentrated in vacuo to dryness. The residue was triturated with cyclohexane (40 mL) and the solids filtered. The cake was washed with cyclohexane (40 mL) and the solids dried in vacuo at 45° C. to provide the title product (16.7 g) (83.9% yield) as a light tan solid: m.p.=134–136° C.; TLC (95/5 chloroform/methanol/~5 drops TFA per 50 mL/phosphomolybdic acid spray) rf=0.49.

Intermediate 3

(3aS,4S,6R,6aR)-6-Methoxy-2,2-dimethyl-tetrahydro-furo[3,4-d][1,3]dioxole-4-carbonitrile A reactor vessel is purged with nitrogen and charged with Intermediate 2 (1 wt, 1 eq), ethyl acetate (12 vol), DMF (1.97 vol, 5.5 eq), and triethylamine (3.3 vol, 5.2 eq). The reaction mixture is cooled ca. 5° C. Phosphorusoxychloride (2.14 vol, 5 eq) is added at rate such that the bath temperature stays ≦40–45° C. The reaction is stirred for 1 hour. The reaction mixture is cooled to ca. 5° C. The organic layer is quenched with 20% potassium hydrogen carbonate (10 vol) and the layers are separated. The aqueous layer is washed with ethyl acetate (5 vol), the layers are separated. The combined organic extracts are backwashed with 20% potassium hydrogen carbonate (2×5 vol). The organic layer is concentrated to provide the title compound as as an oil.

TLC (1:1 Ethyl acetate/cyclohexane; phosphomolybdic acid development) rf=0.73.

Intermediate 3 (Alternative Process)

To a 22 L three neck round bottom flask was added Intermediate 2 (643 g), ethyl acetate (7.72 L), N,N-dimethylformamide (1.26 L), and triethylamine (2.15 L). The reaction solution was cooled to ca. 0° C. and of then phosphorus oxychloride (1.38 L) was added at such a rate that the temperature was maintained below 25° C. The reaction was stirred for one and one-half hours. Aqueous potassium hydrogen carbonate (20%, 6.5 L) was added dropwise maintaining the temperature at or below 20° C. The layers were separated and the aqueous layer re-extracted with ethyl acetate (3.5 L). The combined organic layers were washed twice with 20% potassium hydrogen carbonate (3.5 L) and concentrated to a residual volume of ca. 1 L. Activated carbon (15 grams) was added to the thin oil and the mixture was filtered through celite (80 g). The cake was washed with ethyl acetate (100 mL). The filtrate was concentrated in vacuo to provide title product (519 g) (88% yield) as a reddish-orange oil: TLC (1:1 Ethyl acetate/cyclohexane; phosphomolybdic acid reagent development) rf=0.73.

Intermediate 4

5-(6R-Methoxy-2,2-dimethyl-tetrahydro-(3aR,6aR)-furo[3,4-d][1,3]dioxol-4R-yl)-1H-tetrazole A reaction vessel is charged with Intermediate 3 (1 wt), toluene (10 vol), TMS azide (2.5 eq, 1.67 vol) and dibutyltin oxide (0.1 eq, 0.12 wt). The reaction mixture is warmed to 60° C. and stirred for 10 hours. The reaction mixture is distilled (to a residual 2–3 vol) removing both toluene and excess TMS azide. Toluene (3.5 vol) is added and the solution is reconcentrated to 2–3 vol. Water (1.1 eq, 0.05 vol) and toluene (2 vol) and the solution is stirred for 1–2 hours. The solution is concentrated to 2–3 volumes, toluene (3 vol) is added, and the solution is heated to ca 75° C. followed by slow cooling to ambient temperature and seeding with appropriate compound. The mixture is cooled to 0–5° C. and stirred for 2 hours. The product is filtered, washed with toluene (ca. 1.5 vol), and dried in vacuo to provide the title compound as a white to off-white crystalline solid. Melting point: 122–127° C.

Intermediate 4 (Alternative Process)

To a reaction vessel was added Intermediate 3 (26 g), N,N-dimethylformamide (650 mL) and ammonium chloride (14.5 g). The reaction mixture was cooled to 5° C. and sodium azide (17.2 g) was added portionwise over 5 minutes. The reaction mixture was heated at 40° C. for 1 hour and then slowly ramped to 90° C. over a 2 and one-half hour period. The reaction was stirred overnight at 90° C. then cooled to 5° C. Water (600 mL) was added followed by 6% sodium nitrite solution (216 mL) and then the mixture was stirred at 0° C. for 1 hour. The pH was adjusted to pH 1–3 with 2M sulfuric acid. The reaction mixture was extracted three times with ethyl acetate (1 L) and the combined organic layers were washed with saturated aqueous sodium chloride (1 L). The organic layer was dried over magnesium sulfate, filtered and concentrated to yield title product (31.85 g) (100% yield) as a yellow oil.

Intermediate 4 (Alternative Process)

To a 3 L three neck round bottom flask was added Intermediate 3 (200 g), toluene (2 L), azidotrimethylsilane (332 mL) and dibutyltin oxide (24.9 g). The reaction mixture was heated to 60° C. for 15 hours. The reaction mixture was concentrated in vacuo to a residual volume of ca. 300 mL. Toluene (1 L) was added and the solution was reconcentrated to a residual volume of ca. 470 mL. Toluene (400 mL) and water (19.8 mL) were added and the mixture was stirred at room temperature for approximately 2 hours. The mixture was concentrated to provide ca. 250 mL of residue. The residue was dissolved in toluene (800 mL) with warming then was allowed to cool to room temperature and was stirred for >3 days. The solids are filtered and washed twice with toluene (250 mL). The product was dried in vacuo to provide title product (135 g) (55% yield) as a white solid: mp 130° C.

Intermediate 5

2-Ethyl-5-(6R-methoxy-2,2-dimethyl-tetrahydro-(3aR,6aR)-furo[3,4-d][1,3]dioxol-4R-yl)-2H-tetrazole Ethyl iodide (1.3 eq) is added to a suspension of Intermediate 4 (1.0 eq) and potassium carbonate (1.3 eq) in acetone (7 vol) at ambient temperature. The resulting mixture is warmed to 40–45° C. and stirred for 3 to 4 hours. The reaction mixture is cooled to ambient temperature and diluted with cyclohexane (7 vol) then filtered to remove inorganics. The filtrate is concentrated to about 4 vol, then diluted with cyclohexane (7 vol) and crystallized at 0–5° C. for 18–48 hours. The crystallized material is removed by filtration, and the filtrate concentrated to an oil. The oil may require further recrystallisation from cyclohexane to bring the ratio of N2:N1 ethylated tetrazoles to approx. 94/6.

TLC $SiO_2$, (20% ethyl acetate in cyclohexane) Rf=0.21

Intermediate 5 (Alternative Process)

To a 1 L three neck round bottom flask was added Intermediate 4 (31.8 g), potassium carbonate (12.7 g) and acetone (238 mL). Ethyl iodide (14.1 mL) of was added via syringe and the reaction mixture was warmed at 42° C. for 2.5–3 hours. The reaction mixture was allowed to cool to room temperature and then cyclohexane (238 mL) was added. The resulting precipitate was filtered and the cake was washed three times with cyclohexane (65 mL). The filtrate was concentrated to a residual volume of 195 mL and then rediluted with cyclohexane (238 mL). The cyclohexane solution was cooled at 0–5° C. for 3 days and the resulting crystalline solid (N1 alkylation product) was filtered and washed three times with cyclohexane (65 mL). The combined filtrates was concentrated in vacuo to provide intermediate grade title product as an oil. The oil was dissolved in cyclohexane (200 mL) at 60° C. and the solution allowed to cool to room temperature and filtered. The resulting crystalline solid was filtered and washed three times with cyclohexane (65 mL). The combined filtrate was concentrated to provide title product as a yellow oil: TLC (1:1 Ethyl acetate/hexanes; phosphomolybdic acid reagent visualization) rf=0.68.

Intermediate 6 rel-Acetic Acid 4R,5-diacetoxy-2R-(2-ethyl-2H-tetrazol-5-yl)-tetrahydro-furan-3R-yl Ester A solution of Intermediate 5 (3.90 g, 14.4 mmol) in water (1 ml) and trifluoroacetic acid (9.5 ml) was stirred at 21° C. for 6 h. prior to concentration in vacuo. The residue was azeotroped several times with toluene to remove any residual moisture. The resultant colourless liquid was dissolved in pyridine (35 ml) and acetic anhydride (24 ml, 288 mmol) added. The reaction mixture was stirred at 21° C. for 20 h. prior to concentration in vacuo. This material was purified by column chromatography on flash silica eluting with 50% ethyl acetate in cyclohexane affording the title compound as an inseparable mixture of the α- and β-anomers as a clear gum (2.86 g).

TLC $SiO_2$, (50% ethyl acetate in cyclohexane) Rf=0.36

Intermediate 6 (Alternative Process)

To a round bottom flask was added Intermediate 5 (5.0 g). A solution of acetyl chloride (0.73 g) in methanol (50 mL) was added to the flask and the reaction solution was heated to reflux at 300 mbar pressure. The reaction was distilled over an 8–9 hour period and methanol (135 mL) was added portionwise during this time to replenish the reaction volume. The reaction mixture was allowed to cool to room temperature and pyridine (15 mL) was added. The mixture was concentrated in vacuo and rediluted with pyridine. Ethyl acetate (25 mL) and acetic anhydride (6.6 g) were added to the pyridine solution and the resulting mixture stirred overnight at room temperature. The reaction mixture was cooled to 5–10° C. and approximately 2M sulfuric acid (ca 45 mL) was added dropwise over 20 minutes while maintaining the temperature below 10° C. The layers were separated and the organic layer was washed with approximately 0.7M sulfuric acid (ca 25 mL). The organic layer was washed with sat. sodium bicarbonate and brine and then concentrated in vacuo to provide a pale yellow oil that was dissolved in 50 mL of ethyl acetate. Acetic anhydride (3.04 g) and of concentrated sulfuric acid (0.65 g) were added and the reaction mixture was warmed to 50° C. for ca. 3.5 hours. The reaction was quenched with saturated sodium bicarbonate solution (25 mL). The organic layer was concentrated in vacuo to provide title product ((5.1 g) (82% yield) as a yellow oil: TLC (1:1 Ethyl acetate/hexanes; phosphomolybdic acid reagent visualization) rf=0.44.

Intermediate 7

Acetic Acid, 4R-Acetoxy-2R-(2,6-dichloro-purin-9-yl)-5R-(2-ethyl-2H-tetrazol-5-yl)-tetrahydro-furan-3R-yl Ester To a mixture of Intermediate 6 (2.69 g, 7.86 mmol) and 2,6-dichloropurine (1.92 g, 10.2 mmol) in dry acetonitrile (34 ml) under nitrogen was added 1,8-diazobicylo[5.4.0] undec-7-ene (1.76 ml, 11.8 mmol) followed by dropwise addition of trimethylsilyl triflate (2.58 ml, 13.4 mmol). Mixture was stirred at 20° C. for 20 h. and then heated under reflux for 2 h. The cooled reaction was quenched with $H_2O$ (200 ml), extracted with ethyl acetate (3×200 ml), dried ($MgSO_4$). Removal of solvent gave a light brown gum which was purified by column chromatography on flash silica eluting with 30–50% ethyl acetate-cyclohexane to give the title compound as a white foam (3.26 g).

Mass spectrum m/z 471 ($MH^+$ for $C_{16}H_{16}{}^{35}Cl_2N_8O_5$).

Intermediate 8

Acetic Acid 4R-Acetoxy-2R-(2-chloro-6-(2,2-diphenylethylamino)-purin-9-yl)-5R-(2-ethyl-2H-tetrazol-5-yl)-tetrahydro-furan-3R-yl Ester 2,2-Diphenylethylamine (0.544 g, 2.76 mmol) was added to a stirring mixture of Intermediate 7 (1.00 g, 2.12 mmol) and di-isopropylethylamine (0.551 ml, 3.18 mmol) in isopropanol (33 ml) and heated at 50° C. for 20 h. Reaction mixture was evaporated in vacuo to a foam, which was purified by column chromatography on flash silica eluting with 30% ethyl acetate-cyclohexane furnishing the title compound as a white foam (1.39 g)

Mass spectrum m/z 632 ($MH^+$ for $C_{30}H_{30}{}^{35}ClN_9O_5$).

Intermediate 9

(2R,3R,4S,5R)-2-[2-Chloro-6-(2,2-diphenyl-ethylamino)-purin-9-yl]-5-(2-ethyl-2H-tetrazol-5-yl)-tetrahydro-furan-3,4-diol Intermediate 8 (0.660 g) was dissolved in anhydrous methanol (4 ml) and treated with sodium methoxide (25% weight in methanol; 0.043 ml) and the mixture was left to stir at 21° C. for 16 h. Ion exchange resin (Amberlite $H^+$ form, IR-120; 0.600 g) was washed with methanol and added to the mixture. The mixture was stirred at 21° C. for 5 min. The resin was filtered off and washed with methanol. The filtrate was evaporated in vacuo to give the title compound as a white solid (0.496 g). LC-MS m/z 548 ($MH^+$ for $C_{26}H_{30}N_{10}O_3$).

Intermediate 10

(2R,3R,4S,5R)-2-[6-(2,2-Diphenyl-ethylamino)-2-(pyrrolidin-3R-ylamino)-purin-9-yl]-5-(2-ethyl-2H-tetrazol-5-yl)-tetrahydro-furan-3,4-diol A mixture of Intermediate 9 (0.981 g), pyrrolidin-3R-ylamine (1.54 g) in dimethylsulphoxide (5 ml) was heated at 100° C. for 18 h. The cooled mixture was partitioned between ethyl acetate (250 ml) and water (250 ml). The aqueous layer was extracted with ethyl acetate (2×250 ml). The combined organic extracts were washed with water (250 ml), dried ($MgSO_4$) and evaporated in vacuo leaving an orange oil. This material was purified by column chromatography on flash silica eluting with dichloromethane-ethanol-880ammonia (100:8:1) affording the title compound as a colourless oil. (0.736 g).

LC-MS m/z 598 ($MH^+$ for $C_{30}H_{35}N_{11}O_3$).

Intermediate 11

Acetic Acid 4R-Acetoxy-2R-(2-chloro-6-phenethylamino-purin-9-yl)-5R-(2-ethyl-2H-tetrazol-5-yl)-tetrahydro-furan-3R-yl Ester A mixture of Intermediate 7 (2.20 g, 4.67 mmoles), diisopropylethylamine (1.2 ml, 7.01 mmoles) and 2-phenylethylamine (0.586 ml, 6.07 mmoles) in propan-2-ol (70 ml) under nitrogen was heated under reflux for 20 h. The solvent was removed in vacuo and the residue was purified by column chromatography on flash silica eluting with ethyl acetate:cyclohexane ((1:1), (3:1), (4:1)) to give the title compound as a white foam (2.26 g).

TLC $SiO_2$ (ethyl acetate:cyclohexane (1:1)) Rf=0.32 MS m/z 556 ($MH^+$) for $C_{24}H_{20}{}^{35}ClN_9O_5$).

Intermediate 12

(2R,3R,4S,5R)-2-(6-Amino-2-chloro-purin-9-yl)-5-(2-ethyl-2H-tetrazol-5-yl)-tetrahydro-furan-3,4-diol A solution of Intermediate 7 (4.25 g, 9.02 mmoles) in anhydrous tetrahydrofuran (100 ml) was cooled to 4° C. and ammonia was bubbled through with stirring for 45 min. The heterogeneous mixture was allowed to warm to 20° C. and stirred for 24 h. The mixture-was then recooled to 4° C. and ammonia bubbled through again for 45 min., and the reaction mixture again stirred for 24 h. at 20° C. The solvent was then removed in vacuo, and the residue treated with anhydrous methanol (250 ml) followed by sodium methoxide (0.9 ml of a 0.5M solution in methanol). After stirring for 1 h. under nitrogen at 20° C., further sodium methoxide (0.9 ml of 25% wt/wt solution in methanol) was added and stirring continued for a further 3 h. The solvent was removed in vacuo and the residue was purified twice by column chromatography on flash silica eluting with methanol:dichloromethane ((1:19),(7:93)) to give the title compound as an off-white solid (3.2 g). MS m/z 368 ($MH^+$ for $C_{12}H_{14}{}^{35}ClN_9O_3$).

Intermediate 13

5-(6R-Methoxy-2,2-dimethyl-tetrahydro-(3aR,6aR)-furo[3,4-d][1,3]dioxol-4R-yl)-2-methyl-2H-tetrazole A solution of Intermediate 4 (10.08 g, 32.0 mmol) in anhydrous N,N-dimethylformamide (64 ml) was treated with potassium carbonate (5.30 g, 38.4 mmol) with stirring under nitrogen. Methyl iodide (3.00 ml, 47.9 mmol) was added and the resultant solution was stirred at 21° C. for 5 h. The reaction mixture was concentrated in vacuo, diluted with water (250 ml), extracted with ethyl acetate (2×200 ml, 2×100 ml), dried (MgSO$_4$) and concentrated in vacuo to afford a mixture of the N2:N1 isomers as a brown oil. The mixture was purified by column chromatography on flash silica eluting with 20%–25% ethyl acetate in cyclohexane affording the title compound; as a colourless oil (3.86 g).

TLC SiO$_2$, (25% ethyl acetate in cyclohexane) Rf=0.17.

Intermediate 14

Acetic Acid 4R,5S-Diacetoxy-2R-(2-methyl-2H-tetrazol-5-yl)-tetrahydro-furan-3R-yl Ester A solution of Intermediate 13 (3.86 g, 15.1 mmol) in water (0.7 ml) and trifluoroacetic acid (13 ml) was stirred at 21° C. for 5 h. prior to concentration in vacuo. The residue was azeotroped with toluene (×3) and the resultant residue was dissolved in dichloromethane (46 ml) and cooled to 0° C. To this solution under nitrogen was added 4-dimethylaminopyridine (0.55 g, 4.5 mmol), triethylamine (94.6 ml, 679.0 mmol) followed by acetic anhydride (28.5 ml, 302.0 mmol). The reaction mixture was allowed to warm to 21° C. and stirred for 4 days prior to concentration in vacuo and azeotroping with toluene (×3). The resultant mixture was purified by column chromatography on flash silica eluting (30–60%) ethyl acetate in cyclohexane affording the title compound as a clear gum (1.38 g). TLC SiO$_2$, (70% ethyl acetate in cyclohexane) Rf=0.71.

Intermediate 15

Acetic Acid 4R-Acetoxy-5-methoxy-2R-(2-methyl-2H-tetrazol-5-yl)-tetrahydro-furan-3R-yl Ester Intermediate 16

Acetic Acid 4R,5R-diacetoxy-2R-(2-methyl-2H-tetrazol-5-yl)-tetrahydro-furan-3R-yl Ester The impurities, Intermediate 15 (TLC SiO$_2$, (70% ethyl acetate in cyclohexane) Rf=0.66), and Intermediate 16, (TLC SiO$_2$, (70% ethyl acetate in cyclohexane) Rf=0.56) were obtained as an inseparable mixture as a clear gum (1.59 g) in the course of the final chromatography step described for Intermediate 14.

Intermediate 17

Acetic Acid 4R-Acetoxy-2R-(2,6-dichloro-purin-9-yl)-5R-(2-methyl-2H-tetrazol-5-yl)-tetrahydro-furan-3R-yl Ester To a combined mixture of Intermediate 14 and Intermediate 15 and Intermediate 16 (2.97 g, 9.04 mmol) and 2,6-dichloropurine (2.22 g, 11.8 mmol) in dry acetonitrile-(20 ml) under nitrogen was added 1,8-diazobicylo[5.4.0]undec-7-ene (2.11 g, 13.6 mmol) followed by dropwise addition of trimethylsilyl triflate (2.97 ml, 15.4 mmol). Mixture was stirred at 20° C. for 5 days and then heated under reflux for 4 h. The cooled reaction was quenched with saturated aqueous NaHCO$_3$ (20 ml), extracted with ethyl acetate (4×100 ml), dried (MgSO$_4$). Removal of solvent in vacuo furnished a light brown gum which was purified by column chromatography on flash silica eluting with 40–50% ethyl acetate-cyclohexane to give the title compound as a yellow foam (2.94 g).

TLC SiO$_2$, (50% ethyl acetate in cyclohexane) Rf=0.21.

Intermediate 18

2-Isopropyl-5-(6-methoxy-2,2-dimethyl-tetrahydro-furo[3,4-d][1,3]dioxol-4-yl)-2H-tetrazole A solution of Intermediate 4 (8 g, 33.0 mmol) in anhydrous N,N-dimethylformamide (12 ml) was treated with potassium carbonate. (5.48 g, 39.7 mmol) with stirring under nitrogen. 2-Iodopropane (4.96 ml, 49.6 mmol) was added and the resultant solution was stirred at 21° C. for 48 h. The reaction mixture was filtered and then concentrated in vacuo. The brown residue was purified by column chromatography on flash silica eluting with 16% ethyl acetate in cyclohexane giving the title compound as a colourless oil (6.4 g).

TLC SiO$_2$, (25% ethyl acetate in cyclohexane) Rf=0.38.

Intermediate 19

Acetic Acid 4R,5S-Diacetoxy-2R-(2-isopropyl-2H-tetrazol-5-yl)-tetrahydro-furan-3R-yl Ester A solution of Intermediate 18 (6.00 g, 21.0 mmol) in water (1.4 ml) and trifluoroacetic acid (20.5 ml) was stirred at 21° C. for 6 h. prior to concentration in vacuo. The residue was azeotroped with toluene (×3). The resultant residue was dissolved in pyridine (50 ml) and acetic anhydride (35 ml) was added at 0° C. and left to stir for 12 h. at 20° C. The reaction mixture was concentrated in vacuo leaving a brownish oil. This material was purified by column chromatography on flash silica eluting with 25% ethyl acetate in cyclohexane affording the title compound as a clear gum (1.25 g)

TLC SiO$_2$, (25% ethyl acetate in cyclohexane) Rf=0.19.

Intermediate 20

Acetic Acid 4R-Acetoxy-2R-(2,6-dichloro-purin-9-yl)-5R-(2-isopropyl-2H-tetrazol-5-yl)-tetrahydro-furan-3R-yl Ester To a mixture of Intermediate 19 (1.20 g, 3.4 mmol) and 2,6-dichloropurine (0.83 g, 4.4 mmol) in dry acetonitrile (15 ml) under nitrogen was added 1,8-diazobicylo[5.4.0]undec-7-ene (0.76 ml, 5.1 mmol) followed by dropwise addition of trimethylsilyl triflate (1.10 ml, 5.78 mmol). Mixture was stirred at 20° C. for 16 h. and then heated under reflux for 3 h. The cooled reaction evaporated to dryness leaving a light brown gum which was purified by column chromatography on flash silica eluting with 50% ethyl acetate-cyclohexane to afford the title compound as a yellow foam (1.58 g).

TLC SiO$_2$, (50% ethyl acetate in cyclohexane) Rf=0.40.

Intermediate 21

2-[N,N-Bis(Trimethylsilyl)amine]-6-methylpyridine

To a solution of 2-amino-6-picoline (17.30 g, 160 mmol) in anhydrous tetrahydrofuran (130 ml) under nitrogen was added n-butyl lithium (1.6M in hexanes, 250 ml, 400 mmol) at −20 to −30° C. dropwise over 1 h. with stirring. The mixture was stirred at −8 to −10° C. for 30 min. whence chlorotrimethylsilane (50.7 ml, 400 mmol) was added at −25 to −5° C. over 40 min. The resultant mixture was allowed to warm to 20° C. and stirred for 16 h., before filtering through a pad of Keiselgel 60 (Merck 9385, 50 g), washed with tetrahydrofuran. The combined filtrate was concentrated in vacuo and the residual oil was distilled under vacuum. The title compound was obtained as a pale yellowish oil at 10 mbar in the boiling range 106–114° C.

TLC $SiO_2$, (25% cyclohexane in ethyl acetate) Rf=0.70.

Intermediate 22

2-(Ethylacetate)-6-aminopyridine

A solution of n-butyl lithium (1.6M in hexanes, 50 ml, 79.2 mmol) was added dropwise to a solution of Intermediate 21 (10.0 g, 39.6 mmol) in anhydrous tetrahydrofuran (30 ml) under nitrogen at −30 to −40° C. over 30 min. before stirring the reaction mixture for 30 min. at 20° C. The resultant mixture was added portionwise to solid carbon dioxide (pellets, 100 g) with stirring. The stirring was continued until a temperature of 20° C. was obtained whereupon the solvent was removed in vacuo. To the residue was added ethanol (100 ml) followed by the slow addition at −5 to −10° C. of anhydrous hydrochloric acid (30%) in ethanol (66 ml). Further hydrogen chloride gas was bubbled through the reaction mixture for 30 min. at 0–5° C. and the resultant solution was stirred at 15° C. for 16 h. Solvent was removed under reduced pressure, the residue dissolved in water (200 ml), washed with ethyl acetate (3×200 ml). The pH of the aqueous phase was adjusted to pH 7 with the addition of $NaHCO_3$ and extracted with ethyl acetate (6×100 ml). The combined extracts were washed with brine (200 ml), dried over $MgSO_4$ and solvent was removed in vacuo. The impure residue was was purified by column chromatography on flash silica eluting with 20% cyclohexane in ethyl acetate affording the title compound as a pale yellow solid (2.10 g).

TLC $SiO_2$, (25% cyclohexane in ethyl acetate) Rf=0.36.

Intermediate 23

2-(Acetamide)-6-aminopyridine

Intermediate 22 (0.800 g, 4.43 mmol was dissolved in methanol (5 ml) saturated with ammonia and stirred at 20° C. for 5 days. The reaction mixture was heated at 40° C. for 2 days and solvent was removed in vacuo leaving a brown solid. The residue was dissolved in methanol (5 ml) and liquid ammonia (20 ml) was added. The reaction mixture was contained within a pressure vessel gradually warming to 20° C. over 4 h. The solution was allowed to evaporate in the open atmosphere before concentrating in vacuo. The residue was purified by column chromatography on flash silica eluting with 5% methanol in dichloromethane affording the title compound as a pale cream solid (0.371 g).

Mass spectrum m/z 151.9 ($MH^+$ for $C_7H_{10}N_3O$).

Intermediate 24

2-(2-Aminoethyl)-6-aminopyridine

Intermediate 23 (0.350 g, 2.32 mmol) was added portionwise to a solution of lithium aluminium hydride in tetrahydrofuran (5.8 ml, 5.79 mmol) under nitrogen at 20° C. and stirred at 20° C. for 24 h. Aqueous sodium hydroxide solution (1M) was added until effervesence had ceased, the precipitate was filtered, washed with tetrahydrofuran. The filtrate was dried over $MgSO_4$ and concentrated in vacuo affording the title compound as a yellow oil (0.272 g).

TLC $SiO_2$, (25% methanol in dichloromethane) Rf=0.08.

Intermediate 25

Acetic Acid 4R-Acetoxy-2R-(6-amino-2-fluoro-purin-9-yl)-5R-(2-ethyl-2H-tetrazol-5-yl)-tetrahydrofuran-3 R-yl Ester To a round bottom flask equipped with an addition funnel was added 2-fluoroadenine (12 g) and anhydrous acetonitrile (240 mL). Bistrimethylsilylacetamide (57.9 mL) was added dropwise over 3 minutes and the resulting suspension heated for 1 hour and 45 minutes. The solution was cooled to room temperature and Intermediate 6 (ca. 27 g) in acetonitrile (70 mL) was added via syringe followed by the addition of 17 mL of TMS triflate (17 mL). The reaction mixture was heated at reflux for 6 hours, then allowed to cool to room temperature. The reaction mixture was concentrated in vacuo and the resultant oil was dissolved in methylene chloride (200 mL) and poured over ice water (ca 150 mL). The layers were separated and the aqueous layer was extracted twice with methylene chloride (150 mL). The combined organic extracts were washed with water (200 mL) and brine (250 mL), dried over sodium sulfate (33 g) and concentrated in vacuo to provide intermediate grade title product as a yellow solid. Ethanol (100 mL) was added to the solid and the suspension was heated to 50° C. The mixture was cooled in an ice/water bath for 1 hour and then filtered. The resultant product was dried in vacuo at 50° C. for 3 days to provide title product (23.4 g) (67% yield) as an off white powder: m.p. 208–210° C.; TLC (90:10 methylene chloride/methanol) rf=0.53.

Intermediate 26

(2R,3R,4S,5R)-2-(6-Amino-2-fluoro-purin-9-yl)-5-(2-ethyl-2H-tetrazol-5-yl)-tetrahydrofuran-3,4-diol To a round bottom flask was added Intermediate 25 (3.0 g) in isopropyl alcohol (23 mL), water (4.9 mL) and potassium carbonate (1.91 g). The white suspension was stirred at room temperature for 3 and one-half days and was then diluted with ethyl acetate (50 mL). The reaction mixture was poured onto water (40 mL) and the aqueous phase extracted four times with ethyl acetate (30 mL). The combined organic extracts were washed with brine (40 ml) and concentrated in vacuo to provide title product (2.42 g) (100% yield) as a white solid: TLC (90:10 methylene chloride/methanol then 1:1 hexanes/ethyl acetate) rf=0.50.

Intermediate 27

2-(Pyridin-2-ylamino)-ethylamine

2-Bromopyridine (10.00 g, 63.3 mmol) was added dropwise to 1,2-diaminoethane (76.00 g, 126.6 mmol) under nitrogen at 20° C. with stirring. The reaction mixture was stirred at 20° C. for 4 h. and then under reflux for 24 h. The reaction mixture was concentrated in vacuo and purified by column chromatography on flash silica eluting with dichloromethane, ethanol and ammonia (30:8:1) to afford the title compound as a red oil (1.23 g).

TLC $SiO_2$, (Dichloromethane, ethanol, ammonia; 30:8:1) Rf=0.14 Mass Spectrum m/z 138 ($MH^+$ for $C_7H_{11}N_3$).

Intermediate 28

4R-Acetoxy-2R-[2-chloro-6-(3,3-dimethyl-butylamino)-purin-9-yl]-5R-(2-ethyl-2H-tetrazol-5-yl)-tetrahydro-furan-3R-yl Ester Intermediate 7 (0.188 g, 0.40 mmol), 3,3-dimethylbutylamine (0.040 g, 0.40 mmol) and diisopropylethylamine (0.052 g, 0.40 mmol) in isopropanol (12 ml) was stirred at 20° C. for 16 h. The solvent was removed in vacuo leaving the title compound as a coloured solid (0.214 g).

LC/MS SYSTEM A $R_t$=4.89 min. LC/MS SYSTEM A m/z 536 ($MH^+$).

Intermediate 29

2-Hydroxymethylbenzylamine

Lithium aluminium hydride (12.4 ml, 1.0M in diethyl ether) was added cautiously to 2-cyanomethylbenzoate (1.00 g, 6.2 mmol) in anhydrous diethyl ether (40 ml) under nitrogen with stirring over 10 min. whilst ensuring the temperature was not greater than 15–25° C. using an ice bath. After the addition was complete the reaction mixture was allowed to warm to 21 C and then heated at reflux for 16 h. The reaction mixture was cooled to approximately −10 C. It was treated cautiously dropwise with water (0.5 ml), 20% aqueous sodium hydroxide (0.37 ml) and water (1.74 ml). The resultant green heterogeous mixture was filtered and the residue was with diethyl ether (150 ml), the combined washings and filtrate were dried ($MgSO_4$) and solvent was removed in vacuo affording the title compound as a green oil (0.807 g). Mass Spectrum m/z 138 ($MH^+$ for $C_8H_{12}NO$).

Example 1 rel-(2R,3R,4S,5R)-2-[2-(trans-4-Amino-cyclohexylamino)-6-(2,2-diphenylethylamino)-purin-9-yl]-5-(2-ethyl-2H-tetrazol-5-yl)-tetrahydro-furan-3,4-diol A mixture of Intermediate 8 (0.942 g, 1.72 mmol) and trans 1,4-diaminocyclohexane (preparable following methods described in International Patent Application WO94/17090) (1.19 g, 10.3 mmol) in dry dimethylsulphoxide (5 ml) was heated at 120° C. for 60 h. The cooled reaction mixture was partitioned between ethyl acetate (100 ml) and brine (100 ml). Organic phase was separated, washed with a mixture of $H_2O$ and brine (1: 1, 100 ml). Combined aqueous solution was extracted with ethyl acetate (100 ml). Combined organic solution were dried over $MgSO_4$, filtered and evaporated in vacuo to afford an off-white gum (1.22 g), which was purified by column chromatography on flash silica eluting with $CH_2Cl_2$—MeOH-880 $NH_3$ (40:10:1) affording the free base product as a beige coloured solid (0.785 g). TLC $SiO_2$ ($CH_2Cl_2$:methanol:880 $NH_3$; 40:10:1)= Rf 0.36.

Example 1a rel-(2R,3R,4S,5R)-2-[2-(trans-4-Amino-cyclohexylamino)-6-(2,2-diphenyl-ethylamino)-purin-9-yl]-5-(2-ethyl-2H-tetrazol-5-yl)-tetrahydro-furan-3,4-diol Dihydrochloride Example 1 (freebase) (0.780 g, 1.25 mmol) was dissolved in a mixture of methanol (3 ml) and ethyl acetate (20 ml) and treated with hydrogen chloride in ether (1 M, 2.5 ml, 2.5 mmol)and white precipitate formed immediately. Ether (40 ml) was added to this heterogeneous mixture and stirred in open air for 18 h. at 20° C. White solid was filtered, washed with ether (3×10 ml), dried in vacuo to give the title compound as a white solid (0.84 g).

m.p. 141.2° C. (decomposes) LC-MS m/z 626 ($MH^+$ for $C_{32}H_{39}N_{11}O_3$). Analysis Found C, 53.35%; H, 6.35%; N, 21.03% $C_{32}H_{39}N_{11}O_3$2HCl, 1.4$H_2O$ C, 53.10%; H, 6.10%; N, 21.28%.

Example 1b rel-(2R,3R,4S,5R)-2-[2-(trans-4-Amino-cyclohexylamino)-6-(2,2-diphenyl-ethylamino)-purin-9-yl]-5-(2-ethyl-2H-tetrazol-5-yl)-tetrahydro-furan-3,4-diol Sulphate Example 1 (freebase) (0.305 g, 0.49 mmol) was dissolved in industrial methylated spirit (3 ml) and treated dropwise over 30 min. with industrial methylated spirit (2 ml) containing sulfuric acid (0.49 ml) and a white precipitate formed immediately. Industrial methylated spirit (1 ml) was added to this heterogeneous mixture and stirred for 24 h. at 20° C. White solid was filtered, washed with industrial methylated spirit (2 ml), and recrystallised from a mixture of methanol (60 ml), ethanol (10 ml) and iso-propanol (3 ml) furnishing the title compound as a white crystalline solid (0.263 g).

LC/MS SYSTEM A $R_t$=3.79 min; LC/MS SYSTEM A m/z 626 ($MH^+$).

Example 2

(2R,3R,4S,5R)-2-[6-(2,2-Diphenyl-ethylamino)-2-(pyrrolidin-3-ylamino)-purin-9-yl]-5-(2-ethyl-2H-tetrazol-5-yl)-tetrahydro-furan-3,4-diol tris (Trifluoroacetate)

Intermediate 9 (0.050 g, 0.091 mmol), 3-aminopyrolidine (0.040 g, 0.45 mmol) in n-butanol (0.5 ml) was heated at 130° C. for 28 h. The reaction mixture was diluted with methanol (10 ml), purified using preparative HPLC (20–70% acetonitrile) and solvent was removed in vacuo to yield the title compound as a brown solid (0.034 g) TLC $SiO_2$, (16% methanol in dichloromethane) Rf=0.12 MS Electrospray accurate mass; measured $MH^+$ at 598.301184, calculated for $C_{30}H_{36}N_{11}O_3$=598.300259.

Example 3

(2R,3S,4R,5R)-2-(2-Ethyl-2H-tetrazol-5-yl)-5-{6-(3-iodo-benzylamino)-2-[2-(1-methyl-1H-imidazol-4-yl)-ethylamino]-purin-9-yl}-tetrahydro-furan-3,4-diol Intermediate 7 (0.012 g, 0.025 mmol) was dissolved in isopropanol (0.25 ml), isopropanol (0.25 ml) containing di-isopropylethylamine (0.006 g, 0.025 mmol) was added, followed by the addition of 3-iodobenzylamine (0.002 g, 0.025 mmol) in isopropanol (0.25 ml). The mixture was left at 20° C. for 12 h. whereupon 1-methylhistamine (0.038 g, 0.30 mmol) in isopropanol (0.50 ml) was added and the solvent was blown off under a stream of nitrogen. The residual gum was suspended in dimethylsulfoxide (6 drops) and the mixture was heated at 120° C. for 4 days. Concurrently Intermediate 7 (0.012 g, 0.025 mmol) was dissolved in isopropanol (0.25 ml), isopropanol (0.25 ml) containing di-isopropylethylamine (0.006 g, 0.025 mmol) was added, followed by the addition of 3-iodobenzylamine (0.002 g, 0.025 mmol) in isopropanol (0.25 ml). The mixture was left at 20° C. for 12 h. whereupon sodium methoxide (0.001 g, 0.025 mmol) in isopropanol (0.25 ml) was added with dimethylsulfoxide (3 drops). After 6 h. at 20° C., 1-methylhistamine (0.038g, 0.30 mmol) in isopropanol (0.50 ml) was added and the solvent was blown off under a stream of nitrogen. The residual gum was suspended in dimethylsulfoxide (6 drops) and the mixture was heated at 120° C. for 4 days. The reaction mixtures form these two experiments were combined and purified using Solid Phase Extraction (SPE) chromatography ($NH_2$ aminopropyl Bondelute) cartridges, the residue was dissolved in dichloromethane (5 ml) and applied to 1 SPE cartridge (5 ml cartridge), the cartridge was sequentially washed with dichloromethane (5 ml), chloroform (5 ml), diethyl ether (5 ml), ethyl acetate (2×5 ml), actetonitrile (2×5 ml) and acetone (2×5 ml). The combined acetone fractions were concentrated in vacuo and submitted to further purification with the residue being dissolved in dichloromethane (1 ml)

and applied to 1 SPE cartridge (1 ml cartridge), the cartridge was sequentially washed with dichloromethane (1 ml), chloroform (1 ml), diethyl ether (1 ml), ethyl acetate (2×1 ml), acetonitrile (2×1 ml) and acetone (2×1 ml). The combined acetone fractions were concentrated in vacuo affording the title compound as a white solid (0.008 g).

LC/MS SYSTEM A $R_t$=3.62 min; LC/MS SYSTEM A m/z 673 (MH$^+$).

Example 4

(2R,3S,4R,5R)-2-(2-Ethyl-2H-tetrazol-5-yl)-5-{2-[2-(1-methyl-1H-imidazol-4-yl)-ethylamino]-6-phenethylamino-purin-9-yl}-tetrahydro-furan-3,4-diol Dihydrochloride

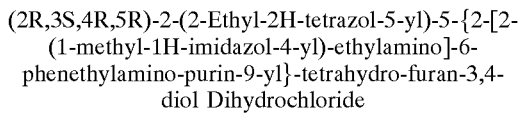

A solution of sodium hydroxide (2.52 g, 63.0mmoles) in methanol (90 ml) was treated with 1-methylhistamine bishydrochloride (6.50 g, 32.5 mmoles), and stirred at 20° C. for 15 min. The solution was reduced to one quarter volume in vacuo, treated with Intermediate 11 (2.26 g, 4.07 mmoles), and the heterogeneous mixture was stirred at 20° C. for 30 min. The solvent was removed by nitrogen flow to leave a residue which was dissolved in dimethylsulphoxide (2.0 ml), then heated at 115° C. for 24 h. and allowed to cool. The mixture was partitioned between dichloromethane (300 ml) and water (30 ml). The organic phase was washed with water (30 ml), dilute aqueous sodium chloride (50 ml), then dried (MgSO$_4$) and evaporated in vacuo to give an orange foam. This was purified by preparative h.p.l.c. (gradient profile 17–38% acetonitrile/water acidified with 0.1% acetic acid, Rt 12 min.) to give a beige solid. This was dissolved in a mixture of water (75 ml), 1,4-dioxan (2.5 ml), acetonitrile acidified with 0.1% acetic acid (50 ml) and methanol (20 ml), and freeze-dried to give a beige solid. This solid was dissolved in dichloromethane (200 ml), and the solution washed successively with saturated aqueous sodium hydrogen carbonate (3×30 ml) and water (30 ml), then dried (MgSO$_4$), and concentrated in vacuo to give a yellow foam. This was dissolved in methanol (15 ml), ethyl acetate (20 ml) and diethyl ether (20 ml), then treated with hydrogen chloride (6.1 ml of a 1M solution in diethyl ether). Diethyl ether (120 ml) was then added portionwise over 5 min., and the heterogeneous mixture stirred at 20° C. for 1 h. The resultant solid on the walls of the flask was scrapped loose, and the slurry stirred for a further 10 min. The supernatant was then removed, the solid treated with diethyl ether (250 ml), the mixture stirred for 15 min., then the supernatant was removed. The solid was treated again with diethyl ether (250 ml), stirred for 15 min., then the supernatant removed and the solid blown dry under nitrogen flow to give the title compound as an off-white powder (1.92 g).

Analysis Found: C, 46.5; H, 5.9; N, 23.9; C$_{26}$H$_{32}$N$_{12}$O$_3$2.0HCl.2.5H$_2$O.0.2 C$_4$H$_{10}$O requires C, 46.4; H, 6.0; N, 24.2% Mass spectrum m/z 561 (MH$^+$ for C$_{26}$H$_{32}$N$_{12}$O$_3$).

Example 5

(2R,3R,4S,5R)-2-{6-Benzylamino-2-[2-(1-methyl-1H-imidazol-4-yl)-ethylamino]-purin-9-yl}-5-(2-ethyl-2H-tetrazol-5-yl)-tetrahydro-furan-3,4-diol Example 5 was prepared in an analogous manner to Example 3 using benzylamine (0.003 g, 0.025 mmol). The title compound was afforded after evaporation of the solvent in vacuo as a white solid (0.005 g)

LC/MS SYSTEM A $R_t$=3.42 min; LC/MS SYSTEM A m/z 547 (MH$^+$).

Example 6

(2R,3R,4S,5R)-2-{6-(1-Ethyl-propylamino)-2-[2-(1-methyl-1H-imidazol-4-yl)-ethylamino]-purin-9-yl}-5-(2-ethyl-2H-tetrazol-5-yl)-tetrahydro-furan-3,4-diol Acetate

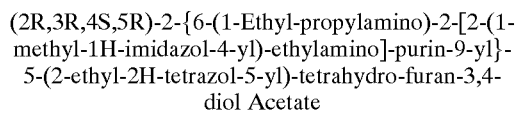

Intermediate 7 (0.012 g, 0.025 mmol) was dissolved in isopropanol (0.25 ml), isopropanol (0.25 ml) containing di-isopropylethylamine (0.006 g, 0.025 mmol) was added, followed by the addition of 3-pentylamine (0.002 g, 0.025 mmol) in isopropanol (0.25 ml). The mixture was left at 20° C. for 12 h. whereupon 1-methylhistamine (0.038 g, 0.30 mmol) in isopropanol (0.50 ml) was added and the solvent was blown off under a stream of nitrogen. The residual gum was suspended in dimethylsulfoxide (3 drops) and the mixture was heated at 120° C. for 16 h. The crude reaction product was purified using autoprep. HPLC to yield the title compound after freeze-drying as a solid (0.003 g).

LC/MS SYSTEM A $R_t$=3.36 min; LC/MS SYSTEM A m/z 527 (MH$^+$).

Example 7

(2R,3R,4S,5R)-(2-{6-Cyclopentylamino-2-[2-(1-methyl-1H-imidazol-4-yl)-ethylamino]-purin-9-yl}-5-(2-ethyl-2H-tetrazol-5-yl)-tetrahydro-furan-3,4-diol Acetate Example 7 was prepared in an analogous manner to Example 6 using cyclopentylamine (0.002 g, 0.025 mmol). The title compound was afforded after freeze drying as a solid (0.005 g), LC/MS SYSTEM A $R_t$=3.29 min; LC/MS SYSTEM A m/z 525 (MH$^+$).

Example 8

(2R,3S,4R,5R)-2-(2-Ethyl-2H-tetrazol-5-yl)-5-{6-(1S-hydroxymethyl-2-phenyl-ethylamino)-2-[2-(1-methyl-1H-imidazol-4-yl)-ethylamino]-purin-9-yl}-tetrahydro-furan-3,4-diol Acetate

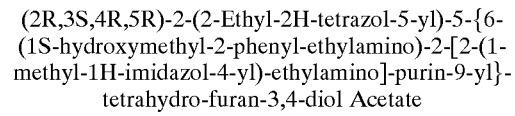

Example 8 was prepared in an analogous manner to Example 6 using (S)-(−)-2-amino-3-phenyl-1-propanol (0.004 g, 0.025 mmol). The title compound was afforded after freeze drying as a solid (0.005g), LC/MS SYSTEM A $R_t$=3.37 min; LC/MS SYSTEM A m/z 591 (MH$^+$).

Example 9

(2R,3R,4S,5R)-2-{6-(3,3-Dimethyl-butylamino)-2-[2-(1-methyl-1H-imidazol-4-yl)-ethylamino]-purin-9-yl}-5-(2-ethyl-2H-tetrazol-5-yl)-tetrahydro-furan-3,4-diol Acetate

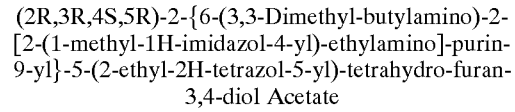

Example 9 was prepared in an analogous manner to Example 6 using 3,3-dimethylbutylamine (0.004 g, 0.025 mmol). The title compound was afforded after freeze drying as a solid (0.004 g).

LC/MS SYSTEM A $R_t$=3.53 min; LC/MS SYSTEM A m/z 541 (MH$^+$).

Example 10

(2R,3R,4S,5R)-2-[6-Amino-2-(2R-hydroxy-cyclopent-1R-ylamino)-purin-9-yl]-5-(2-ethyl-2H-tetrazol-5-yl)-tetrahydro-furan-3,4-diol Hydrochloride

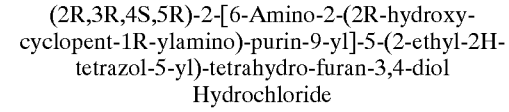

Intermediate 12 (2.00 g, 5.4 mmol) and (R,R)-aminocyclopentan-2-ol [see WO94/17090; Ref. L. E. Over-

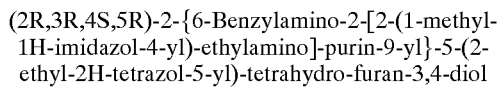
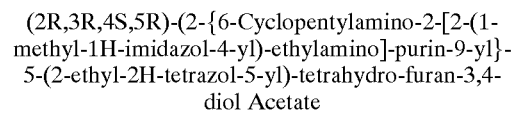

man and S. Sugai, J. Org. Chem., 1985, 50, 4154] (3.74 g, 27.0 mmol) in dry dimethylsulphoxide (4 ml) were stirred at 110° C. for 64 h. prior to concentration in vacuo. The crude product was purified using Solid Phase Extraction (SPE) chromatography ($NH_2$ aminopropyl Bondelute) cartridges, the residue was dissolved in dichloromethane (100 ml) and applied to 5 SPE cartridges (20 ml per cartridge), the cartridges were sequentially washed with dichloromethane (5×50 ml) and actetonitrile (5×50 ml) and crude product eluted with methanol (5×50 ml). The combined methanolic fractions were concentrated in vacuo and further purified by column chromatography on flash silica eluting with 10% methanol in dichloromethane to afford the impure product (1.00 g). This impure material was purified by preparative h.p.l.c. (14% acetonitrile in water [acetic acid modifier] over 30 minutes, λ=254) and to afford upon freeze drying a white foam (502 mg). The product was disolved in water (50 ml) and aqueous 2N hydrochloric acid (0.44 ml) was added. The resultant solution was freeze dried to afford the title compound as a white foam (497 mg).

Analysis found C, 42.52%; H, 5.56%; N, 28.74%. $C_{21}H_{26}N_{10}O_4$.HCl0.08$H_2O$ requires C, 42.25%; H, 5.55%; N, 28.98%, Analytical h.p.l.c. (gradient profile 10–60% acetonitrile in water in 25 min[trifluoroacetic acid modifier]), Rt 9.59 min.

Example 11

(2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol A mixture of (S)-(−)-2-amino-3-phenyl-1-propanol (1.403 g, 9.3 mmoles), Intermediate 12 (0.683 g, 1.86 mmoles) and sodium bicarbonate (0.393 g, 4.68 mmoles) in dimethylsulphoxide (2 ml) was heated with stirring at 120° C. for 48 h., then allowed to cool before solvent was removed under reduced pressure at 75° C. The residue was dissolved in dichloromethane (25 ml) and applied to 2 Solid Phase Extraction (SPE) chromatography ($NH_2$ aminopropyl Bondelute) cartridges, the cartridges were sequentially washed with dichloromethane (25 ml) and acetonitrile (25 ml) and crude product eluted with methanol (3×25 ml). The combined methanolic fractions were concentrated in vacuo and this impure material was purified by preparative HPLC (22% acetonitrile in water [acetic acid modifier] over 30 minutes, λ=254) and solvent was removed in vacuo affording the free base as a white foam (379 mg).

LC/MS SYSTEM A $R_t$=3.54 min; LC/MS SYSTEM A m/z 483 ($MH^+$).

Example 11 (Alternative Process)

To a 100-mL three neck round bottom flask was added Intermediate 26 (1.21 g), L-phenylalaninol (1.09 g), dimethyl sulfoxide (3.0 mL) and diisopropylethylamine (9.0 mL). The mixture was heated at reflux for ca. 23 hours then concentrated in vacuo. The resultant oil was treated with water (20 mL) and ethyl acetate (25 mL). The layers were separated and the aqueous layer extracted three times with ethyl acetate (15 mL). The combined organic layers were washed four times with 20 brine (20 mL), dried over anhydrous sodium sulfate, and concentrated in vacuo to provide intermediate grade title product as an oil. The oil was chromatographed on 230–400 mesh silica gel (42 g) Elution with 90:10 dichloromethane:methanol yielded title product (1.33 g) (80% yield) as a brown solid: TLC (90:10 methylene chloride/methanol, then 1:1 hexanes/ethyl acetate) rf=0.45.

Example 11a (2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol Hydrochloride Example 11 (freebase) (0.379 g, 0.79 mmol) was dissolved in water (50 ml) and aqueous 2N hydrochloric acid (0.39 ml) was added. The resultant solution was freeze dried to afford the title compound as a white foam (0.368 g).

m.p. 174.1° C. (decomposes); Analysis Found: C, 46.35; H, 5.40; N, 25.58%; $C_{21}H_{26}N_{10}O_4$. 1.00 HCl. 1.2 $H_2O$ C, 46.66; H, 5.48; N, 25.91%. Mass spectrum m/z 483 ($MH^+$ for $C_{21}H_{26}N_{10}O_4$).

Example 11b (2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol 1-hydroxy-2-naphthoate Example 11 (freebase) (0.300 g, 0.62 mmol) was dissolved in industrial methylated spirit (3 ml), any insolubles were filtered off and washed with industrial methylated spirit (0.5 ml). 1-Hydroxy-2-naphthoic acid (0.117 g, 0.62 mmol) was dissolved in industrial methylated spirit (1.5 ml), filtered and washed/rinsed with industrial methylated spirit (0.5 ml). The two solutions were combined, mixed well and a cloudy suspension was formed. The mixture was left to stand at 20° C. for 19 h., supernatant was removed and the crystalline solid was washed with industrial methylated spirit (3×1 ml) and airdried affording the title compound as an off-white powdery crystalline solid (0.296 g)

LC/MS SYSTEM A $R_t$=3.57 min; LC/MS SYSTEM A m/z 483 ($MH^+$).

Example 11c (2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol Sulfate Example 11 (freebase) (0.325 g, 0.67 mmol) was dissolved in industrial methylated spirit (6 ml) and treated dropwise over 30 min. with industrial methylated spirit (4 ml) containing sulfuric acid (0.67 ml). The resultant mixture was stirred under nitrogen for 24 h. whereupon a cloudy suspension was observed. The mixture was kept at 4° C. for 72 h. and a gum formed. Upon scratching with a spatula and leaving for 30 min. a white crystalline solid formed. Industrial methylated spirit (5 ml) was added and a white solid was filtered off. The filtrate was combined with the residual gum and stirred for a further 30 min., the volume was reduced in vacuo and a white solid was formed which was recrystallised from cooling industrial methylated spirit and combined with the previous crop to furnish the title compound as a white crystalline solid (0.242 g).

LC/MS SYSTEM A $R_t$=3.43 min; LC/MS SYSTEM A m/z 483 ($MH^+$).

Example 11d (2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol Mesylate A solution of Example 11 (freebase) (0.300 g, 0.62 mmol) in industrial methylated spirit (3 ml) was treated dropwise with a solution of methanesulfonic acid (0.042 g, 0.62 mmol) in industrial methylated spirit (3 ml). The formed cloudy solution was cooled to ca. 4° C. for 16 h., before the supernatant was removed and the solid was washed with industrial methylated spirit twice, filtered and dried under vacuum to afford the title compound as a white solid (0.306 g)

LC/MS SYSTEM A $R_t$=3.56 min; LC/MS SYSTEM A m/z 483 (MH$^+$).

Example 11e (2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol Maleate Example 11 (freebase) (0.301 g, 0.62 mmol) was dissolved in industrial methylated spirit (2.5 ml), any insolubles were filtered off and washed with industrial methylated spirit (0.5 ml). Maleic acid (0.072 g, 0.62 mmol) was dissolved in industrial methylated spirit (1 ml), filtered and washed/rinsed with industrial methylated spirit (0.2 ml). The two solutions were combined and mixed well and a cloudy solution was formed. The mixture was left to stand at 20° C. for 19 h. and a small amount of solid had formed. The mixture was briefly heated gently and allowed to stand at 20° C. for 4 h. The resultant crystals were filtered, washed with industrial methylated spirit (1×1 ml, 1×2 ml) and air-dried to furnish the title compound as a white powdery crystalline solid (0.290 g).

LC/MS SYSTEM A $R_t$=3.54 min; LC/MS SYSTEM A m/z 483 (MH$^+$).

Example 11e (Alternative Process)

To a round bottom flask was added Example 11 (free base) (1.29 g) and 10% methanol-ethanol (10 mL). The mixture was warmed and filtered through No. 2 Whatman filter paper. The filter was washed with 10% methanol-ethanol (2.1 mL) and an additional 2 mL of 10% methanol-ethanol was added to the filtrate when the cloudy solution became clear. A solution of maleic acid (311 mg in 2 mL of 10% methanol-ethanol) was added to this solution. The solution was seeded with appropriate crystals and allowed to stand at room temperature for 3 and one-half hours. The mixture was filtered and the cake was washed with absolute ethanol (3 mL). The solid was dried at 60° C. to provide title product (1.42 g) (89% yield) as a crystalline white solid: m.p. 169.5° C.; TLC (90:10 methylene chloride/methanol) rf=0.45.

Example 12

(2R,3R,4S,5R)-2-(6-Amino-2-cyclopentylamino-purin-9-yl)-5-(2-ethyl-2H-tetrazol-5-yl)-tetrahydro-furan-3,4-diol bis(Trifluoroacetate)

Intermediate 12 (0.050 g, 0.14 mmol) and cyclopentylamine (0.08 ml, 0.68 mmol) in anhydrous dimethysulfoxide (0.1 ml) was heated at 120° C. for 7 days. A further portion of cyclopentylamine (0.04 ml, 0.34 mmol) with additional dimethylsulfoxide (2 drops) and the reaction mixture was heated at 120° C. for a further 24 h. The reaction mixture was diluted with methanol (3 ml) and purified using preparative HPLC (10–60% acetonitrile). Solvent was removed in vacuo, the residue azeotroped with methanol and dried in vacuo. After tituration with diethyl ether the title compound was obtained as a pale yellow solid (0.034 g).

LC/MS SYSTEM A $R_t$=3.34 min; LC/MS SYSTEM A m/z 417 (MH$^+$).

Example 13

(2R,3R,4S,5R)-2-[6-Amino-2-(4-fluoro-phenylamino)-purin-9-yl]-5-(2-ethyl-2H-tetrazol-5-yl)-tetrahydro-furan-3,4-diol Trifluoroacetate Example 13 was prepared in an analogous manner to Example 12 using 4-fluoroaniline (0.06 ml, 0.68 mmol) and heating at 120° C. for 48 h. The reaction mixture was diluted with methanol (3 ml) and purified using preparative HPLC (10–60% acetonitrile). Solvent was removed in vacuo, the residue azeotroped with methanol and dried in vacuo affording the title compound as an off-white solid (0.049 g).

LC/MS SYSTEM A $R_t$=3.74 min; LC/MS SYSTEM A m/z 443 (MH$^+$).

Example 14

(2R,3R,4S,5R)-2-{6-Amino-2-[2-(4-amino-phenyl)-ethylamino]-purin-9-yl}-5-(2-ethyl-2H-tetrazol-5-yl)-tetrahydro-furan-3,4-diol Formate Intermediate 12 (0.050 g, 0.14 mmol) and 2-(4-aminophenylethyl)amine (0.074 g, 0.68 mmol) in anhydrous dimethysulfoxide (0.2 ml) was heated at 120° C. under nitrogen for 48 h. and the crude reaction mixture was purified using autoprep. HPLC. The solvent was removed in vacuo to yield the title compound as a yellow coloured film (0.032 g).

LC/MS SYSTEM A $R_t$=3.21 min; LC/MS SYSTEM A m/z 468 (MH$^+$).

Example 15

(2R,3R,4S,5R)-2-{6-Amino-2-[2-(3,4-dihydroxy-phenyl)-ethylamino]-purin-9-yl}-5-(2-ethyl-2H-tetrazol-5-yl)-tetrahydro-furan-3,4-diol Formate Intermediate 12 (0.030 g, 0.08 mmol) and 3-hydroxytyramine (0.112g, 0.82 mmol) in anhydrous dimethysulfoxide (0.2 ml) was heated at 115° C. under nitrogen for 24 h. and the crude reaction mixture was purified using autoprep. HPLC. The solvent was removed in vacuo to yield the title compound as a brown coloured film (0.043 g).

LC/MS SYSTEM A $R_t$=3.53 min; LC/MS SYSTEM A m/z 485 (MH$^+$).

Example 16

(2R,3R,4S,5R)-2-{6-Amino-2-[2-(4-hydroxy-phenyl)-ethylamino]-purin-9-yl}-5-(2-ethyl-2H-tetrazol-5-yl)-tetrahydro-furan-3,4-diol Formate Example 16 was prepared in an analogous manner to Example 15 using tyramine (0.112 g, 0.82 mmol). The crude reaction mixture was purified using autoprep. HPLC. The solvent was removed in vacuo to yield the title compound as a brown coloured film (0.033 g).

LC/MS SYSTEM A $R_t$=3.53 min; LC/MS SYSTEM A m/z 469 (MH$^+$).

Example 17

4-(2-{6-Amino-9-[5R-(2-ethyl-2H-tetrazol-5-yl)-3R,4S-Dihydroxy-tetrahydro-furan-2R-yl]-9H-purin-2-ylamino}-ethyl)-benzenesulfonamide Formate Example 17 was prepared in an analogous manner to Example 15 using 4-(2-aminoethyl)benzenesulfonamide (0.163 g, 0.82 mmol). The crude reaction mixture was purified using autoprep. HPLC. The solvent was removed in vacuo to yield the title compound as a yellow coloured film (0.038 g).

LC/MS SYSTEM A $R_t$=3.42 min; LC/MS SYSTEM A m/z 532 (MH$^+$).

Example 18

(2R,3R,4S,5R)-2-{6-Amino-2-[2-(4-methoxy-phenyl)-ethylamino]-purin-9-yl}-5-(2-ethyl-2H-tetrazol-5-yl)-tetrahydro-furan-3,4-diol Formate Example 18 was prepared in an analogous manner to Example 15 using 4-methoxyphenethylamine (0.12 ml, 0.82 mmol). The crude reaction mixture was purified using autoprep. HPLC. The solvent was removed in vacuo to yield the title compound as a clear and colourless film (0.024 g).

LC/MS SYSTEM A $R_t$=3.80 min; LC/MS SYSTEM A m/z 483 (MH$^+$).

Example 19

(2R,3R,4S,5R)-2-[6-Amino-2-(bicyclo[2.2.1]hept-2-ylamino)-purin-9-yl]-5-(2-ethyl-2H-tetrazol-5-yl)-tetrahydro-furan-3,4-diol Trifluoroacetate Intermediate 12 (0.030 g, 0.08 mmol) and (±)-exo-2-aminonorbornane (0.10 ml, 0.82 mmol) in anhydrous dimethysulfoxide (0.2 ml) was heated at 115° C. under nitrogen for 24 h. The reaction mixture was combined with crude reaction product obtained from Intermediate 12 (0.050 g, 0.14 mmol) and (±)-exo-2-aminonorbornane (0.10 ml, 0.82 mmol) in anhydrous dimethylsulfoxide (0.2 ml) heated at 120° C. under nitrogen for 16 h., this mixture was heated at 115° C. for 96 h. under nitrogen. The crude reaction mixture was purified using autoprep. HPLC. The solvent was removed in vacuo to yield impure product which was purified using preparative HPLC (10–60% acetonitrile). Solvent was removed in vacuo, the residue azeotroped with methanol and dried in vacuo yielding the title compound as a white solid (0.009 g).

LC/MS SYSTEM A $R_t$=3.70 min; LC/MS SYSTEM A m/z 443 (MH$^+$).

Example 20

(2R,3R,4S,5R)-2-{6-Amino-2-[2-(3,4-dimethoxy-phenyl)-ethylamino]-purin-9-yl}-5-(2-ethyl-2H-tetrazol-5-yl)-tetrahydro-furan-3,4-diol Trifluoroacetate Intermediate 12 (0.050 g, 0.14 mmol) and 3,4-dimethoxyphenethylamine (0.123 g, 0.68 mmol) in anhydrous dimethysulfoxide (0.1 ml) was heated at 120° C. under nitrogen for 24 h. The reaction mixture was diluted with methanol (3 ml) and purified using preparative HPLC (10–60% acetonitrile). Solvent was removed in vacuo, the residue azeotroped with methanol and dried in vacuo yielding the title compound as a yellow gum (0.089 g), LC/MS SYSTEM A $R_t$=3.61 min; LC/MS SYSTEM A m/z 513 (MH$^+$).

Example 21

(2R,3R,4S,5R)-2-[6-(2,2-Diphenyl-ethylamino)-2-(pyrrolidin-3R-ylamino)-purin-9-yl]-5-(2-ethyl-2H-tetrazol-5-yl)-tetrahydro-furan-3,4-diol Dihydrochloride Intermediate 10 (0.849 g, 1.42 mmol) was dissolved in methanol (4 ml), ethyl acetate (20 ml) and treated dropwise with ethereal hydrogen chloride (1M; 2.84 ml). Ether (30 ml) was added and the mixture stirred for 0.75 h. The gum was dissolved in methanol, and ether was added gradually while stirring until the mixture became cloudy, whereupon ethylacetate-ether (1:1) was added gradually generating another gum. The gum was dissolved in methanol and ether was added gradually until no more precipitate formed. The mixture was left to stir at room temperature for 16 h. The mixture was allowed to settle and the solvent decanted off. The precipitate was washed with ether. Nitrogen was blown over the slurry for 0.5 h. The solvent was removed in vacuo yielding the title compound as a cream solid (0.77 g).

LC-MS m/z 598. (MH$^+$ for $C_{30}H_{35}N_{11}O_3$). TLC SiO$_2$ (dichloromethane:ethanol:880 ammonia 100:8:1) Rf 0.1.

Example 22

(2R,3R,4S,5R)-2-[2-[2-(6-Amino-pyridin-2-yl)-ethylamino]-6-(2,2-diphenyl-ethylamino)-purin-9-yl]-5-(2-ethyl-2H-tetrazol-5-yl)-tetrahydro-furan-3,4-diol tris(Trifluoroacetate)

Intermediate 9 (0.040 g, 0.07 mmol) and Intermediate 24 (0.050 g, 0.36 mmol) in dimethylsulfoxide (0.5 ml) was heated at 130° C. under nitrogen for 24 h. The reaction mixture was diluted with methanol (8 ml) and purified using preparative HPLC (20–90% acetonitrile). Solvent was removed in vacuo, the residue azeotroped with methanol and dried in vacuo yielding the title compound as a pale yellow solid (0.033 g), LC/MS SYSTEM A $R_t$=3.76 min; LC/MS SYSTEM A m/z 649 (MH$^+$).

Example 23

(2R,3S,4R,5R)-2-(2-Ethyl-2H-tetrazol-5-yl)-5-[6-(3-iodo-benzylamino)-2-(pyrrolidin-3R-ylamino)-purin-9-yl]-tetrahydro-furan-3,4-diol Diformate Intermediate 7 (0.012 g, 0.025 mmol) was dissolved in isopropanol (0.25 ml), isopropanol (0.25 ml) containing di-isopropylethylamine (0.006 g, 0.025 mmol) was added, followed by the addition of 3-iodobenzylamine (0.006 g, 0.025 mmol) in isopropanol (0.25 ml). The mixture was left at 20° C. for 16 h. whereupon pyrrolidin-3R-ylamine (0.026 g, 0.30 mmol) in isopropanol (0.50 ml) was added and the solvent was blown off under a stream of nitrogen. The residual gum was suspended in dimethylsulfoxide (0.1 ml) and the mixture was heated at 120° C. for 60 h. The crude reaction product was purified using autoprep. HPLC to yield the title compound after freeze-drying as a white solid (0.005 g).

LC/MS SYSTEM A $R_t$=4.13 min; LC/MS SYSTEM A m/z 634 (MH$^+$).

Example 24

(2R,3R,4S,5R)-2-[6-(1-Ethyl-propylamino)-2-(2-piperidin-1-yl-ethylamino)-purin-9-yl]-5-(2-methyl-2H-tetrazol-5-yl)-tetrahydro-furan-3,4-diol Diformate Intermediate 17 (0.012 g, 0.025 mmol) was dissolved in isopropanol (0.25 ml), isopropanol (0.25 ml) containing di-isopropylethylamine (0.003 g, 0.025 mmol) was added, followed by the addition of 3-pentylamine (0.002 g, 0.025 mmol) in isopropanol (0.25 ml). The mixture was left at 20° C. for 48 h. whereupon 2-piperidinoethylamine (0.032 g, 0.25 mmol) in isopropanol (0.50 ml) was added and the solvent was blown off under a stream of nitrogen. The residual gum was suspended in dimethylsulphoxide (3–5 drops) and the mixture was heated at 130° C. for 24 h. The crude reaction product was purified using autoprep. HPLC to yield the title compound after freeze-drying as a brown solid (0.004 g).

LC/MS SYSTEM A $R_t$=3.59 min; LC/MS SYSTEM A m/z 515 (MH$^+$).

Example 25

(2R,3R,4S,5R)-2-[6-Cyclopentylamino-2-(2-piperidin-1-yl-ethylamino)-purin-9-yl]-5-(2-methyl-2H-tetrazol-5-yl)-tetrahydro-furan-3,4-diol Diformate Example 25 was prepared in an analogous manner to Example 24 using cyclopentylamine (0.002 g, 0.025 mmol) at 21° C. for 20 h. and using 2-piperidinoethylamine (0.032 g, 0.25 mmol) at 130° C. for 40 h. The title compound was afforded after freeze drying as a brown-coloured solid (0.003 g).

LC/MS SYSTEM A $R_t$=3.20 min; LC/MS SYSTEM A m/z 514 (MH$^+$).

Example 26

(2R,3R,4S,5R)-2-[6-(2,2-Diphenyl-ethylamino)-2-(2-piperidin-1-yl-ethylamino)-purin-9-yl]-5-(2-methyl-2H-tetrazol-5-yl)-tetrahydro-furan-3,4-diol Diformate Example 26 was prepared in an analogous manner to Example 24 using 2,2-diphenylethylamine (0.005g, 0.025 mmol) at 21° C. for 20 h. and using 2-piperidinoethylamine (0.032 g, 0.25 mmol) heating at 100° C. for 96 h. The title compound was afforded after freeze drying as a beige coloured solid (0.003 g).

LC/MS SYSTEM A $R_t$=3.78 min; LC/MS SYSTEM A m/z 626 (MH$^+$).

Example 27

(2R,3R,4S,5R)-2-{6-(2,2-Diphenyl-ethylamino)-2-[2-(1-methyl-1H-imidazol-4-yl)-ethylamino]-purin-9-yl}-5-(2-methyl-2H-tetrazol-5-yl)-tetrahydro-furan-3,4-diol Formate Example 27 was prepared in an analogous manner to Example 24 using 2,2-diphenylethylamine (0.005 g, 0.025 mmol) at 21° C. for 20 h. and using 1-methylhistamine (0.032 g, 0.25 mmol) heating at 100° C. for 16 h. The title compound was afforded after freeze drying as a white solid (0.006 g).

LC/MS SYSTEM A $R_t$=3.71 min; LC/MS SYSTEM A m/z 623 (MH$^+$).

Example 28

(2R,3R,4S,5R)-2-{6-(3,3-Dimethyl-butylamino)-2-[2-(1-methyl-1H-imidazol-4-yl)-ethylamino]-purin-9-yl}-5-(2-methyl-2H-tetrazol-5-yl)-tetrahydro-furan-3,4-diol Formate Example 28 was prepared in an analogous manner to Example 24 using 3,3-dimethylbutylamine (0.003 g, 0.025 mmol) and 1-methylhistamine (0.031 g, 0.25 mmol) heating at 100° C. for 16 h. The title compound was afforded after freeze drying as a white solid (0.004 g).

LC/MS SYSTEM A $R_t$=3.45 min; LC/MS SYSTEM A m/z 527 (MH$^+$).

Example 29

(2R,3R,4S,5R)-2-{6-(3-Iodo-benzylamino)-2-[2-(1-methyl-1H-imidazol-4-yl)-ethylamino]-purin-9-yl}-5-(2-methyl-2H-tetrazol-5-yl)-tetrahydro-furan-3,4-diol Formate Example 29 was prepared in an analogous manner to Example 24 using 3-iodobenzylamine (0.006 g, 0.025 mmol) and 1-methylhistamine (0.031 g, 0.25 mmol) heating at 100° C. for 16 h. The title compound was afforded after freeze drying as a pale yellow solid (0.006 g).

LC/MS SYSTEM A $R_t$=3.57 min; LC/MS SYSTEM A m/z 659 (MH$^+$).

Example 30

(2R,3R,4S,5R)-2-{6-Benzylamino-2-[2-(1-methyl-1H-imidazol-4-yl)-ethylamino]-purin-9-yl}-5-(2-methyl-2H-tetrazol-5-yl)-tetrahydro-furan-3,4-diol Formate Example 30 was prepared in an analogous manner to Example 24 using benzylamine (0.003 g, 0.025 mmol) at 21° C. for 20 h. and using 1-methylhistamine (0.032 g, 0.25 mmol) heating at 100° C. for 16 h. The title compound was afforded after freeze drying as an orange gum (0.004 g), LC/MS SYSTEM A $R_t$=3.32 min; LC/MS SYSTEM A m/z 533 (MH$^+$).

Example 31

(2R,3R,4S,5R)-2-{6-(2-Cyclohexyl-ethylamino)-2-[2-(1-methyl-1H-imidazol-4-yl)-ethylamino]-purin-9-yl}-5-(2-methyl-2H-tetrazol-5-yl)-tetrahydro-furan-3,4-diol Formate Example 31 was prepared in an analogous manner to Example 24 using 2-cyclohexylethylamine (0.003 g, 0.025 mmol) and 1-methylhistamine (0.031 g, 0.25 mmol) heating at 100° C. for 16 h. The title compound was afforded after freeze drying as a yellow gum (0.003 g).

LC/MS SYSTEM A $R_t$=3.62 min; LC/MS SYSTEM A m/z 553 (MH$^+$).

Example 32

(2R,3R,4S,5R)-2-{6-(1S-Hydroxymethyl-2-phenyl-ethylamino)-2-[2-(1-methyl-1H-imidazol-4-yl)-ethylamino]-purin-9-yl}-5-(2-methyl-2H-tetrazol-5-yl)-tetrahydro-furan-3,4-diol Formate Example 32 was prepared in an analogous manner to Example 24 using (S)-(−)-2-amino-3-phenyl-1-propanol (0.004 g, 0.025 mmol) and 1-methylhistamine (0.031 g, 0.25 mmol) heating at 100° C. for 16 h. The title compound was afforded after freeze drying as a light brown coloured solid (0.003 g).

LC/MS SYSTEM A $R_t$=3.32 min; LC/MS SYSTEM A m/z 577 (MH$^+$).

Example 33

(2R,3R,4S,5R)-2-{6-(1-Ethyl-propylamino)-2-[2-(1-methyl-1H-imidazol-4-yl)-ethylamino]-purin-9-yl}-5-(2-methyl-2H-tetrazol-5-yl)-tetrahydro-furan-3,4-diol Formate Example 33 was prepared in an analogous manner to Example 24 using 3-pentylamine (0.002 g, 0.025 mmol) and 1-methylhistamine (0.031 g, 0.25 mmol) heating at 100° C. for 16 h. The title compound was afforded after freeze drying as a white solid (0.003 g).

LC/MS SYSTEM A $R_t$=3.26 min; LC/MS SYSTEM A m/z 513 (MH$^+$).

Example 34

(2R,3R,4S,5R)-2-{2-[2-(1-Methyl-1H-imidazol-4-yl)-ethylamino]-6-phenethylamino-purin-9-yl}-5-(2-methyl-2H-tetrazol-5-yl)-tetrahydro-furan-3,4-diol Formate Example 34 was prepared in an analogous manner to Example 24 using 2-phenylethylamine (0.003 g, 0.025 mmol) and 1-methylhistamine (0.031 g, 0.25 mmol) heating at 100° C. for 16 h. The title compound was afforded after freeze drying as a cream coloured solid (0.005 g).

LC/MS SYSTEM A $R_t$=3.40 min; LC/MS SYSTEM A m/z 547 (MH$^+$).

Example 35

(2R,3R,4S,5R)-2-[2-(trans-4-Amino-cyclohexylamino)-6-(1S-hydroxymethyl-2-phenyl-ethylamino)-purin-9-yl]-5-(2-methyl-2H-tetrazol-5-yl)-tetrahydro-furan-3,4-diol bis(Formate)

Example 35 was prepared in an analogous manner to Example 24 using (S)-(−)-2-amino-3-phenyl-1-propanol (0.004 g, 0.025 mmol) at 21° C. for 20 h. and using trans-cyclohexane-1,4-diamine (preparable following methods described in International Patent Application WO94/17090) (0.029 g, 0.25 mmol) heating at 130° C. for 48 h. The title compound was afforded after freeze drying as a brown solid (0.004 g).

LC/MS SYSTEM A $R_t$=3.38 min; LC/MS SYSTEM A m/z 566 (MH$^+$).

Example 36

(2R,3R,4S,5R)-2-[6-Cyclopentylamino-2-(1S-hydroxymethyl-2-phenyl-ethylamino)-purin-9-yl]-5-(2-methyl-2H-tetrazol-5-yl)-tetrahydro-furan-3,4-diol Formate Example 36 was prepared in an analogous manner to Example 24 using cyclopentylamine (0.002 g, 0.025 mmol) at 21° C. for 20 h. and using (S)-(−)-2-amino-3-phenyl-1-propanol (0.038 g, 0.25 mmol) heating at 130° C. for 40 h. The title compound was afforded after freeze drying as a cream coloured solid (0.004 g).

LC/MS SYSTEM A $R_t$=4.03 min; LC/MS SYSTEM A m/z 537 (MH$^+$).

Example 37

(2R,3R,4S,5R)-2-[6-Amino-2-(1S-hydroxymethyl-2-phenyl-ethylamino)-purin-9-yl]-5-(2-methyl-2H-tetrazol-5-yl)-tetrahydro-furan-3,4-diol Formate Ammonia gas was bubbled through cooled (ice bath) tetrahydrofuran (10 ml) for 1 hr., Intermediate 17 (0.12 g, 0.25 mmol) was added and the resultant solution was stirred at 20° C. for 20 h. Ammonia gas was again bubbled through the solution for 1.5 h. prior to stirring at 20° C. for a further 18 h. Ammonia gas was again bubbled through the solution for 1.5 h prior to stirring at 20° C. for a further 15 h. The reaction mixture was evaporated to dryness in vacuo leaving a white solid which was dissolved in a dichloromethane (2 ml) and dimethylsulfoxide (5 ml) mixture. An aliquot of this solution (0.7 ml, 0.025 mmol) was dispensed and concentrated by solvent evaporation, to the residue was added neat (S)-(−)-2-amino-3-phenyl-1-propanol (0.038 g, 0.25 mmol). The mixture was heated at 130° C. for 42 h. and the crude reaction mixture was purified using autoprep. HPLC to yield the title compound after freeze-drying as a brown coloured solid (0.005 g).

LC/MS SYSTEM A $R_t$=3.43 min; LC/MS SYSTEM A m/z 469 (MH$^+$).

Example 38

(2R,3R,4S,5R)-2-{6-Amino-2-[2-(3,4-dimethoxy-phenyl)-ethylamino]-purin-9-yl}-5-(2-methyl-2H-tetrazol-5-yl)-tetrahydro-furan-3,4-diol Formate Example 38 was prepared in an analogous manner to Example 37 using 2-(3,4-dimethoxyphenyl)-ethylamine (0.038 g, 0.25 mmol) and heating at 130° C. for 20 hours. The title compound was afforded after freeze drying as a yellow oil (0.003 g).

LC/MS SYSTEM A $R_t$=3.44 min; LC/MS SYSTEM A m/z 499 (MH$^+$).

Example 39

(2R,3R,4S,5R)-2-[6-Amino-2-(bicyclo[2.2.1]hept-2-ylamino)-purin-9-yl]-5-(2-methyl-2H-tetrazol-5-yl)-tetrahydro-furan-3,4-diol Formate Example 39 was prepared in an analogous manner to Example 37 using (±)-exo-2-aminonorbornane (0.028 g, 0.25 mmol) and heating at 130° C. for 42 hours. The title compound was afforded after freeze drying as a cream coloured solid (0.003 g).

LC/MS SYSTEM B $R_t$=3.57 min; LC/MS SYSTEM B m/z 429 (MH$^+$).

Example 40

(2R,3R,4S,5R)-2-{6-(1S-Hydroxymethyl-2-phenyl-ethylamino)-2-[2-(1-methyl-1H-imidazol-4-yl)-ethylamino]-purin-9-yl}-5-(2-isopropyl-2H-tetrazol-5-yl)-tetrahydro-furan-3,4-diol Formate Intermediate 20 (0.012 g, 0.025 mmol) was dissolved in isopropanol (0.25 ml), isopropanol (0.25 ml) containing di-isopropylethylamine (0.003 g, 0.025 mmol) was added, followed by the addition of (S)-(−)-2-amino-3-phenyl-1-propanol (0.004 g, 0.025 mmol) in isopropanol (0.25 ml). The mixture was left at 20° C. for 12 h. whereupon 1-methylhistamine (0.031 g, 0.25 mmol) in isopropanol (0.50 ml) was added and the solvent was blown off under a stream of nitrogen. The residual gum was suspended in dimethylsulphoxide (3–5 drops) and the mixture was heated at 130° C. for 12 hours. The crude reaction product was purified using autoprep. HPLC to yield the title compound after freeze-drying as a pale brown solid (0.003 g).

LC/MS SYSTEM A Rt 3.63 min; LC/MS SYSTEM A m/z 605 (MH$^+$).

Example 41

(2R,3R,4S,5R)-2-{6-Cyclopentylamino-2-[2-(1-methyl-1H-imidazol-4-yl)-ethylamino]-purin-9-yl}-5-(2-isopropyl-2H-tetrazol-5-yl)-tetrahydro-furan-3,4-diol Formate Example 41 was prepared in an analogous manner to Example 40 using cyclopentylamine (0.002 g, 0.025 mmol)

and 1-methylhistamine (0.031 g, 0.25 mmol). The title compound was afforded after freeze drying as a pale brown solid (0.005 g).

LC/MS SYSTEM A $R_t$=3.62 min; LC/MS SYSTEM A m/z 539 (MH$^+$).

Example 42

(2R,3R,4S,5R)-2-{6-Amino-2-[2-(3,4-dimethoxy-phenyl)-ethylamino]-purin-9-yl}-5-(2-isopropyl-2H-tetrazol-5-yl)-tetrahydro-furan-3,4-diol Formate Ammonia gas was bubbled through cooled (ice bath) tetrahydrofuran (5 ml) for 1 hr. Intermediate 20 (0.12 g, 0.25 mmol) was added and the resultant solution was stirred at 20° C. for 12 h. Ammonia gas was again bubbled through the solution for 2 h. prior to stirring at 20° C. for a further 12 h. The reaction mixture was evaporated to dryness leaving a white solid, which was dissolved in dimethylsulfoxide (4 ml). An aliquot of this solution (0.4 ml, 0.025 mmol) was added to a sealed vial (Reactivial™) (1 ml) followed by the addition of 2-(3,4-dimethoxy-phenyl)-ethylamine (0.045 g, 0.25 mmol). The reaction mixture was heated at 120° C. for 3 days and the crude reaction mixture was purified using autoprep. HPLC to yield the title compound after freeze-drying as a solid (0.002g).

LC/MS SYSTEM A $R_t$=3.92 min; LC/MS SYSTEM A m/z 527 (MH$^+$).

Example 43

(2R,3R,4S,5R)-2-[6-(2,2-Diphenyl-ethylamino)-2-(2-pyrrolidin-1-yl-ethylamino)-purin-9-yl]-5-(2-ethyl-2H-tetrazol-5-yl)-tetrahydro-furan-3,4-diol tris(Trifluoroacetate)

Intermediate 9 (0.050 g, 0.09 mmol) and 1-(2-aminoethyl)pyrrolidine (0.052 g, 0.46 mmol) in dimethylsulfoxide (0.5 ml) was heated at 130° C. under nitrogen for 20.5 h. The reaction mixture was diluted with methanol (10 ml) and purified using preparative HPLC (20–100% acetonitrile). Solvent was removed in vacuo and dried in vacuo yielding the title compound as a yellow-brown solid (0.046 g) Mass Spectrum m/z 626 (MH$^+$ for $C_{32}H_{40}N_{11}O_3$). Analysis Found C, 46.94%; H, 4.48%; N, 16.19% $C_{32}H_{39}N_{11}O_3 \cdot 2.7C_2HF_3O_2 \cdot 1.0H_2O$ C, 47.21%; H, 4.63%; N, 16.19%.

Example 44

(2R,3R,4S,5R)-2-[6-(2,2-Diphenyl-ethylamino)-2-(2-morpholin-4-yl-ethylamino)-purin-9-yl]-5-(2-ethyl-2H-tetrazol-5-yl)-tetrahydro-furan-3,4-diol tris(Trifluoroacetate)

Intermediate 9 (0.050 g, 0.09 mmol) and 4-(2-aminoethyl)morpholine (0.059 g, 0.46 mmol) in dimethylsulfoxide (0.5 ml) was heated at 130° C. under nitrogen for 13 h. The reaction mixture was diluted with methanol (10 ml) and purified using preparative HPLC (20–100% acetonitrile). Solvent was removed in vacuo and dried in vacuo yielding the title compound as a pale yellow solid (0.053 g).

TLC $SiO_2$, (Dichloromethane, methanol; 5:1) Rf=0.52. Mass Spectrum m/z 642 (MH$^+$ for $C_{32}H_{40}N_{11}O_4$).

Example 45

(2R,3R,4S,5R)-2-[2-(1,1-Dioxo-tetrahydro-1.lambda.6-thiophen-3-ylamino)-6-(2,2-diphenyl-ethylamino)-purin-9-yl]-5-(2-ethyl-2H-tetrazol-5-yl)-tetrahydro-furan-3,4-diol bis(Trifluoroacetate)

Intermediate 9 (0.040 g, 0.07 mmol) and tetrahydro-3-thiophenamine-1,1-dioxide (0.099 g, 0.73 mmol) were heated at 130° C. under nitrogen for 20 h. The reaction mixture purified using preparative HPLC (20–100% acetonitrile). Solvent was removed in vacuo and dried in vacuo yielding the title compound as a pale brown solid (0.052 g).

TLC $SiO_2$, (Dichloromethane, methanol; 5:1) Rf=0.54. Mass Spectrum m/z 647 (MH$^+$ for $C_{30}H_{35}N_{10}O_5S$).

Example 46

(2R,3R,4S,5R)-2-[6-(2,2-Diphenyl-ethylamino)-2-(2-piperidin-1-yl-ethylamino)-purin-9-yl]-5-(2-ethyl-2H-tetrazol-5-yl)-tetrahydro-furan-3,4-diol bis(Trifluoroacetate)

Intermediate 9 (0.050 g, 0.09 mmol) and 2-ethylaminopiperidine (0.117 g, 0.91 mmol) were heated at 130° C. under nitrogen for 18 h. The reaction mixture was diluted with methanol (10 ml) and purified using preparative HPLC (20–100% acetonitrile). Solvent was removed in vacuo and dried in vacuo yielding the title compound as a pale yellow foam (0.049 g).

TLC $SiO_2$, (Dichloromethane, methanol; 5:1) Rf=0.24. Mass Spectrum m/z 640 (MH$^+$ for $C_{33}H_{42}N_{11}O_3$).

Example 47

(2R,3R,4S,5R)-2-[6-(2,2-Diphenyl-ethylamino)-2-(2-hydroxy-ethylamino)-purin-9-yl]-5-(2-ethyl-2H-tetrazol-5-yl)-tetrahydro-furan-3,4-diol Trifluoroacetate Intermediate 9 (0.050 g, 0.09 mmol) and 2-aminoethanol (0.056 g, 0.91 mmol) were heated at 130° C. under nitrogen for 20 h. The reaction mixture was diluted with methanol (10 ml) and purified using preparative HPLC (20–100% acetonitrile). Solvent was removed in vacuo and dried in vacuo yielding the title compound as a yellow solid (0.042 g).

TLC $SiO_2$, (Dichloromethane, methanol; 5:1) Rf 0.50. Mass Spectrum m/z 573 (MH$^+$ for $C_{28}H_{33}N_{10}O_4$).

Example 48

(2R,3S,4R,5R)-2-(2-Ethyl-2H-tetrazol-5-yl)-5-[6-(3-iodo-benzylamino)-2-(2-morpholin-4-yl-ethylamino)-purin-9-yl]-tetrahydro-furan-3,4-diol Intermediate 7 (0.012 g, 0.025 mmol) was dissolved in isopropanol (0.25 ml), isopropanol (0.25 ml) containing di-isopropylethylamine (0.006 g, 0.025 mmol) and 3-iodobenzylamine (0.002 g, 0.025 mmol) in isopropanol (0.25 ml) were added. The mixture was left at 20° C. for 12 h., whereupon 4-(2-aminoethyl)morpholine (0.039 g, 0.30 mmol) in isopropanol (0.50 ml) was added and the solvent was blown off under a stream of nitrogen. The residual gum was suspended in dimethylsulfoxide (6 drops) and the mixture was heated at 120° C. for 4 days. Concurrently Intermediate 7 (0.012 g, 0.025 mmol) was dissolved in isopropanol (0.25 ml), isopropanol (0.25 ml) containing di-isopropylethylamine (0.006 g, 0.025 mmol) and 3-iodobenzylamine (0.002 g, 0.025 mmol) in isopropanol (0.25 ml) were added. The mixture was left at 20° C. for 12 h. whereupon sodium methoxide (0.001 g, 0.025 mmol) in isopropanol (0.25 ml) was added with dimethylsulfoxide (3 drops). After 6 h. at 20° C., 4-(2-aminoethyl)morpholine (0.039 g, 0.30 mmol) in isopropanol (0.50 ml) was added and the solvent was blown off under a stream of nitrogen. The residual gum was suspended in dimethylsulfoxide (6 drops) and the mixture was heated at 120° C. for 4 days. The reaction mixtures from these two experiments were combined and purified using Solid Phase Extraction (SPE) chromatography (NH$_2$ aminopropyl Bondelute) cartridges, the residue was dissolved in dichloromethane (5 ml) and applied to 1 SPE cartridge (5 ml cartridge), the cartridge was sequentially washed with dichloromethane (5 ml), chloroform (5 ml), diethyl ether (5 ml), ethyl acetate (2×5 ml), acetonitrile (2×5 ml) acetone (2×5 ml) and methanol (2×5 ml). The combined methanol fractions were concentrated in vacuo and submitted to further purification with the residue being dissolved in dichloromethane (1 ml) and applied to 1 SPE cartridge (1 ml cartridge), the cartridge was sequentially washed with dichloromethane (1 ml), chloroform (1 ml), diethyl ether (1 ml), ethyl acetate (2×1 ml), acetonitrile (2 ×1 ml), acetone (2×1 ml) and methanol (2×1 ml). The combined methanol fractions were concentrated in vacuo affording the title compound as a beige coloured solid (0.004 g).

LC/MS SYSTEM A R$_t$=3.62 min. LC/MS SYSTEM A m/z 678 (MH$^+$).

Example 49

(2R,3S,4R,5R)-2-(2-Ethyl-2H-tetrazol-5-yl)-5-[2-(2-morpholin-4-yl-ethylamino)-6-phenethylamino-purin-9-yl]-tetrahydro-furan-3,4-diol Example 49 was prepared in an analogous manner to Example 48 using 2-phenethylamine (0.003 g, 0.025 mmol). The title compound was obtained as a beige coloured solid (0.004 g), LC/MS SYSTEM A R$_t$=3.50 min. LC/MS SYSTEM A m/z 566 (MH$^+$).

Example 50

(2R,3S,4R,5R)-2-(2-Ethyl-2H-tetrazol-5-yl)-5-[2-[2-(1-methyl-1H-imidazol-4-yl)-ethylamino]-6-(2-morpholin-4-yl-ethylamino)-purin-9-yl]-tetrahydro-furan-3,4-diol Diacetate Example 50 was prepared in an analogous manner to Example 6 using 4-(2-aminoethyl)morpholine (0.002 g, 0.025 mmol). The title compound was afforded after freeze drying as a solid (0.008 g).

LC/MS SYSTEM A R$_t$=2.86 min. LC/MS SYSTEM A m/z 570 (MH$^+$).

Example 51

(2R,3R,4S,5R)-2-{6-(3,3-Dimethyl-butylamino)-2-[2-(pyridin-2-ylamino)-ethylamino]-purin-9-yl}-5-(2-ethyl-2H-tetrazol-5-yl)-tetrahydro-furan-3,4-diol Acetate Intermediate 7, 3,3-dimethylbutylamine (0.188 g, 0.4 mmol) and diisopropylethylamine (0.051 g, 0.4 mmol) in iso-propyl alcohol (12 ml) were stirred at 20° C. for 16 h. An aliquot (0.75 ml) of this reaction was added to Intermediate 27 (0.034 g, 0.25 mmol) in isopropyl alcohol (0.25 ml) and the solvent was blown-off under a stream of nitrogen before the addition of dimethylsulfoxide (0.25 ml). The mixture heated at 120 ° C. for 16 h. and the crude reaction product was purified using autoprep. HPLC to yield the title compound after freeze-drying as a solid (0.004 g).

LC/MS SYSTEM A R$_t$=3.61 min, LC/MS SYSTEM A m/z 553 (MH$^+$).

Example 52

(2R,3R,4S,5R)-2-[6-(3,3-Dimethyl-butylamino)-2-(1S-hydroxymethyl-2-phenyl-ethylamino)-purin-9-yl]-5-(2-ethyl-2H-tetrazol-5-yl)-tetrahydro-furan-3, 4-diol Acetate Example 52 was prepared in an analogous manner to Example 51 using (S)-(−)-2-amino-3-phenyl-1-propanol (0.038 g, 0.25 mmol). The title compound was afforded after freeze drying as a solid (0.002 g).

LC/MS SYSTEM A R$_t$=4.28 min, LC/MS SYSTEM A m/z 567 (MH$^+$).

Example 53

(2R,3R,4S,5R)-2-[6-Amino-2-(trans-4-amino-cyclohexylamino)-purin-9-yl]-5-(2-ethyl-2H-tetrazol-5-yl)-tetrahydro-furan-3,4-diol Intermediate 12 (0.050g, 0.14 mmol), trans-1,4-diaminocyclohexane (0.154 g, 1.4 mmol) and dimethylsulfoxide (0.2 ml) were heated at 120° C. for 16 h. The crude reaction product was purified using autoprep. HPLC to yield the title compound after azeotroping with methanol (×3) as a light brown film (0.013 g).

LC/MS SYSTEM A R$_t$=2.89 min. LC/MS SYSTEM A m/z 446 (MH$^+$).

Example 54

(2R,3R,4S,5R)-2-{6-Amino-2-[2-(1-methyl-1H-imidazol-4-yl)-ethylamino]-purin-9-yl}-5-(2-ethyl-2H-tetrazol-5-yl)-tetrahydro-furan-3,4-diol Formate Intermediate 12, (0.030 g, 0.08 mmol) and 1-methylhistamine (0.101g, 0.82 mmol) in isopropanol (1.63 ml) were combined and solvent was removed under a stream of nitrogen, anhydrous dimethysulfoxide (0.2 ml) was added and heated at 115° C. under nitrogen for 24 h. and the crude reaction mixture was purified using autoprep. HPLC. The solvent was removed in vacuo to yield the title compound as a brown coloured film (0.013 g).

LC/MS SYSTEM A R$_t$=3.06 min, LC/MS SYSTEM A m/z 457 (MH$^+$).

Example 55

(2R,3R,4S,5R)-2-{6-Amino-2-[2-(pyridin-2-ylamino)-ethylamino)-purin-9-yl}-5-(2-ethyl-2H-tetrazol-5-yl)-tetrahydro-furan-3,4-diol Trifluoroacetate Example 55 was prepared in an analogous manner to Example 54 using 2-(pyridin-2-ylamino)-ethylamine (0.112 g, 0.82 mmol). The crude reaction mixture was purified using autoprep. HPLC and subsequently purified using preparative HPLC (10–40% acetonitrile). The solvent was removed in vacuo and the residue azeotroped with methanol to yield the title compound as a brown gum (0.006 g).

LC/MS SYSTEM A R$_t$=3.13 min. LC/MS SYSTEM A m/z 469 (MH$^+$).

Example 56

(2R,3R,4S,5R)-2-{6-(3,3-Dimethyl-butylamino)-2-[2-(1-methyl-1H-imidazol-4-yl)-ethylamino]-purin-9-yl}-5-(2-isopropyl-2H-tetrazol-5-yl)-tetrahydro-furan-3,4-diol Formate Example 56 was prepared in an analogous manner to Example 40 using 3,3-dimethylbutylamine (0.003 g, 0.025 mmol) and 1-methylhistamine (0.031 g, 0.25 mmol). The title compound was afforded after freeze drying as a pale brown solid (0.004 g).

LC/MS SYSTEM A $R_t$=3.88 min, LC/MS SYSTEM A m/z 555 (MH$^+$).

Example 57

(2R,3S,4R,5R)-2-(2-Isopropyl-2H-tetrazol-5-yl)-5-{2-[2-(1-methyl-1H-imidazol-4-yl)-ethylamino]-6-phenethylamino-purin-9-yl}-tetrahydro-furan-3,4-diol Formate Example 57 was prepared in an analogous manner to Example 40 using 2-phenethylamine (0.003 g, 0.025 mmol) and 1-methylhistamine (0.031 g, 0.25 mmol). The title compound was afforded after freeze drying as a pale brown solid (0.002 g).

LC/MS SYSTEM A $R_t$=3.81 min. LC/MS SYSTEM A m/z 575 (MH$^+$).

Example 58

(2R,3R,4S,5R)-2-{6-Benzylamino-2-[2-(1-methyl-1H-imidazol-4-yl)-ethylamino]-purin-9-yl}-5-(2-isopropyl-2H-tetrazol-5-yl)-tetrahydro-furan-3,4-diol Formate Example 58 was prepared in an analogous manner to Example 40 using benzylamine (0.003 g, 0.025 mmol) and 1-methylhistamine (0.031 g, 0.25 mmol). The title compound was afforded after freeze drying as a pale brown solid (0.013 g).

LC/MS SYSTEM A $R_t$=3.72 min. LC/MS SYSTEM A m/z 561 (MH$^+$).

Example 59

(2R,3R,4S,5R)-2-{6-(1-Ethyl-propylamino)-2-[2-(1-methyl-1H-imidazol-4-yl)-ethylamino]-purin-9-yl}-5-(2-isopropyl-2H-tetrazol-5-yl)-tetrahydro-furan-3,4-diol Formate Example 59 was prepared in an analogous manner to Example 40 using 1-ethylpropylamine (0.002 g, 0.025 mmol) and 1-methylhistamine (0.031 g, 0.25 mmol). The title compound was afforded after freeze drying as a pale brown solid (0.001 g).

LC/MS SYSTEM A $R_t$=3.71 min, LC/MS SYSTEM A m/z 541 (MH$^+$).

Example 60

(2R,3R,4S,5R)-2-[6-(3,3-Dimethyl-butylamino)-2-(2R-hydroxy-(R)-cyclopentylamino)-purin-9-yl]-5-(2-ethyl-2H-tetrazol-5-yl)-tetrahydro-furan-3,4-diol bis(Trifluoroacetate)

Intermediate 8 (0.030 g, 0.06 mmol) and (R,R)-aminocyclopentan-2-ol (0.100 g, 0.99 mmol) in dimethylsulfoxide (0.5 ml) was heated at 130° C. under nitrogen for 72 h. The crude reaction mixture was purified using preparative HPLC (10–100% acetonitrile). Solvent was removed in vacuo and dried in vacuo yielding the title compound as a brown gum (0.015 g).

LC/MS SYSTEM A $R_t$=4.13 min; LC/MS SYSTEM A m/z 517 MH$^+$).

Example 61

(2R,3R,4S,5R)-2-[6-Benzylamino-2-(1S-hydroxymethyl-2-phenyl-ethylamino)-purin-9-yl]-5-(2-ethyl-2H-tetrazol-5-yl)-tetrahydro-furan-3,4-diol Formate Example 61 was prepared in an analogous manner to Example 23 using benzylamine (0.003 g, 0.025 mmol) at 21° C. for 20 h. and (S)-(–)-2-amino-3-phenyl-1-propanol (0.038 g, 0.25 mmol) at 130° C. for 40 h. The title compound was afforded after freeze drying as a yellow solid (0.005 g).

LC/MS SYSTEM A $R_t$=4.24 min, LC/MS SYSTEM A m/z 573 (MH$^+$).

Example 62

(2R,3S,4R,5R)-2-(2-Ethyl-2H-tetrazol-5-yl)-5-[6-(1S-hydroxymethyl-2-phenyl-ethylamino)-2-(pyrrolidin-3R-ylamino)-purin-9-yl]-tetrahydro-furan-3,4-diol bis(Formate)

Example 62 was prepared in an analogous manner to Example 23 using (S)-(–)-2-amino-3-phenyl-1-propanol (0.004 g, 0.025 mmol) at 21° C. for 20 h. and pyrrolidin-3R-ylamine (0.022 g, 0.25 mmol) at 130° C. for 40 h. The title compound was afforded after freeze drying as a yellow solid (0.002 g).

LC/MS SYSTEM A $R_t$=2.28 min. LC/MS SYSTEM A m/z 552 (MH$^+$).

Example 63

(2R,3R,4S,5R)-2-[6-(1S-Hydroxymethyl-2-phenyl-ethylamino)-2-(2-pyridin-2-yl-ethylamino)-purin-9-yl]-5-(2-isopropyl-2H-tetrazol-5-yl)-tetrahydro-furan-3,4-diol Formate Example 63 was prepared in an analogous manner to Example 23 using Intermediate 20 (0.012 g, 0.025 mmol) and (S)-(–)-2-amino-3-phenyl-1-propanol (0.004 g, 0.025 mmol) at 21° C. for 20 h. and 2-(2-aminoethyl) pyridine (0.031 g, 0.25 mmol) at 130° C. for 40 h. The title compound was afforded after freeze drying as a brown foam (0.002 g).

LC/MS SYSTEM A $R_t$=3.79 min. LC/MS SYSTEM A m/z 528 (MH$^+$).

Example 64

(2R,3R,4S,5R)-2-[6-(1S-Hydroxymethyl-2-phenyl-ethylamino)-2-(pyrrolidin-3S-ylamino)-purin-9-yl]-5-(2-isopropyl-2H-tetrazol-5-yl)-tetrahydro-furan-3,4-diol bis(Formate)

Example 64 was prepared in an analogous manner to Example 23 using Intermediate 20 (0.012 g, 0.025 mmol) and (S)-(–)-2-amino-3-phenyl-1-propanol (0.004 g, 0.025 mmol) at 21° C. for 20 h. and neat pyrrolidin-3R-ylamine (0.021 g, 0.25 mmol) at 130° C. for 14 h. The title compound was afforded after freeze drying as a brown foam (0.002 g). Mass Spectrum m/z 566 (MH$^+$ for $C_{26}H_{35}N_{11}O_4$).

Example 65

(2R,3R,4S,5R)-2-[2-(1-Benzyl-pyrrolidin-3-ylamino)-6-(1-ethyl-propylamino)-purin-9-yl]-5-(2-ethyl-2H-tetrazol-5-yl)-tetrahydro-furan-3,4-diol bis (Formate)

Example 65 was prepared in an analogous manner to Example 23 using 1-ethylpropylamine (0.002 g, 0.025 mmol) at 21° C. for 20 h. and 1-benzyl-3-aminopyrrolidine (0.044 g, 0.25 mmol) at 120° C. for 60 h. The title compound was afforded after freeze drying as a yellow brown solid (0.002 g). LC/MS SYSTEM A $R_t$=3.73 min; LC/MS SYSTEM A m/z 578 (MH$^+$).

Example 66

(2R,3R,4S,5R)-2-[2-(1-Benzyl-pyrrolidin-3-ylamino)-6-cyclopentylamino-purin-9-yl]-5-(2-ethyl-2H-tetrazol-5-yl)-tetrahydro-furan-3,4-diol bis (Formate)

Example 66 was prepared in an analogous manner to Example 23 using cyclopentylamine (0.002 g, 0.025 mmol)

at 21° C. for 20 h. and 1-benzyl-3-aminopyrrolidine (0.044 g, 0.25 mmol) at 120° C. for 60 h. The title compound was afforded after freeze drying as a yellow brown solid (0.002 g). LC/MS SYSTEM A $R_t$=3.73 min; LC/MS SYSTEM A m/z 578 (MH$^+$).

Example 67

(2R,3R,4S,5R)-2-[2-(trans-4-Amino-cyclohexylamino)-6-(1-ethyl-propylamino)-purin-9-yl]-5-(2-isopropyl-2H-tetrazol-5-yl)-tetrahydro-furan-3,4-diol bis(Formate)

Example 67 was prepared in an analogous manner to Example 23 using Intermediate 20 (0.012 g, 0.025 mmol) and 1-ethylpropylamine (0.002 g, 0.025 mmol) at 21° C. for 20 h. and trans 1,4-diaminocyclohexane (0.029 g, 0.25 mmol) at 130° C. for 14 h. The title compound was afforded after freeze drying as a brown foam (0.002 g). LC/MS SYSTEM A $R_t$=3.47 min; LC/MS SYSTEM A m/z 530 (MH$^+$).

Example 68

(2R,3R,4S,5R)-2-[6-(1-Ethyl-propylamino)-2-(2-piperidin-1-yl-ethylamino)-purin-9-yl]-5-(2-isopropyl-2H-tetrazol-5-yl)-tetrahydro-furan-3,4-diol bis(Formate)

Example 68 was prepared in an analogous manner to Example 23 using Intermediate 20 (0.012 g, 0.025 mmol) and 1-ethylpropylamine (0.002 g, 0.025 mmol) at 21° C. for 20 h. and 2-piperidinoethylamine (0.032 g, 0.25 mmol) at 130° C. for 14 h. The title compound was afforded after freeze drying as a brown foam (0.001 g). Mass Spectrum m/z 544 (MH$^+$ for $C_{25}H_{41}N_{11}O_3$).

Example 69

(2R,3S,4R,5R)-2-(2-Ethyl-2H-tetrazol-5-yl)-5-[2-(1S-hydroxymethyl-2-phenyl-ethylamino)-6-(2-piperidin-1-yl-ethylamino)-purin-9-yl]-tetrahydro-furan-3,4-diol Formate Example 69 was prepared in an analogous manner to Example 23 using 2-piperidinoethylamine (0.003 g, 0.025 mmol) at 21° C. for 20 h. and (S)-(−)-2-amino-3-phenyl-1-propanol (0.038 g, 0.25 mmol) at 120° C. for 60 h. The title compound was afforded after freeze drying as a yellow solid (0.002 g). LC/MS SYSTEM A $R_t$=3.64 min; LC/MS SYSTEM A m/z 594 (MH$^+$).

Example 70

(2R,3R,4S,5R)-2-[6-(1-Ethyl-propylamino)-2-(2-morpholin-4-yl-ethylamino)-purin-9-yl]-5-(2-isopropyl-2H-tetrazol-5-yl)-tetrahydro-furan-3,4-diol Diformate Example 70 was prepared in an analogous manner to Example 23 using Intermediate 20 (0.012 g, 0.025 mmol) and 1-ethylpropylamine (0.002 g, 0.025 mmol) at 21° C. for 20 h. and 4-(2-aminoethyl)morpholine (0.033 g, 0.25 mmol) at 130° C. for 14 h. The title compound was afforded after freeze drying as a brown foam (0.002 g). LC/MS SYSTEM A $R_t$=3.52 min; LC/MS SYSTEM A m/z 546 (MH$^+$).

Example 71

(2R,3R,4S,5R)-2-[6-Cyclopentylamino-2-(1S-hydroxymethyl-2-phenyl-ethylamino)-purin-9-yl]-5-(2-ethyl-2H-tetrazol-5-yl)-tetrahydro-furan-3,4-diol Formate Example 71 was prepared in an analogous manner to Example 23 using cyclopentylamine (0.002 g, 0.025 mmol) at 21° C. for 20 h. and (S)-(−)-2-amino-3-phenyl-1-propanol (0.038 g, 0.25 mmol) at 120° C. for 60 h. The title compound was afforded after freeze drying as a yellow solid (0.002 g). LC/MS SYSTEM A $R_t$=4.08 min; LC/MS SYSTEM A m/z 551 (MH$^+$).

Example 72

(2R,3R,4S,5R)-2-[6-(2-Cyclohexyl-ethylamino)-2-(pyrrolidin-3R-ylamino)-purin-9-yl]-5-(2-ethyl-2H-tetrazol-5-yl)-tetrahydro-furan-3,4-diol Diformate Example 72 was prepared in an analogous manner to Example 23 using 2-cyclohexylethylamine (0.003 g, 0.025 mmol) at 21° C. for 20 h. and pyrrolidin-3R-ylamine (0.021 g, 0.25 mmol) at 120° C. for 60 h. The title compound was afforded after freeze drying as a pale yellow solid (0.002 g). LC/MS SYSTEM A $R_t$=3.80 min; LC/MS SYSTEM A m/z 528 (MH$^+$).

Example 73

(2R,3R,4S,5R)-2-[6-(2-Cyclohexyl-ethylamino)-2-(pyrrolidin-3S-ylamino)-purin-9-yl]-5-(2-ethyl-2H-tetrazol-5-yl)-tetrahydro-furan-3,4-diol bis(Formate)

Example 73 was prepared in an analogous manner to Example 23 using 2-cyclohexylethylamine (0.003 g, 0.025 mmol) at 21° C. for 20 h. and pyrrolidin-3S-ylamine (0.021 g, 0.25 mmol) at 120° C. for 60 h. The title compound was afforded after freeze drying as a white solid (0.003 g). LC/MS SYSTEM A $R_t$=3.79 min; LC/MS SYSTEM A m/z 528 (MH$^+$).

Example 74

(2R,3S,4R,5R)-2-(2-Ethyl-2H-tetrazol-5-yl)-5-[6-phenethylamino-2-(pyrrolidin-3R-ylamino)-purin-9-yl]-tetrahydro-furan-3,4-diol bis(Formate)

Example 74 was prepared in an analogous manner to Example 23 using phenethylamine (0.003 g, 0.025 mmol) at 21° C. for 20 h. and pyrrolidin-3R-ylamine (0.021 g, 0.25 mmol) at 120° C. for 60 h. The title compound was afforded after freeze drying as a white solid (0.002 g). LC/MS SYSTEM A $R_t$=3.71 min; LC/MS SYSTEM A m/z 522 (MH$^+$).

Example 75

(2R,3R,4S,5R)-2-[2-(1-Benzyl-pyrrolidin-3-ylamino)-6-phenethylamino-purin-9-yl]-5-(2-ethyl-2H-tetrazol-5-yl)-tetrahydro-furan-3,4-diol bis (Formate)

Example 75 was prepared in an analogous manner to Example 23 using phenethylamine (0.003 g, 0.025 mmol) at 21° C. for 20 h. and 1-benzyl-3-aminopyrrolidine (0.044 g, 0.25 mmol) at 120° C. for 60 h. The title compound was afforded after freeze drying as a yellow solid (0.002 g). LC/MS SYSTEM A Rt=4.09 min; LC/MS SYSTEM A m/z 612 (MH$^+$).

Example 76

(2R,3S,4R,5R)-2-(2-Ethyl-2H-tetrazol-5-yl)-5-[6-(3-iodo-benzylamino)-2-(pyrrolidin-3S-ylamino)-purin-9-yl]-tetrahydro-furan-3,4-diol bis(Formate)

Example 76 was prepared in an analogous manner to Example 23 using 3-iodo-benzylamine (0.006 g, 0.025 mmol) at 21° C. for 20 h. and pyrrolidin-3R-ylamine (0.021 g, 0.25 mmol) at 120° C. for 60 h. The title compound was afforded after freeze drying as a white solid (0.002 g). LC/MS SYSTEM A $R_t$=3.86 min; LC/MS SYSTEM A m/z 634 (MH$^+$).

Example 77

(2R,3R,4S,5R)-2-[2-(1-Benzyl-pyrrolidin-3-ylamino)-6-(3-iodo-benzylamino)-purin-9-yl]-5-(2-ethyl-2H-tetrazol-5-yl)-tetrahydro-furan-3,4-diol bis (Formate)

Example 77 was prepared in an analogous manner to Example 23 using 3-iodo-benzylamine (0.006 g, 0.025 mmol) at 21° C. for 20 h. and 1-benzyl-3-aminopyrrolidine (0.044 g, 0.25 mmol) at 120° C. for 60 h. The title compound was afforded after freeze drying as a yellow solid (0.001 g). LC/MS SYSTEM A $R_t$=4.17 min; LC/MS SYSTEM A m/z 724 (MH$^+$).

Example 78

(2R,3S,4R,5R)-2-(2-Ethyl-2H-tetrazol-5-yl)-5-[6-(1S-hydroxymethyl-2-ethylamino)-2-(2-morpholin-4-yl-ethylamino)-purin-9-yl]-tetrahydro-furan-3,4-diol Formate Example 78 was prepared in an analogous manner to Example 23 using (S)-(−)-2-amino-3-phenyl-1-propanol (0.004 g, 0.025 mmol) at 21° C. for 20 h. and 4-(2-aminoethyl)morpholine (0.033 g, 0.25 mmol) at 120° C. for 60 h. The title compound was afforded after freeze drying as a yellow-brown gum (0.002 g).

LC/MS SYSTEM A $R_t$=3.43 min; LC/MS SYSTEM A m/z 552 (MH$^+$).

Example 79

(2R,3S,4R,5R)-2-(2-Ethyl-2H-tetrazol-5-yl)-5-[2-(1S-hydroxymethyl-2-phenyl-ethylamino)-6-phenethylamino-purin-9-yl]-tetrahydro-furan-3,4-diol Formate Example 79 was prepared in an analogous manner to Example 23 using phenethylamine (0.003 g, 0.025 mmol) at 21° C. for 20 h. and (S)-(−)-2-amino-3-phenyl-1-propanol (0.038, 0.25 mmol) at 120° C. for 60 h. The title compound was afforded after freeze drying as a pale yellow solid (0.001 g). LC/MS SYSTEM A $R_t$=4.34 min; LC/MS SYSTEM A m/z 587 (MH$^+$).

Example 80

(2R,3R,4S,5R)-2-[6-Cyclopentylamino-2-(2-piperidin-1-yl-ethylamino)-purin-9-yl]-yl)-5-(2-isopropyl-2H-tetrazol-5-yl)-tetrahydro-furan-3,4-diol bis(Formate)

Example 80 was prepared in an analogous manner to Example 23 using Intermediate 20 (0.012 g, 0.025 mmol) and cyclopentylamine (0.002 g, 0.025 mmol) at 21° C. for 20 h. and 2-piperidinoethylamine (0.032, 0.25 mmol) at 130° C. for 14 h. The title compound was afforded after freeze drying as a brown foam (0.002 g). LC/MS SYSTEM A $R_t$=3.71 min; LC/MS SYSTEM A m/z 540 ([M−1]H$^+$).

Example 81

(2R,3R,4S,5R)-2-[6-Cyclopentylamino-2-(2-pyrrolidin-1-yl-ethylamino)-purin-9-yl]-5-(2-isopropyl-2H-tetrazol-5-yl)-tetrahydro-furan-3,4-diol Diformate Example 81 was prepared in an analogous manner to Example 23 using Intermediate 20 (0.012 g, 0.025 mmol) and cyclopentylamine (0.002 g, 0.025 mmol) at 21° C. for 20 h. and 1-(2-ethylamine)-pyrrolidine (0.029, 0.25 mmol) at 130° C. for 14 h. The title compound was afforded after freeze drying as a brown foam (0.002 g). Mass Spectrum m/z 528 (MH$^+$ for $C_{24}H_{37}N_{11}O_3$).

Example 82

N-(2-{6-(2,2-Diphenyl-ethylamino)-9-[5R-(2-ethyl-2H-tetrazol-5-yl)-3R,4S-Dihydroxy-tetrahydro-furan-2R-yl]-9H-purin-2-ylamino}-ethyl)-guanidine bis(Trifluoroacetate)

Example 83 (0.050 g, 0.09 mmol), pyrazole carboxamidine hydrochloride (0.043 g, 0.30 mmol), imidazole (0.022 g, 0.32 mmol) in anhydrous methanol (3 ml) were heated under nitrogen at 50° C. for 24 h. The reaction mixture was purified using preparative HPLC (15–65% acetonitrile). Solvent was removed in vacuo and the residue was azeotroped with methanol (×3) and titurated with diethyl ether yielding the title compound as a white solid (0.070 g). LC/MS SYSTEM A $R_t$=3.80 min; LC/MS SYSTEM A m/z 614 (MH$^+$).

Example 83

(2R,3R,4S,5R)-2-[2-(2-Amino-ethylamino)-6-(2,2-diphenyl-ethylamino)-purin-9-yl]-5-(2-ethyl-2H-tetrazol-5-yl)-tetrahydro-furan-3,4-diol Intermediate 8 (0.200 g, 0.32 mmol) and ethylenediamine (0.422 ml, 6.40 mmol) in dimethylsulfoxide (1.0 ml) were heated at 120° C. for 24 h. The reaction mixture was partitioned between ethyl acetate (50 ml) and water (50 ml). The aqueous phase was extracetd with ethyl acetate (50 ml) and the combined organic phases were washed with water (70 ml), dried (Mg2SO4) and solvent was removed in vacuo affording the title compound as a yellow-brown solid (0.060 g). LC/MS SYSTEM A $R_t$=3.98 min; LC/MS SYSTEM A m/z 570 (MH$^+$).

Example 84

(2R,3R,4S,5R)-2-[6-(2,2-Diphenyl-ethylamino)-2-(pyrrolidin-3S-ylamino)-purin-9-yl]-5-(2-ethyl-2H-tetrazol-5-yl)-tetrahydro-furan-3,4-diol bis (Trifluoroacetate)

Intermediate 8 (0.050 g, 0.08 mmol) and pyrrolidin-3S-ylamine (0.068 g, 0.80 mmol) in anhydrous dimethylsulfoxide (0.2 ml) were heated under nitrogen with stirring at 120° C. for 24 h. The reaction mixture was diluted with methanol (3 ml) and purified using preparative HPLC (20–75% acetonitrile). Solvent was removed in vacuo and the residue was azeotroped with methanol (×3) yielding the title compound as a beige coloured glassy solid (0.060 g). LC/MS SYSTEM A $R_t$=3.97 min; LC/MS SYSTEM A m/z 598 (MH$^+$).

Example 85

(2R,3S,4R,5R)-2-(2-Ethyl-2H-tetrazol-5-yl)-5-[2-(1S-hydroxymethyl-2-phenyl-ethylamino)-6-(2-morpholin-4-yl-ethylamino)-purin-9-yl]-tetrahydro-furan-3,4-diol Formate Example 85 was prepared in an analogous manner to Example 23 using 4-(2-aminoethyl)morpholine (0.003 g, 0.025 mmol) at 21° C. for 20 h. and (S)-(−)-2-amino-3-phenyl-1-propanol (0.038, 0.25 mmol) at 120° C. for 60 h.

The title compound was afforded after freeze drying as a pale yellow solid (0.001 g).

LC/MS SYSTEM A R$_t$=3.51 min; LC/MS SYSTEM A m/z 596 (MH$^+$).

Example 86

(2R,3R,4S,5R)-2-[6-Amino-2-(2-hydroxymethyl-benzylamino)-purin-9-yl]-5-(2-ethyl-2H-tetrazol-5-yl)-tetrahydro-furan-3,4-diol Trifluoroacetate Intermediate 12 (0.050 g, 0.14 mmol) and Intermediate 29 (0.112 g, 0.82 mmol) in dimethylsulfoxide (0.2 ml) were heated at 120° C. for 24 h. The crude reaction mixture was purified by column chromatography on flash silica eluting with 50% methanol in dichloromethane affording impure product as a brown film. The impure product was dissolved with methanol (3 ml) and purified using preparative HPLC (10–60% acetonitrile). Solvent was removed in vacuo and the residue was azeotroped with methanol (×3) yielding the title compound as a white solid (0.037 g). LC/MS SYSTEM A R$_t$=3.42 min; LC/MS SYSTEM A m/z 469 (MH$^+$).

Example 87

(2R,3R,4S,5R)-2-[2-(trans-4-Amino-cyclohexylamino)-6-(1-ethyl-propylamino)-purin-9-yl]-5-(2-methyl-2H-tetrazol-5-yl)-tetrahydro-furan-3,4-diol Diformate Example 87 was prepared in an analogous manner to Example 24 using 3-pentylamine (0.002 g, 0.025 mmol) at 20° C. for 48 h. and using trans 1,4-diaminocyclohexane (0.029 g, 0.25 mmol) at 130° C. for 24 h. The title compound was afforded after removal of solvent in vacuo as a brown foam. LC/MS SYSTEM A R$_t$=3.43 min; LC/MS SYSTEM A m/z 502 (MH$^+$).

Example 88

(2R,3R,4S,5R)-2-[6-(1-Ethyl-propylamino)-2-(2R-hydroxy-(R)-cyclopentylamino)-purin-9-yl]-5-(2-methyl-2H-tetrazol-5-yl)-tetrahydro-furan-3,4-diol Diformate Example 88 was prepared in an analogous manner to Example 24 using 3-pentylamine (0.002 g, 0.025 mmol) at 20° C. for 48 h. and using (R,R)-aminocyclopentan-2-ol (0.025 g, 0.25 mmol) at 130° C. for 24 h. The title compound was afforded after removal of solvent in vacuo as a solid. LC/MS SYSTEM A R$_t$=3.83 min; LC/MS SYSTEM A m/z 489 (MH$^+$).

Example 89

(2R,3R,4S,5R)-2-[6-(1-Ethyl-propylamino)-2-(2-pyridin-2-yl-ethylamino)-purin-9-yl]-5-(2-methyl-2H-tetrazol-5-yl)-tetrahydro-furan-3,4-diol Diformate Example 89 was prepared in an analogous manner to Example 24 using 3-pentylamine (0.002 g, 0.025 mmol) at 20° C. for 48 h. and using 2-(2-aminoethyl)pyridine (0.031 g, 0.25 mmol) at 130° C. for 24 h. The title compound was afforded after removal of solvent in vacuo as a solid. LC/MS SYSTEM A R$_t$=3.66 min; LC/MS SYSTEM A m/z 510 (MH$^+$).

Example 90

(2R,3R,4S,5R)-2-[6-(1-Ethyl-propylamino)-2-(2-pyrrolidin-1-yl-ethylamino)-purin-9-yl]-5-(2-methyl-2H-tetrazol-5-yl)-tetrahydro-furan-3,4-diol Diformate Example 90 was prepared in an analogous manner to Example 24 using 3-pentylamine (0.002 g, 0.025 mmol) at 20° C. for 48 h. and using amine 10 (0.029 g, 0.25 mmol) at 130° C. for 24 h. The title compound was afforded after removal of solvent in vacuo as a solid. LC/MS SYSTEM A R$_t$=3.42 min; LC/MS SYSTEM A m/z 502 (MH$^+$).

Example 91

(2R,3R,4S,5R)-2-[6-(1-Ethyl-propylamino)-2-(2-morpholin-4-yl-ethylamino)-purin-9-yl]-5-(2-methyl-2H-tetrazol-5-yl)-tetrahydro-furan-3,4-diol Diformate Example 91 was prepared in an analogous manner to Example 24 using 3-pentylamine (0.002 g, 0.025 mmol) at 20° C. for 48 h. and using 4-(2-aminoethyl)morpholine (0.033 g, 0.25 mmol) at 130° C. for 24 h. The title compound was afforded after removal of solvent in vacuo as a solid. LC/MS SYSTEM A R$_t$=3.48 min; LC/MS SYSTEM A m/z 518 (MH$^+$).

Example 92

(2R,3R,4S,5R)-2-[2-(trans-4-Amino-cyclohexylamino)-6-cyclopentylamino-purin-9-yl]-5-(2-methyl-2H-tetrazol-5-yl)-tetrahydro-furan-3,4-diol Diformate Example 92 was prepared in an analogous manner to Example 24 using cyclopentylamine (0.002 g, 0.025 mmol) at 20° C. for 48 h. and using trans 1,4-diaminocyclohexane (0.029 g, 0.25 mmol) at 130° C. for 24 h. The title compound was afforded after removal of solvent in vacuo as a solid. LC/MS SYSTEM A R$_t$=3.40 min; LC/MS SYSTEM A m/z 501 (MH$^+$).

Example 93

(2R,3R,4S,5R)-2-[2-(trans-4-Amino-cyclohexylamino)-6-(2,2-diphenyl-ethylamino)-purin-9-yl]-5-(2-methyl-2H-tetrazol-5-yl)-tetrahydro-furan-3,4-diol Diformate Example 93 was prepared in an analogous manner to Example 24 using a sealed vial (Reactivial™) with 2,2-diphenylethylamine (0.005 g, 0.025 mmol) at 20° C. for 48 h. and using neat trans 1,4-diaminocyclohexane (0.029, 0.25 mmol) at 10° C. for 90 h. The title compound was afforded after freeze drying as a brown solid (0.012 mg). LC/MS SYSTEM A R$_t$=3.69 min; LC/MS SYSTEM A m/z 612 (MH$^+$).

Example 94

(2R,3R,4S,5R)-2-[6-(2,2-Diphenyl-ethylamino)-2-(pyrrolidin-3R-ylamino)-purin-9-yl]-5-(2-methyl-2H-tetrazol-5-yl)-tetrahydro-furan-3,4-diol Diformate Example 94 was prepared in an analogous manner to Example 24 using a Reactivial™ with 2,2-diphenylethylamine (0.005 g, 0.025 mmol) at 20° C. for 48 h. and using neat pyrrolidin-3R-ylamine (0.022 g, 0.25 mmol) at 100° C. for 90 h. The title compound was afforded after freeze drying as a brown solid (0.002 mg).

LC/MS SYSTEM A R$_t$=3.73 min; LC/MS SYSTEM A m/z 584 (MH$^+$).

Example 95

(2R,3R,4S,5R)-2-[6-(2,2-Diphenyl-ethylamino)-2-(1S-hydroxymethyl-2-phenyl-ethylamino)-purin-9-yl]-5-(2-methyl-2H-tetrazol-5-yl)-tetrahydro-furan-3,4-diol Formate Example 95 was prepared in an analogous manner to Example 24 using a sealed vial (Reactivial™) with 2,2- diphenylethylamine (0.005 g, 0.025 mmol) at 20° C. for 48 h. and using (S)-(−)-2-amino-3-phenyl-1-propanol (0.038 g, 0.25 mmol) at 100° C. for 90 h. The title compound was afforded after freeze drying as a yellow solid (0.001 mg). LC/MS SYSTEM A $R_t$=4.46 min; LC/MS SYSTEM A m/z 649 (MH$^+$).

Example 96

(2R,3R,4S,5R)-2-[6-(2,2-Diphenyl-ethylamino)-2-(2R-hydroxy-(R)-cyclopentylamino)-purin-9-yl]-5-(2-methyl-2H-tetrazol-5-yl)-tetrahydro-furan-3,4-diol Formate Example 96 was prepared in an analogous manner to Example 24 using a sealed vial (Reactivial™) with 2,2-diphenylethylamine (0.005 g, 0.025 mmol) at 20° C. for 48 h. and using neat (R,R)-aminocyclopentan-2-ol (0.025 g, 0.25 mmol) at 100° C. for 90 h. The title compound was afforded after freeze drying as a beige solid (0.001 mg). LC/MS SYSTEM A $R_t$=4.32 min; LC/MS SYSTEM A m/z 599 (MH$^+$).

Example 97

(2R,3R,4S,5R)-2-[6-(2,2-Diphenyl-ethylamino)-2-(2-pyridin-2-yl-ethylamino)-purin-9-yl]-5-(2-methyl-2H-tetrazol-5-yl)-tetrahydro-furan-3,4-diol Diformate Example 97 was prepared in an analogous manner to Example 24 using a sealed vial (Reactivial™) with 2,2-diphenylethylamine (0.005 g, 0.025 mmol) at 20° C. for 48 h. and using neat 2-(2-aminoethyl)pyridine (0.030 g, 0.25 mmol) at 10° C. for 90 h. The title compound was afforded after freeze drying as a cream coloured solid (0.007 mg). LC/MS SYSTEM A $R_t$=3.96 min; LC/MS SYSTEM A m/z 620 (MH$^+$).

Example 98

(2R,3R,4S,5R)-2-[6-(2,2-Diphenyl-ethylamino)-2-(2-morpholin-4-yl-ethylamino)-purin-9-yl]-5-(2-methyl-2H-tetrazol-5-yl)-tetrahydro-furan-3,4-diol Diformate Example 98 was prepared in an analogous manner to Example 24 using a sealed vial (Reactivial™) with 2,2-diphenylethylamine (0.005 g, 0.025 mmol) at 20° C. for 48 h. and using neat 4-(2-aminoethyl)morpholine (0.033 g, 0.25 mmol) at 100° C. for 90 h. The title compound was afforded after freeze drying as a beige coloured solid (0.005 mg). LC/MS SYSTEM A $R_t$=3.70 min; LC/MS SYSTEM A m/z 628 (MH$^+$).

Example 99

(2R,3R,4S,5R)-2-[6-(2,2-Diphenyl-ethylamino)-2-(1S-hydroxymethyl-2-methyl-propylamino)-purin-9-yl]-5-(2-methyl-2H-tetrazol-5-yl)-tetrahydro-furan-3,4-diol Formate Example 99 was prepared in an analogous manner to Example 24 using a sealed vial (Reactivial™) with 2,2-diphenylethylamine (0.005 g, 0.025 mmol) at 20° C. for 48 h. and using neat (S)-(+)-2-amino-3-methyl-1-butanol (0.026 g, 0.25 mmol) at 10° C. for 90 h. The title compound was afforded after freeze drying as a white solid (0.001 mg). LC/MS SYSTEM A $R_t$=4.54 min; LC/MS SYSTEM A m/z 601 (MH$^+$).

Example 100

(2R,3R,4S,5R)-2-[2-(trans-4-Amino-cyclohexylamino)-6-(3-iodo-benzylamino)-purin-9-yl]-5-(2-ethyl-2H-tetrazol-5-yl)-tetrahydro-furan-3,4-diol Diformate Intermediate 7 (0.012 g, 0.025 mmol) was dissolved in isopropanol (0.25 ml), isopropanol (0.25 ml) containing di-isopropylethylamine (0.003 g, 0.025 mmol) was added, followed by the addition of 3-iodobenzylamine (0.006 g, 0.025 mmol) in isopropanol (0.25 ml). The mixture was left at 20° C. for 16 h. whereupon the solvent was blown off under a stream of nitrogen. The residue was dissolved in dimethylsulfoxide (0.15 ml) and transferred to a sealed vial (Reactivial ), neat trans 1,4-diaminocyclohexane (0.029 g, 0.25 mmol) was added and the reaction mixture was heated at 90° C. for 36 h. Volatiles were removed by heating the reaction mixture at 50° C. under stream of nitrogen for 4 h. and the crude reaction product was purified using autoprep. HPLC to yield the title compound after freeze-drying as a white solid (0.001 g). LC/MS SYSTEM A $R_t$=3.62 min; LC/MS SYSTEM A m/z 662 MH$^+$).

Example 101

(2R,3R,4S,5R)-2-[2-(trans-4-Amino-cyclohexylamino)-6-cyclopentylamino-purin-9-yl]-5-(2-ethyl-2H-tetrazol-5-yl)-tetrahydro-furan-3,4-diol bis(Formate)

Example 101 was prepared in an analogous manner to Example 100 using cyclopentylamine (0.002 g, 0.025 mmol) and trans 1,4-diaminocyclohexane (0.029 g, 0.25 mmol). The title compound was afforded after freeze-drying as a light brown solid (0.002 g). LC/MS SYSTEM A $R_t$=3.27 min; LC/MS SYSTEM A m/z 514 (MH$^+$).

Example 102

(2R,3S,4R,5R)-2-(2-Ethyl-2H-tetrazol-5-yl)-5-[6-phenethylamino-2-(2-piperidin-1-yl-ethylamino)-purin-9-yl]-tetrahydro-furan-3,4-diol Diformate Example 102 was prepared in an analogous manner to Example 100 using phenethylamine (0.003 g, 0.025 mmol) and 2-piperidinoethylamine (0.032 g, 0.25 mmol). The title compound was afforded after freeze-drying as a brown solid (0.003 g). LC/MS SYSTEM A $R_t$=3.59 min; LC/MS SYSTEM A m/z 564 (MH$^+$).

Example 103

(2R,3S,4R,5R)-2-(2-Ethyl-2H-tetrazol-5-yl)-5-[6-(1S-hydroxymethyl-2-ethylamino)-2-(2-piperidin-1-yl-ethylamino)-purin-9-yl]-tetrahydro-furan-3,4-diol bis(Formate)

Example 103 was prepared in an analogous manner to Example 100 using (S)-(−)-2-amino-3-phenyl-1-propanol (0.004 g, 0.025 mmol) and 2-piperidinoethylamine (0.032 g, 0.25 mmol). The title compound was afforded after freeze-drying as a yellow solid (0.006 g). LC/MS SYSTEM A $R_t$=3.45 min; LC/MS SYSTEM A m/z 594 (MH$^+$).

Example 104

(2R,3R,4S,5R)-2-[6-Cyclopentylamino-2-(2-piperidin-1-yl-ethylamino)-purin-9-yl]-5-(2-ethyl-2H-tetrazol-5-yl)-tetrahydro-furan-3,4-diol bis (Formate)

Example 104 was prepared in an analogous manner to Example 100 using cyclopentylamine (0.002 g, 0.025 mmol)

and 2-piperidinoethylamine (0.032 g, 0.25 mmol). The title compound was afforded after freeze-drying as a brown solid (0.004 g). LC/MS SYSTEM A R$_t$=3.44 min; LC/MS SYSTEM A m/z 528 (MH$^+$).

Example 105

(2R,3R,4S,5R)-2-[2-(trans-4-Amino-cyclohexylamino)-6-(3-iodo-benzylamino)-purin-9-yl]-5-(2-methyl-2H-tetrazol-5-yl)-tetrahydro-furan-3,4-diol bis(Formate)

Intermediate 17 (0.012 g, 0.025 mmol) was dissolved in isopropanol (0.25 ml) in a sealed vial (Reactivial™), isopropanol (0.25 ml) containing di-isopropylethylamine (0.003 g, 0.025 mmol) was added, followed by the addition of 3-iodobenzylamine (0.006 g, 0.025 mmol) in isopropanol (0.25 ml). The mixture was left at 20° C. for 20 h. whereupon the solvent was blown off under a stream of nitrogen. The residual gum was dissolved in dimethylsulphoxide (3 drops), and neat trans 1,4-diaminocyclohexane (0.029 g, 0.25 mmol) was added and the mixture was heated at 130° C. for 72 h. The crude reaction product was purified using autoprep. HPLC to yield the title compound after freeze-drying as a beige coloured solid (0.004 g). LC/MS SYSTEM A R$_t$=3.69 min; LC/MS SYSTEM A m/z 648 (MH$^+$).

Example 106

(2R,3R,4S,5R)-2-[6-(3-Iodo-benzylamino)-2-(2-piperidin-1-yl-ethylamino)-purin-9-yl]-5-(2-methyl-2H-tetrazol-5-yl)-tetrahydro-furan-3,4-diol bis (Formate)

Example 106 was prepared in an analogous manner to Example 105 using 3-iodobenzylamine (0.006 g, 0.025 mmol) and neat 2-piperidinoethylamine (0.032, 0.25 mmol) at 100° C. for 48 h. The title compound was afforded after freeze drying as a cream coloured solid (0.003 g). LC/MS SYSTEM A R$_t$=3.81 min; LC/MS SYSTEM A m/z 662 (MH$^+$).

Example 107

(2R,3R,4S,5R)-2-[6-(1S-Hydroxymethyl-2-phenyl-ethylamino)-2-(2-piperidin-1-yl-ethylamino)-purin-9-yl]-5-(2-methyl-2H-tetrazol-5-yl)-tetrahydro-furan-3,4-diol bis(Formate)

Example 107 was prepared in an analogous manner to Example 105 using (S)-(-)-2-amino-3-phenyl-1-propanol (0.004 g, 0.025 mmol) and neat 2-piperidinoethylamine (0.032, 0.25 mmol) at 100° C. for 48 h. The title compound was afforded after freeze drying as a yellow solid (0.003 g). LC/MS SYSTEM A R$_t$=3.50 min; LC/MS SYSTEM A m/z 580 (MH$^+$).

Example 108

(2R,3R,4S,5R)-2-[6-(3-Iodo-benzylamino)-2-(2-pyrrolidin-1-yl-ethylamino)-purin-9-yl]-5-(2-methyl-2H-tetrazol-5-yl)-tetrahydro-furan-3,4-diol bis (Formate)

Example 108 was prepared in an analogous manner to Example 105 using 3-iodobenzylamine (0.006 g, 0.025 mmol) and neat 1-(2-ethylamine)-pyrrolidine (0.029 g, 0.25 mmol) at 10° C. for 48 h. The title compound was afforded after freeze drying as a cream coloured solid (0.002 g). LC/MS SYSTEM A R$_t$=3.76 min; LC/MS SYSTEM A m/z 648 (MH$^+$).

Example 109

(2R,3R,4S,5R)-2-[2-(1S-Hydroxymethyl-2-phenyl-ethylamino)-6-(3-iodo-benzylamino)-purin-9-yl]-5-(2-methyl-2H-tetrazol-5-yl)-tetrahydro-furan-3,4-diol Formate Example 109 was prepared in an analogous manner to Example 105 using 3-iodobenzylamine (0.006 g, 0.025 mmol) and neat (S)-(-)-2-amino-3-phenyl-1-propanol (0.038 g, 0.25 mmol) at 10° C. for 24 h. The title compound was afforded after freeze drying as a white solid (0.001 g). LC/MS SYSTEM A R$_t$=4.65 min; LC/MS SYSTEM A m/z 685 (MH$^+$).

Example 110

(2R,3R,4S,5R)-2-[2,6-Bis-(1S-Hydroxymethyl-2-phenyl-ethylamino)-purin-9-yl]-5-(2-methyl-2H-tetrazol-5-yl)-tetrahydro-furan-3,4-diol Formate Example 110 was prepared in an analogous manner to Example 105 using 2-piperidinoethylamine (0.004 g, 0.025 mmol) and neat (S)-(-)-2-amino-3-phenyl-1-propanol (0.038 g, 0.25 mmol) at 100° C. for 24 h. The title compound was afforded after freeze drying as a cream coloured solid (0.008 g). LC/MS SYSTEM A R$_t$=4.07 min; LC/MS SYSTEM A m/z 603 (MH$^+$).

Example 111

(2R,3R,4S,5R)-2-[6-(1S-Hydroxymethyl-2-phenyl-ethylamino)-2-(2-pyrrolidin-1-yl-ethylamino)-purin-9-yl]-5-(2-methyl-2H-tetrazol-5-yl)-tetrahydro-furan-3,4-diol bis(Formate)

Example 111 was prepared in an analogous manner to Example 105 using 2-piperidinoethylamine (0.004 g, 0.025 mmol) and neat 1-(2-ethylamine)-pyrrolidine (0.029 g, 0.25 mmol) at 10° C. for 48 h. The title compound was afforded after freeze drying as a brown solid (0.003 g). LC/MS SYSTEM A R$_t$=3.45 min; LC/MS SYSTEM A m/z 566 (MH$^+$).

Example 112

(2R,3R,4S,5R)-2-[6-Cyclopentylamino-2-(2-pyrrolidin-1-yl-ethylamino)-purin-9-yl]-5-(2-methyl-2H-tetrazol-5-yl)-tetrahydro-furan-3,4-diol bis (Formate)

Example 112 was prepared in an analogous manner to Example 105 using cyclopentylamine (0.002 g, 0.025 mmol) and neat 1-(2-ethylamine)-pyrrolidine (0.029 g, 0.25 mmol) at 10° C. for 48 h. The title compound was afforded after freeze drying as a yellow solid (0.003 g). LC/MS SYSTEM A R$_t$=3.43 min; LC/MS SYSTEM A m/z 501 (MH$^+$).

Example 113

(2R, 3R,4S, 5R)-2-[6-(2,2-Diphenyl-ethylamino)-2-(tetrahydro-pyran-4-ylamino)-purin-9-yl]-5-(2-ethyl-2H-tetrazol-5-yl)-tetrahydro-furan-3,4-diol Trifluoroacetate Intermediate 8 (0.124 g, 0.19 mmol), 4-aminotetrahydropyran[1] (0.089 g, 0.88 mmol), dimethylsulfoxide (0.4 ml) in N,N-diisopropylethylamine (2 ml) were heated at 90° C. for 16 h, then at 125° C. for 120 h. Solvent was removed in vacuo. The crude material was purified by preparative HPLC (10–100% acetonitrile over 22 min). Solvent was removed in vacuo and the residue was freeze-dried to give the title compound as a brown solid (0.019 g). LC/MS SYSTEM A $R_t$=4.27 min; LC/MS SYSTEM A m/z 613 (MH$^+$).

[1] Preparable according to the method of: Johnston, Thomas P.; McCaler, George S.; Opliger, Pamela S.; Laster, W. Russell; Montgomery, John A., J. Med. Chem., 1971, 14, 600–14.

Example 114

(2R,3R,4S,5R)-2-[6-(2,2-Diphenyl-ethylamino)-2-tetrahydro-thiopyran-4-ylamino)-purin-9-yl]-5-(2-ethyl-2H-tetrazol-5-yl)-tetrahydro-furan-3,4-diol Trifluoroacetate Example 114 was prepared in an analogous manner to Example 113 using 4-aminotetrahydrothiopyran[1] (0.102 g, 0.87 mmol) at 90° C. for 16 h., then at 125° C. for 120 h. The title compound was afforded after freeze drying as a brown solid (0.020 g). LC/MS SYSTEM A $R_t$=4.55 min; LC/MS SYSTEM A m/z 629 (MH$^+$).

[1] Preparable according to the method of: Subramanian, Pullachipatti K.; Ramalingam, Kondareddiar; Satyamurthy, Nagichettiar; Berlin, K. Darrell. J. Org. Chem., 1981, 46, 4376–83.

Example 115

(2R,3R,4S,5R)-2-[6-(2,2-Diphenyl-ethylamino)-2-(1,1--dioxo-hexahydro-1.lamda.6-thiopyran-4-ylamino)-purin-9-yl]-5-(2-ethyl-2H-tetrazol-5-yl)-tetrahydro-furan-3,4-diol Trifluoroacetate Example 115 was prepared in an analogous manner to Example 113 using 1,1-dioxo-hexahydro-1.lamda.6-thiopyran-4-ylamine[1] (0.131g, 0.88 mmol) at 90° C. for 16 h., then at 125° C. for 120 h. The title compound was afforded after freeze drying as a brown solid (0.021 g). LC/MS SYSTEM A $R_t$=4.17 min; LC/MS SYSTEM A m/z 661 (MH$^+$).

[1] Preparable according to the method of: Barkenbus, C. and Wuellner, J. A., J. Am. Chem. Soc., 1955, 77, 3866–69.

Biological Data
(A) Agonist Activity Against Receptor Sub-types.

The compounds of Examples 1 to 115 were tested in screen (1) (agonist activity against receptor sub-types) and the results obtained were as follows:

| Example No | Version Tested | *A2a | *A1 | *A3 |
| --- | --- | --- | --- | --- |
| 1 | HCl, TFA | 0.53 | 89.3 | >549 |
| 2 | TFA | 0.92 | 123.6 | >216 |
| 3 | Freebase | 0.84 | 230.8 | >116 |
| 4 | HCl, TFA, Acetate | 0.149 | 205.4 | >244 |
| 5 | Freebase | 0.76 | 700.4 | >181 |
| 6 | Acetate | 0.14 | 34.4 | >256 |
| 7 | Acetate | 0.12 | 26.2 | >161 |
| 8 | Acetate | 0.1 | 12.6 | >133 |
| 9 | Acetate | 0.45 | 377 | >42 |
| 10 | TFA, HCl | 0.11 | 22.1 | 3.66 |
| 11 | TFA, HCl | 0.109 | 38.1 | >356 |
| 12 | TFA | 0.57 | 31.2 | >243 |
| 13 | TFA | 0.64 | 266.9 | >232 |
| 14 | Formate | 0.55 | 181.1 | >209 |
| 15 | Formate | 0.55 | 139.5 | >209 |
| 16 | Formate | 0.3 | 516.4 | >209 |
| 17 | Formate | 0.69 | 247.6 | >346 |
| 18 | Formate | 0.36 | 136.7 | >223 |
| 19 | TFA | 0.21 | 85.6 | >382 |
| 20 | TFA | 0.14 | 253 | >183 |
| 21 | Formate, TFA, HCl | 0.69 | 237.9 | >442 |
| 22 | TFA | 0.67 | 86.4 | >188 |
| 23 | Formate | 0.8 | 159 | >336 |
| 24 | Formate | 0.36 | >4798 | >157 |
| 25 | Formate | 0.56 | 211.8 | >388 |
| 26 | Formate | 0.86 | 241.4 | >329 |
| 27 | Formate | 0.08 | 449.7 | >286 |
| 28 | Formate | 0.36 | >=1250 | >151 |
| 29 | Formate | 0.87 | >3561 | >105 |
| 30 | Formate | 0.43 | >7976 | >105 |
| 31 | Formate | 0.49 | >=3680 | >100 |
| 32 | Formate | 0.026 | 56.2 | >100 |
| 33 | Formate | 0.16 | >4045 | >172 |
| 34 | Formate | 0.13 | 1316 | >173 |
| 35 | Formate | 0.79 | 123 | >201 |
| 36 | Formate | 0.99 | 1.9 | >315 |
| 37 | Formate | 0.52 | 119.1 | >348 |
| 38 | Formate | 0.13 | 946 | >315 |
| 39 | Formate | 0.31 | 1429 | >315 |
| 40 | Formate | 0.31 | 22.1 | >232 |
| 41 | Formate | 0.73 | 28.9 | >232 |
| 42 | Formate | 0.63 | 414.9 | >413 |
| 43 | Trifluoroacetate | 2.23 | 71.35 | >546 |
| 44 | Trifluoroacetate | 3.25 | 44.11 | >546 |
| 45 | Trifluoroacetate | 2.26 | >1578.00 | >420 |
| 46 | Trifluoroacetate | 1.37 | 64.00 | >216 |
| 47 | Trifluoroacetate | 1.06 | 27.40 | >216 |
| 48 | Freebase | 4.12 | 102.00 | >181 |
| 49 | Freebase | 3.28 | 158.70 | >214 |
| 50 | Acetate | 1.48 | 2443.00 | >86 |
| 51 | Acetate | 1.46 | 144.00 | >42 |
| 52 | Acetate | 9.90 | 481.30 | >736 |
| 53 | Formate | 4.14 | 298.30 | >960 |
| 54 | Formate | 1.16 | 267.60 | >175 |
| 55 | Trifluoroacetate | 5.77 | 1136.00 | >435 |
| 56 | Formate | 4.90 | 570.90 | >297 |
| 57 | Formate | 2.42 | 376.10 | >362 |
| 58 | Formate | 6.07 | 1119.00 | >515 |
| 59 | Formate | 2.34 | 92.30 | >749 |
| 60 | Trifluoroacetate | 4.24 | 69.10 | >385 |
| 61 | Formate | 9.20 | 323.00 | >150 |
| 62 | Formate | 2.29 | 21.10 | >295 |
| 63 | Formate | 5.86 | 55.60 | >326 |
| 64 | Formate | 2.54 | 21.30 | >326 |
| 65 | Formate | 2.46 | 61.50 | >158 |
| 66 | Formate | 1.53 | 48.60 | >158 |
| 67 | Formate | 2.96 | 73.85 | >326 |
| 68 | Formate | 3.50 | 56.20 | >331 |
| 69 | Formate | 6.60 | 515.30 | >148 |
| 70 | Formate | 7.24 | 30.55 | >405 |
| 71 | Formate | 1.99 | 14.78 | >158 |
| 72 | Formate | 6.48 | 848.50 | >158 |
| 73 | Formate | 5.75 | 818.40 | >171 |
| 74 | Formate | 2.79 | 201.70 | >171 |
| 75 | Formate | 1.40 | 121.50 | >174 |
| 76 | Formate | 2.93 | 215.30 | >155 |
| 77 | Formate | 3.30 | 101.30 | >200 |
| 78 | Formate | 4.00 | 31.00 | >181 |
| 79 | Formate | 2.40 | 165.30 | >155 |
| 80 | Formate | 2.37 | 77.10 | >164 |
| 81 | Formate | 4.77 | 89.11 | >156 |
| 82 | Trifluoroacetate | 5.56 | 520.50 | >189 |
| 83 | Freebase | 4.82 | 130.10 | >362 |
| 84 | Trifluoroacetate | 2.50 | 490.80 | >103 |
| 85 | Formate | 6.11 | 192.90 | >179 |
| 86 | Trifluoroacetate | 2.16 | 16.90 | >179 |
| 87 | Formate | 1.61 | 348.11 | >320 |
| 88 | Formate | 4.53 | >11750.00 | >89 |
| 89 | Formate | 2.22 | >9363.00 | >243 |
| 90 | Formate | 2.41 | 245.90 | >267 |
| 91 | Formate | 1.75 | >7461.00 | >270 |
| 92 | Formate | 1.24 | 253.70 | >192 |
| 93 | Formate | 5.07 | 922.00 | >153 |
| 94 | Formate | 2.39 | 385.90 | >411 |
| 95 | Formate | 2.10 | 4687.00 | >153 |
| 96 | Formate | 2.14 | 5177.00 | >153 |
| 97 | Formate | 2.34 | 1413.00 | >240 |

-continued

| Example No | Version Tested | *A2a | *A1 | *A3 |
|---|---|---|---|---|
| 98 | Formate | 2.28 | 126.50 | >160 |
| 99 | Formate | 4.82 | 87.00 | >130 |
| 100 | Formate | 5.71 | 292.70 | >127 |
| 101 | Formate | 1.51 | 39.00 | >195 |
| 102 | Formate | 6.36 | 321.00 | >195 |
| 103 | Formate | 3.91 | 48.50 | >184 |
| 104 | Formate | 4.04 | 113.40 | >235 |
| 105 | Formate | 1.07 | >2999.00 | >233 |
| 106 | Formate | 1.12 | 100.30 | >201 |
| 107 | Formate | 1.27 | 89.10 | >233 |
| 108 | Formate | 2.25 | 111.30 | >201 |
| 109 | Formate | 8.54 | 17.70 | >446 |
| 110 | Formate | 5.00 | 3.13 | >315 |
| 111 | Formate | 2.92 | 298.50 | >315 |
| 112 | Formate | 2.19 | 472.30 | >315 |
| 113 | TFA | 0.72 | 184.4 | >297.0 |
| 114 | TFA | 0.58 | 242.2 | >2972.0 |
| 115 | TFA | 0.36 | 37.7 | >297.0 |

*Biological data will be the mean of the all the versions tested.

Values given in the Table are $EC_{50}$ values as a ratio of that of NECA.

The versions (when different from those described in the Examples) were prepared from the free base by treatment (e.g. in chromatography or otherwise) by the appropriate acid.

(B) Antigen Induced Lung Eosinophil Accumulation in Sensitised Guinea Pigs.

The compounds of Examples 1a and 11a were tested in screen (2) (guinea pig lung eosinophil accumulation) and the results obtained were as follows:

| Compound | $ED_{50}$ |
|---|---|
| Example 1a | 6 |
| Example 11a | 6 |

Values given in the Table are $ED_{50}$ values measured as μg/L airstream concentration.

| ABBREVIATIONS | |
|---|---|
| TMS | trimethylsilyl |
| TFA | trifluoroacetic acid |
| DMF | N,N-dimethylformamide |
| NECA | N-ethylcarboxamideadenosine |
| DMAP | 4-dimethylaminopyridine |
| TEMPO | 2,2,6,6-tetramethyl-1-piperidinyloxy, free radical |
| TMSOTf | Trimethylsilyltrifluoromethylsulphonate |
| DBU | 1,8-diazabicyclo[5.4.0]undec-7-ene |
| BSA | bistrimethylsilylacetamide |
| DCM | dichloromethane |
| DAST | diethylaminosulphur trifluoride |
| Ph | phenyl |
| CDI | carbonyldiimidazole |
| NSAID | non-steroidal antiinflammatory drug |

We claim:

1. A method of prophylactic treatment of inflammatory diseases comprising administering to a patient a pharmaceutically effective amount of a compound of the formula (2R,3R,4S,5R)-2-[6-amino-2-(1S-hydroxymethyl-2-phenyl-ethylamino)-purin-9-yl]-5-(2-ethyl-2H-tetrazol-5-yl)-tetrahydro-furan-3,4-diol or a salt or solvate thereof.

2. A method of prophylactic treatment of inflammatory diseases comprising administering to a patient a pharmaceutically effective amount of a compound of the formula (2R,3R,4S,5R)-2-[6-amino-2-(1S-hydroxymethyl-2-phenyl-ethylamino)-purin-9-yl]-5-(2-ethyl-2H-tetrazol-5-yl)-tetrahydro-furan-3,4-diol maleate.

* * * * *